(12) United States Patent
Grunwald et al.

(10) Patent No.: US 10,335,240 B2
(45) Date of Patent: *Jul. 2, 2019

(54) ENDOVASCULAR NAVIGATION SYSTEM AND METHOD

(71) Applicant: ARROW INTERNATIONAL, INC., Wayne, PA (US)

(72) Inventors: Sorin Grunwald, Palo Alto, CA (US); Bradley Hill, Santa Clara, CA (US)

(73) Assignee: ARROW INTERNATIONAL, INC., Wayne, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/953,391

(22) Filed: Nov. 29, 2015

(65) Prior Publication Data
US 2016/0151118 A1 Jun. 2, 2016

Related U.S. Application Data

(63) Continuation of application No. 11/431,118, filed on May 8, 2006, now Pat. No. 9,198,600.
(Continued)

(51) Int. Cl.
*A61B 34/20* (2016.01)
*A61B 5/06* (2006.01)
(Continued)

(52) U.S. Cl.
CPC ............... *A61B 34/20* (2016.02); *A61B 5/02* (2013.01); *A61B 5/06* (2013.01); *A61B 5/7246* (2013.01);
(Continued)

(58) Field of Classification Search
CPC .................................................. A61B 34/20
See application file for complete search history.

(56) References Cited

U.S. PATENT DOCUMENTS

| 3,565,062 A | 2/1971 | Kuris et al. |
| 3,670,626 A | 6/1972 | Olson et al. |

(Continued)

FOREIGN PATENT DOCUMENTS

| EP | 0238791 A2 | 9/1987 |
| EP | 0917069 A1 | 5/1999 |

(Continued)

OTHER PUBLICATIONS

Bidoggia et al.; Transseptal left heart catheterization: usefulness of the intracavitary electrocardiogram in the localization of the fossa ovalis; Catheterization and Cardiovascular Diagnosis; New York, NY; vol. 24; No. 3; pp. 221-225; Nov. 1, 1991.

(Continued)

*Primary Examiner* — Rochelle D Turchen
(74) *Attorney, Agent, or Firm* — Baker & Hostetler LLP

(57) ABSTRACT

The endovascular navigation system includes an elongate flexible member configured to access the venous vasculature of a patient, a sensor disposed at a distal end of the elongate flexible member and configured to sense a physiological characteristic of the venous vasculature, a processor and an output device. The processor is configured to receive and process the physiological characteristic of the venous vasculature, and to determine that the position of the distal end of the elongate flexible member is within a predetermined structure within the venous vasculature. The output device is configured to display a visual indication that the distal end of the elongate flexible member is within the predetermined structure within the venous vasculature, where the visual indication is different from the physiological characteristic of the venous vasculature of the patient.

24 Claims, 51 Drawing Sheets

Related U.S. Application Data

(60) Provisional application No. 60/682,002, filed on May 18, 2005, provisional application No. 60/678,209, filed on May 6, 2005.

(51) Int. Cl.
*A61B 8/06* (2006.01)
*A61B 8/08* (2006.01)
*A61B 8/12* (2006.01)
*A61B 8/00* (2006.01)
*A61B 5/02* (2006.01)
*A61B 5/00* (2006.01)
*A61B 8/04* (2006.01)
*A61B 5/0215* (2006.01)
*A61B 5/1459* (2006.01)
*A61B 17/00* (2006.01)
*A61B 90/00* (2016.01)

(52) U.S. Cl.
CPC ............ *A61B 5/7271* (2013.01); *A61B 5/742* (2013.01); *A61B 8/04* (2013.01); *A61B 8/06* (2013.01); *A61B 8/0841* (2013.01); *A61B 8/12* (2013.01); *A61B 8/42* (2013.01); *A61B 8/445* (2013.01); *A61B 8/4472* (2013.01); *A61B 8/461* (2013.01); *A61B 8/488* (2013.01); *A61B 8/5207* (2013.01); *A61B 5/02152* (2013.01); *A61B 5/1459* (2013.01); *A61B 2017/00106* (2013.01); *A61B 2034/2063* (2016.02); *A61B 2090/378* (2016.02)

(56) References Cited

U.S. PATENT DOCUMENTS

| | | | |
|---|---|---|---|
| 4,143,650 | A | 3/1979 | Hatke |
| 4,324,258 | A | 4/1982 | Huebscher et al. |
| 4,503,861 | A | 3/1985 | Entrekin |
| 4,549,879 | A | 10/1985 | Groshong et al. |
| 4,583,552 | A * | 4/1986 | Iinuma ............ G01S 15/8979 600/441 |
| 4,644,960 | A | 2/1987 | Johans |
| 4,667,679 | A | 5/1987 | Sahota |
| 4,692,148 | A | 9/1987 | Kantrowitz et al. |
| 4,790,831 | A | 12/1988 | Skribiski |
| 4,849,172 | A | 7/1989 | Yafuso et al. |
| 4,856,529 | A | 8/1989 | Segal |
| 4,896,677 | A | 1/1990 | Kaneko et al. |
| 4,966,148 | A | 10/1990 | Millar |
| 4,967,753 | A | 11/1990 | Haase et al. |
| 5,038,789 | A * | 8/1991 | Frazin ..................... A61B 8/06 600/471 |
| 5,046,497 | A | 9/1991 | Millar |
| 5,047,930 | A | 9/1991 | Martens et al. |
| 5,058,597 | A | 10/1991 | Onoda et al. |
| 5,078,148 | A | 1/1992 | Nassi et al. |
| 5,078,678 | A | 1/1992 | Katims |
| 5,078,714 | A * | 1/1992 | Katims ............ A61M 25/0105 604/264 |
| 5,105,818 | A | 4/1992 | Christian et al. |
| 5,107,841 | A | 4/1992 | Sturgill |
| 5,125,410 | A | 6/1992 | Misono et al. |
| 5,174,295 | A | 12/1992 | Christian et al. |
| 5,190,045 | A | 3/1993 | Frazin |
| 5,207,226 | A | 5/1993 | Bailin et al. |
| 5,220,924 | A | 6/1993 | Frazin |
| 5,269,289 | A | 12/1993 | Takehana et al. |
| 5,271,404 | A | 12/1993 | Corl et al. |
| 5,311,871 | A | 5/1994 | Yock |
| 5,431,168 | A | 7/1995 | Webster, Jr. |
| 5,431,628 | A | 7/1995 | Millar |
| 5,477,858 | A | 12/1995 | Norris et al. |
| 5,492,125 | A | 2/1996 | Kim et al. |
| 5,513,639 | A | 5/1996 | Satomi et al. |
| 5,540,230 | A | 7/1996 | Vilkomerson |
| 5,546,949 | A | 8/1996 | Frazin et al. |
| 5,566,674 | A | 10/1996 | Weng |
| 5,575,286 | A | 11/1996 | Weng et al. |
| 5,588,432 | A | 12/1996 | Crowley |
| 5,640,961 | A | 6/1997 | Verdonk |
| 5,657,760 | A | 8/1997 | Ying et al. |
| 5,666,958 | A | 9/1997 | Rothenberg et al. |
| 5,669,389 | A | 9/1997 | Rotteveel et al. |
| 5,693,032 | A | 12/1997 | Bierman |
| 5,697,377 | A | 12/1997 | Wittkampf |
| 5,722,959 | A | 3/1998 | Bierman |
| 5,733,323 | A | 3/1998 | Buck et al. |
| 5,749,364 | A | 5/1998 | Sliwa, Jr. et al. |
| 5,782,766 | A | 7/1998 | Weng et al. |
| 5,785,657 | A | 7/1998 | Breyer et al. |
| 5,795,298 | A | 8/1998 | Vesely et al. |
| 5,803,083 | A | 9/1998 | Buck et al. |
| 5,857,973 | A | 1/1999 | Ma et al. |
| 5,860,951 | A | 1/1999 | Eggers et al. |
| 5,876,342 | A | 3/1999 | Chen et al. |
| 5,878,746 | A | 3/1999 | Lemelson et al. |
| 5,891,036 | A | 4/1999 | Izumi |
| 5,897,488 | A | 4/1999 | Ueda |
| 5,908,385 | A | 6/1999 | Chechelski et al. |
| 5,935,143 | A | 8/1999 | Hood |
| 5,938,603 | A | 8/1999 | Ponzi |
| 5,999,846 | A | 12/1999 | Pardey et al. |
| 6,007,491 | A | 12/1999 | Ling et al. |
| 6,059,731 | A | 5/2000 | Seward et al. |
| 6,083,170 | A | 7/2000 | Ben-Haim |
| 6,120,445 | A | 9/2000 | Grunwald |
| 6,179,781 | B1 | 1/2001 | Phillips |
| 6,179,782 | B1 | 1/2001 | Cuce |
| 6,213,947 | B1 | 4/2001 | Phillips |
| 6,251,073 | B1 | 6/2001 | Imran et al. |
| 6,264,611 | B1 | 7/2001 | Ishikawa et al. |
| 6,364,838 | B1 | 4/2002 | Freiburger et al. |
| 6,500,130 | B2 | 12/2002 | Kinsella et al. |
| 6,520,916 | B1 | 2/2003 | Brennen |
| 6,542,626 | B1 | 4/2003 | Brouwer et al. |
| 6,551,244 | B1 | 4/2003 | Gee |
| 6,556,695 | B1 | 4/2003 | Packer et al. |
| 6,561,979 | B1 | 5/2003 | Wood et al. |
| 6,591,144 | B2 | 7/2003 | Pigott |
| 6,594,524 | B2 | 7/2003 | Esteller et al. |
| 6,612,992 | B1 | 9/2003 | Hossack et al. |
| 6,629,951 | B2 | 10/2003 | Laufer et al. |
| 6,638,243 | B2 | 10/2003 | Kupiecki |
| 6,685,648 | B2 | 2/2004 | Flaherty et al. |
| 6,689,119 | B1 | 2/2004 | Di Caprio et al. |
| 6,695,785 | B2 | 2/2004 | Brisken et al. |
| 6,704,590 | B2 | 3/2004 | Haldeman |
| 6,719,756 | B1 | 4/2004 | Muntermann |
| 6,733,454 | B1 | 5/2004 | Bakircioglu et al. |
| 6,740,590 | B1 | 5/2004 | Yano et al. |
| 6,749,606 | B2 | 6/2004 | Keast et al. |
| 6,814,702 | B2 | 11/2004 | Redano |
| 6,866,677 | B2 | 3/2005 | Douk et al. |
| 6,896,658 | B2 | 5/2005 | Ji et al. |
| 6,931,269 | B2 | 8/2005 | Terry |
| 6,973,352 | B1 | 12/2005 | Tsutsui et al. |
| 7,037,290 | B2 | 5/2006 | Gardeski et al. |
| 7,043,293 | B1 | 5/2006 | Baura |
| 7,089,928 | B2 | 8/2006 | Besharim et al. |
| 7,134,994 | B2 | 11/2006 | Alpert et al. |
| 7,150,716 | B2 | 12/2006 | Jones et al. |
| 7,200,435 | B2 | 4/2007 | Ricci et al. |
| 7,204,798 | B2 | 4/2007 | Ideblick et al. |
| 7,225,013 | B2 | 5/2007 | Geva et al. |
| 7,346,393 | B2 | 3/2008 | Spinelli et al. |
| 7,367,949 | B2 | 5/2008 | Korhonen et al. |
| 7,393,501 | B2 | 7/2008 | Zumeris et al. |
| 7,422,563 | B2 | 9/2008 | Roschak et al. |
| 7,433,853 | B2 | 10/2008 | Brockway et al. |
| 7,485,095 | B2 | 2/2009 | Shusterman |
| 7,599,730 | B2 | 10/2009 | Hunter et al. |
| 7,627,386 | B2 | 12/2009 | Mo et al. |
| 7,640,055 | B2 | 12/2009 | Geva et al. |

(56) References Cited

U.S. PATENT DOCUMENTS

| | | |
|---|---|---|
| 7,668,579 B2 | 2/2010 | Lynn |
| 7,697,972 B2 | 4/2010 | Verard et al. |
| 7,708,696 B2 | 5/2010 | Ritter et al. |
| 7,833,221 B2 | 11/2010 | Voegele et al. |
| 7,981,038 B2 | 7/2011 | Kanade et al. |
| 7,991,458 B2 | 8/2011 | Hardahl et al. |
| 8,046,052 B2 | 10/2011 | Verard et al. |
| 8,052,648 B2 | 11/2011 | Dikeman et al. |
| 8,060,185 B2 | 11/2011 | Hunter et al. |
| 2002/0045810 A1 | 4/2002 | Ben-Haim |
| 2002/0087156 A1 | 7/2002 | Maguire et al. |
| 2002/0099292 A1 | 7/2002 | Brisken et al. |
| 2002/0111548 A1 | 8/2002 | Swanson et al. |
| 2002/0151790 A1 | 10/2002 | Abend |
| 2002/0156363 A1 | 10/2002 | Hunter et al. |
| 2002/0168618 A1 | 11/2002 | Anderson et al. |
| 2002/0188257 A1 | 12/2002 | Bierman |
| 2003/0083717 A1 | 5/2003 | Mlynski et al. |
| 2003/0109785 A1 | 6/2003 | Buck et al. |
| 2003/0191392 A1 | 10/2003 | Haldeman |
| 2004/0011358 A1 | 1/2004 | Smaldone et al. |
| 2004/0039436 A1 | 2/2004 | Spenser et al. |
| 2004/0102719 A1 | 5/2004 | Keith et al. |
| 2004/0116809 A1 | 6/2004 | Chow et al. |
| 2004/0116969 A1 | 6/2004 | Owen et al. |
| 2004/0158143 A1 | 8/2004 | Flaherty et al. |
| 2004/0204636 A1* | 10/2004 | Diab ............... A61B 5/14546 600/323 |
| 2004/0254523 A1 | 12/2004 | Fitzgerald et al. |
| 2004/0260346 A1* | 12/2004 | Overall ............ A61B 5/02444 607/4 |
| 2005/0085718 A1 | 4/2005 | Shahidi |
| 2005/0148836 A1 | 7/2005 | Kleen et al. |
| 2005/0159738 A1 | 7/2005 | Visram et al. |
| 2005/0182295 A1* | 8/2005 | Soper ............... A61B 1/0008 600/117 |
| 2005/0203360 A1* | 9/2005 | Brauker ............ A61B 5/1468 600/345 |
| 2006/0079868 A1 | 4/2006 | Makin et al. |
| 2006/0084883 A1 | 4/2006 | Linker |
| 2006/0094923 A1 | 5/2006 | Mate |
| 2007/0016068 A1 | 1/2007 | Grunwald et al. |
| 2007/0016069 A1 | 1/2007 | Grunwald et al. |
| 2007/0016070 A1 | 1/2007 | Grunwald et al. |
| 2007/0016072 A1 | 1/2007 | Grunwald et al. |
| 2007/0055142 A1* | 3/2007 | Webler ............. A61B 5/06 600/425 |
| 2007/0167738 A1 | 7/2007 | Timinger et al. |
| 2007/0276334 A1 | 11/2007 | Bierman et al. |
| 2008/0188740 A1 | 8/2008 | Diaz et al. |
| 2009/0005675 A1 | 1/2009 | Grunwald et al. |
| 2009/0118612 A1 | 5/2009 | Grunwald et al. |
| 2009/0143740 A1 | 6/2009 | Bierman et al. |
| 2009/0177090 A1 | 7/2009 | Grunwald et al. |
| 2011/0257600 A1 | 10/2011 | Kessler |
| 2012/0035434 A1 | 2/2012 | Ferren et al. |
| 2012/0136242 A1 | 5/2012 | Qi et al. |
| 2013/0289417 A1 | 10/2013 | Grunwald et al. |
| 2013/0296693 A1 | 11/2013 | Wenzel et al. |
| 2013/0296725 A1 | 11/2013 | Lee et al. |

FOREIGN PATENT DOCUMENTS

| | | | |
|---|---|---|---|
| EP | 1181895 A2 | 2/2002 | |
| EP | 1393674 A1 | 3/2004 | |
| EP | 1509866 A1 | 3/2005 | |
| JP | 62500703 A | 3/1987 | |
| JP | 62236532 A | 10/1987 | |
| JP | H08229044 A | 9/1996 | |
| JP | H09253084 A | 9/1997 | |
| JP | H10277039 A | 10/1998 | |
| JP | 2000514320 A | 10/2000 | |
| JP | 2001506140 A | 5/2001 | |
| JP | 2003506132 A | 2/2003 | |
| JP | 2004500210 A | 1/2004 | |
| JP | 2004130114 A | 4/2004 | |
| JP | 2004522480 A | 7/2004 | |
| JP | 2006513731 A | 4/2006 | |
| JP | 4017843 B2 | 12/2007 | |
| JP | 4183456 B2 | 11/2008 | |
| JP | 4501972 B2 | 7/2010 | |
| JP | 3205040 U | 6/2016 | |
| WO | WO1986002540 | 5/1986 | |
| WO | WO1991004707 | 4/1991 | |
| WO | WO1993008738 | 5/1993 | |
| WO | WO1997018768 | 5/1997 | |
| WO | WO1997044089 | 11/1997 | |
| WO | WO1998008440 | 3/1998 | |
| WO | WO2001070303 | 9/2001 | |
| WO | WO2001074249 | 10/2001 | |
| WO | WO2003098523 | 11/2003 | |
| WO | WO 2005053527 A1 * | 6/2005 | ........... A91B 5/0002 |
| WO | WO2006051523 A2 | 5/2006 | |
| WO | WO2007047360 A2 | 4/2007 | |
| WO | WO2007082093 A2 | 7/2007 | |

OTHER PUBLICATIONS

Radke et al.; Control of the placement of a central venous catheter using doppler ultrasound; Der Anaesthesist May 1990; vol. 39; No. 5; pp. 283-287; May 1990.

Benchimol et al.; Right atrium and superior vena cava flow velocity in man measured with the doppler-catheter flowmeter-telemetry system; The Amer. J of Med.; vol. 48; pp. 303-309; 1970.

Benchimol et al.; Bidirectional blood flow velocity in the cardiac chambers and great vessels studied with the doppler ultrasonic flowmeter; The Amer. J of Med.; vol. 52; pp. 467-473; 1972.

Bossert et al.; Swan-Ganz catheter-induced severe complications in cardiac surgery: right ventricular perforation, knotting, and rupture of a pulmonary artery; J. Car. Surg.; vol. 21; No. 3; pp. 292-295; May/Jun. 2006.

Hellerstein et al.; Recording of intracavity potentials through a single lumen, saline filled cardiac catheter; P.S.E.B.M.,; vol. 71; pp. 58-60; 1949.

Kalmanson et al.; Letter to the Editor; "Directional vs bidirectional doppler velocimeter"; Am. Heart J.; vol. 83; No. 3; pp. 437; Mar. 1972.

Lewis et al.; A Study of Normal and abnormal femoral venous flow velocity using a directional doppler; Br. J. Surg: vol. 59, No. 4; pp. 303; Apr. 1972.

Stas et al.; Peroperative intranasal electrographic control of catheter tip position in access ports placed by venous cut-down technique;EJSO; vol. 27; pp. 316-320; 2001.

Brunner, Eberhard; Ultrasound system considerations and their impact on front-end components; Analog Devices, Inc.; pp. 1-19; May-Jun. 2002.

Hellerstein et al.; Recording of intracavity potentials through a single lumen, saline filled cardiac catheter; P.S.E.B.M.; vol. 71; pp. 58-60; Apr. 5, 1949.

\* cited by examiner

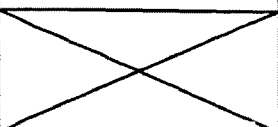

GUIDED VASCULAR ACCESS DEVICES

| Feature | Catheter | Stylet/Guidewire |
|---|---|---|
| Centering | Basket | J-tip hockey stick |
| | Bent / pre-form curve | |
| Minimize crossing profile/ maximize sensor(s) size | Recessed wall mount | Pre-formed hockey stick |
| Therapy delivery | Conventional open ended | |
| | Closed end w/ slits, valves and/or ports | |
| Preferred sensor orientation for directional data acquisition | Tip mounted/forward looking | Forward looking |
| | Side mounted/lateral looking | Rearward looking |
| | Multiple sensors/ location | Combination |
| | Steerability/Torque Control | |
| Maximize ultrasound sample volume/ divergent beam | Acoustic lens assemblies | |
| | Shaped epoxy lens assemblies | |
| | Microlens or array | |
| | Machined crystal(s) | |
| Number and shape of sensors | One crystal | |
| | Multiple crystals | |
| | Rectangular | |
| | Rounded | |
| | Other conventional crystal shapes | |
| Sensor material | piezoelectric crystals (e.g.quartz); piezoelectric ceramics (e.g. lead zirconate titanate); silicon; piezoelectric film (e.g., PVDF) | |
| Lens material | Epoxy toughened with varying weight fractions of polymethyl methacrylate (PMMA) and polycarbonate (PC), Araldite (Gy508/Hy956, Ciba), EPO-TEK 353 ND (Epoxy Technology), or Rexolite (Curbell Plastics) | |
| Non-flushing sensor | Sensor(s) encapsulated in airtight and ultrasound transparent epoxy or other sealant as part of lens assembly or sealing assembly or both | |

*FIG. 5*

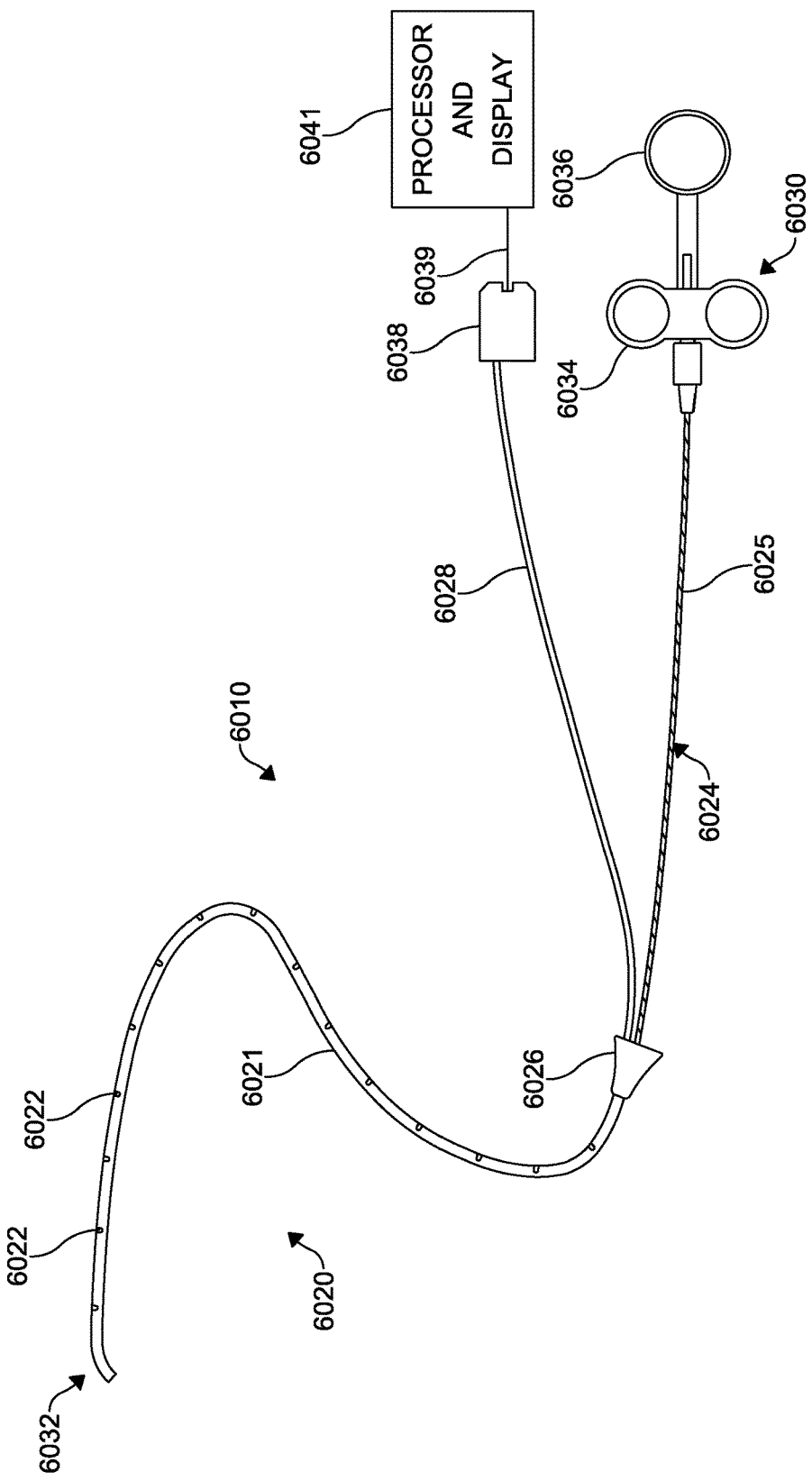

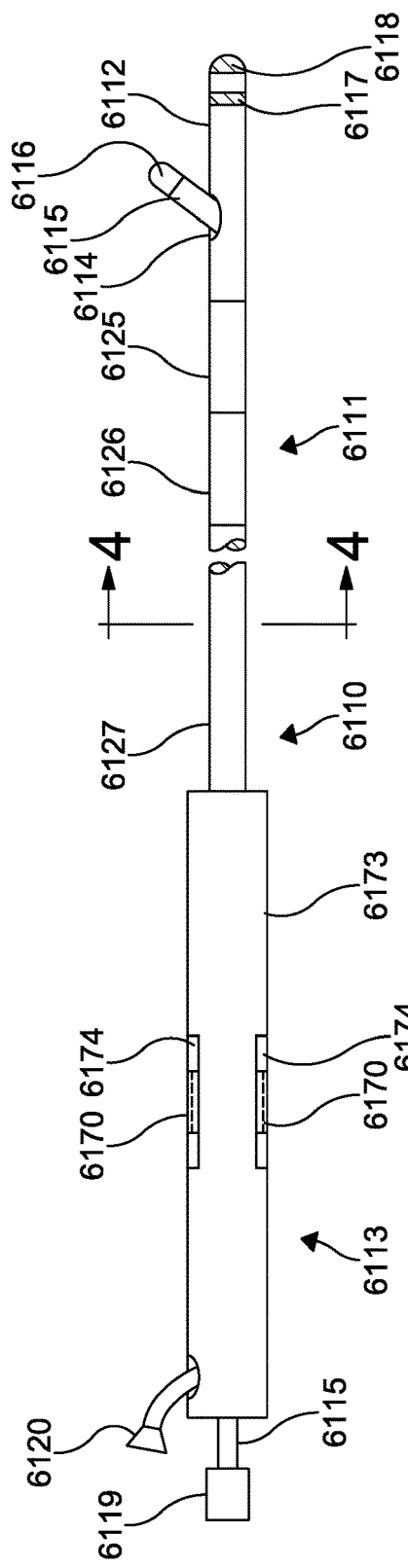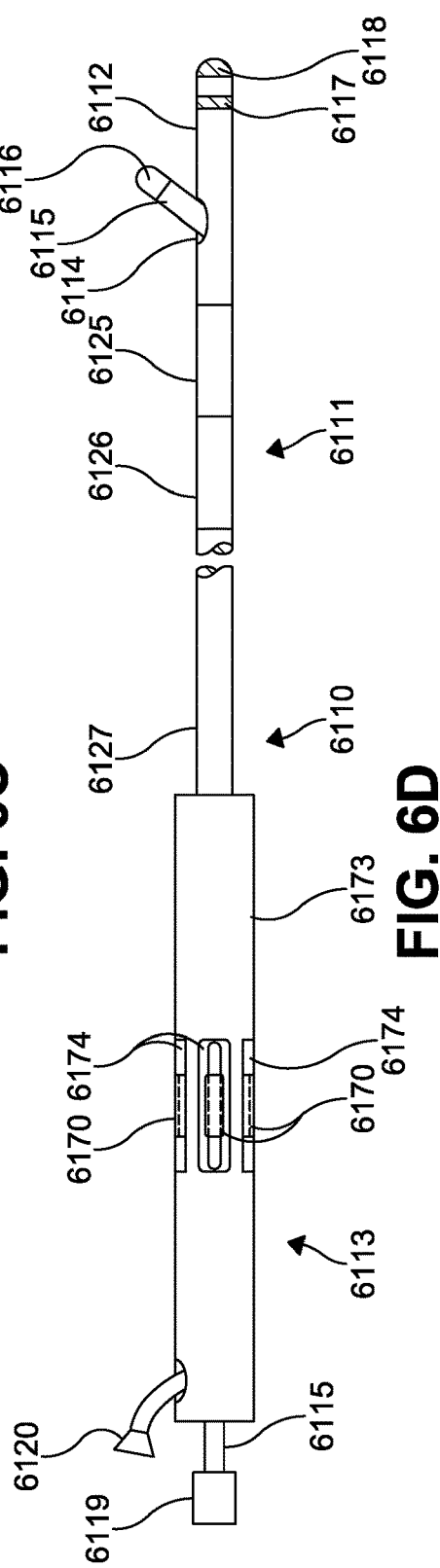

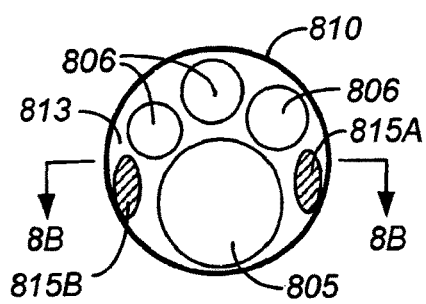
FIG. 8A
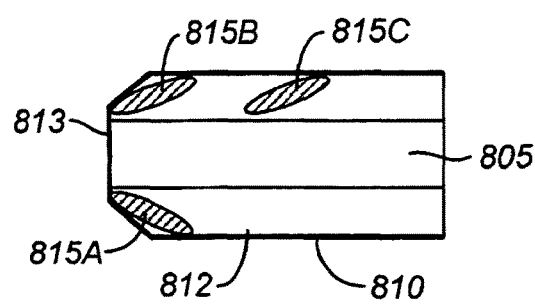
FIG. 8B
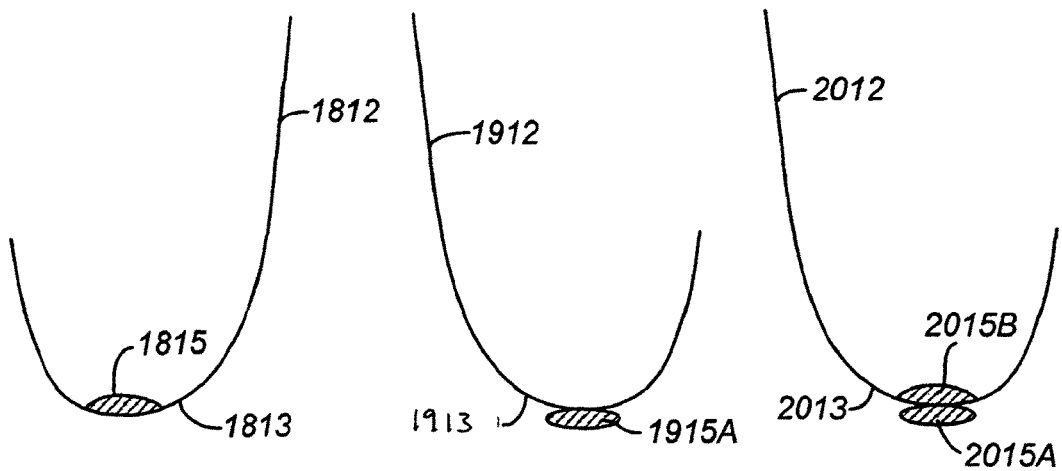
FIG. 18A  FIG. 19A  FIG. 20

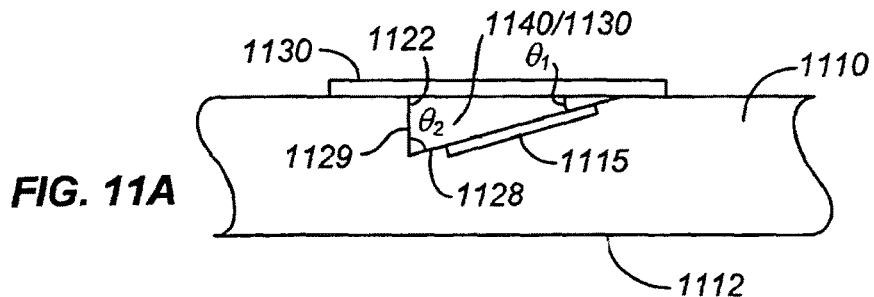
FIG. 11A
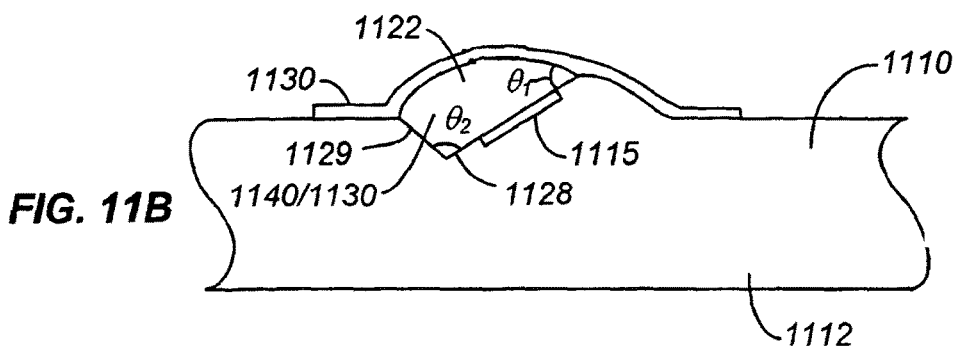
FIG. 11B
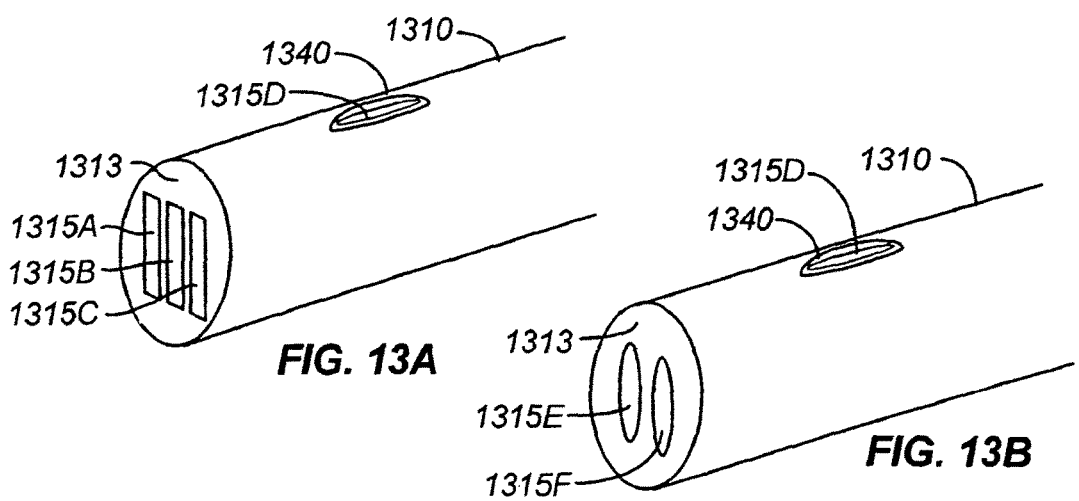
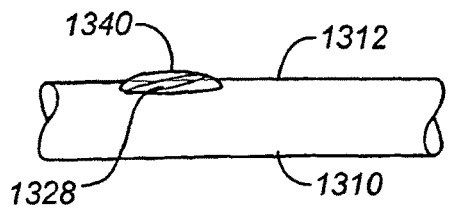
FIG. 13C
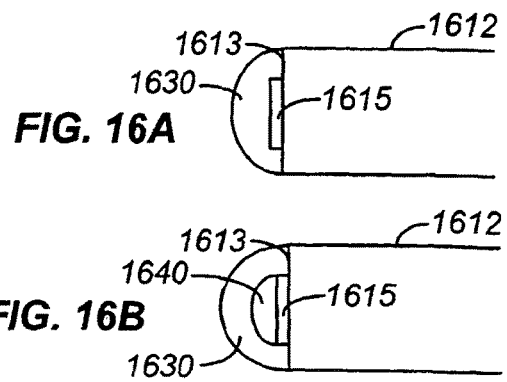

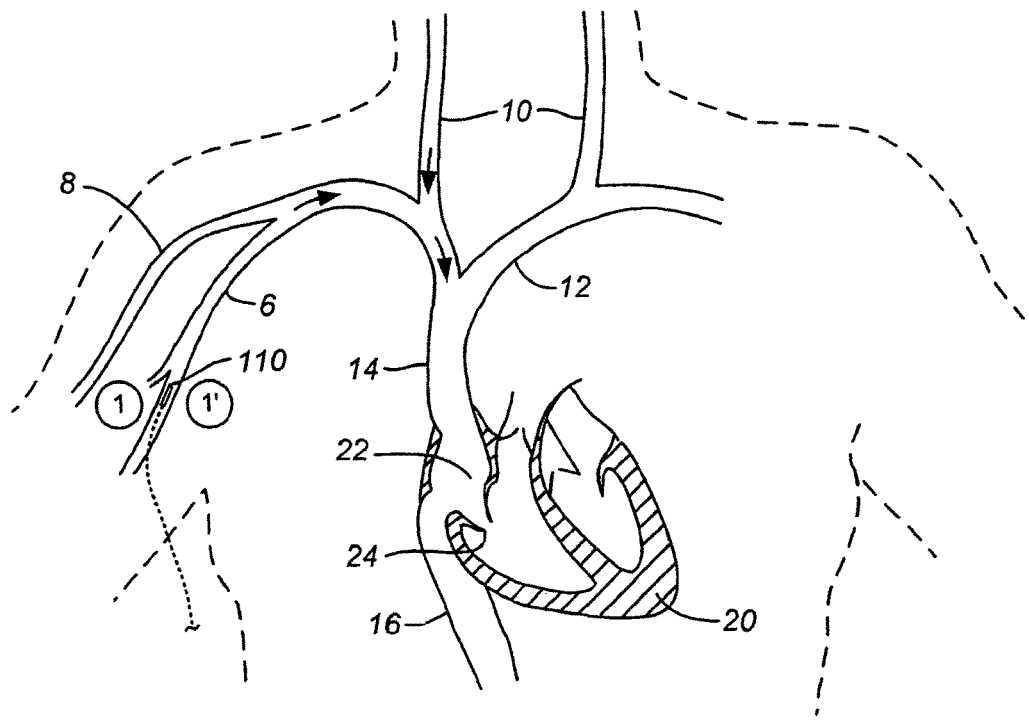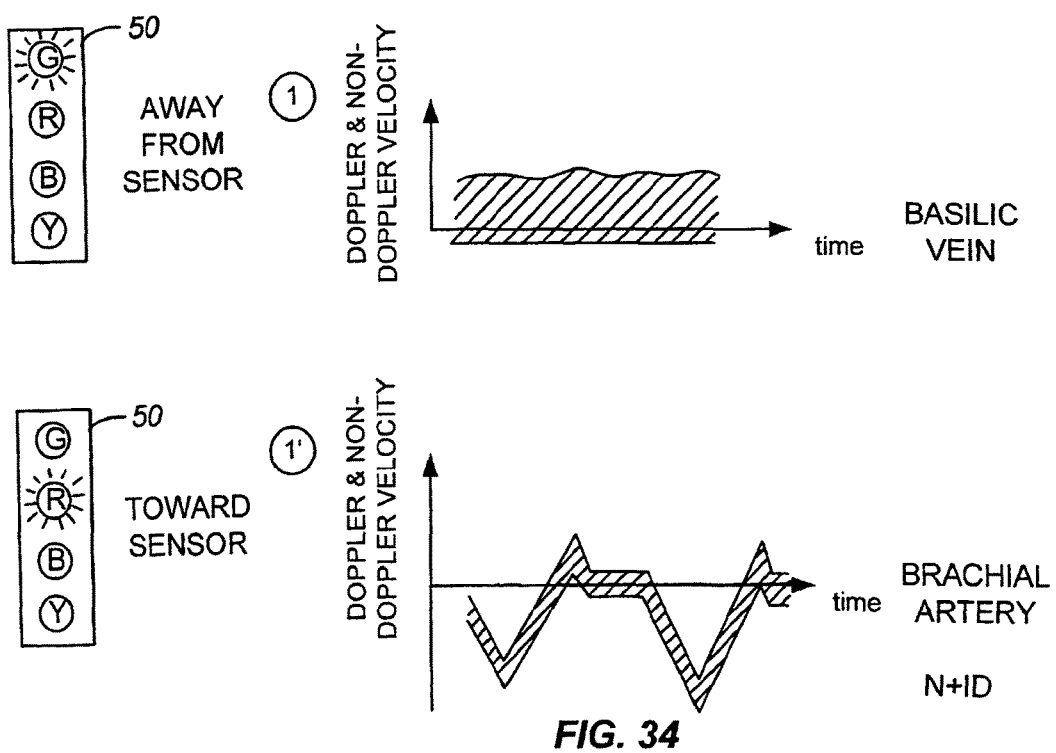
FIG. 34

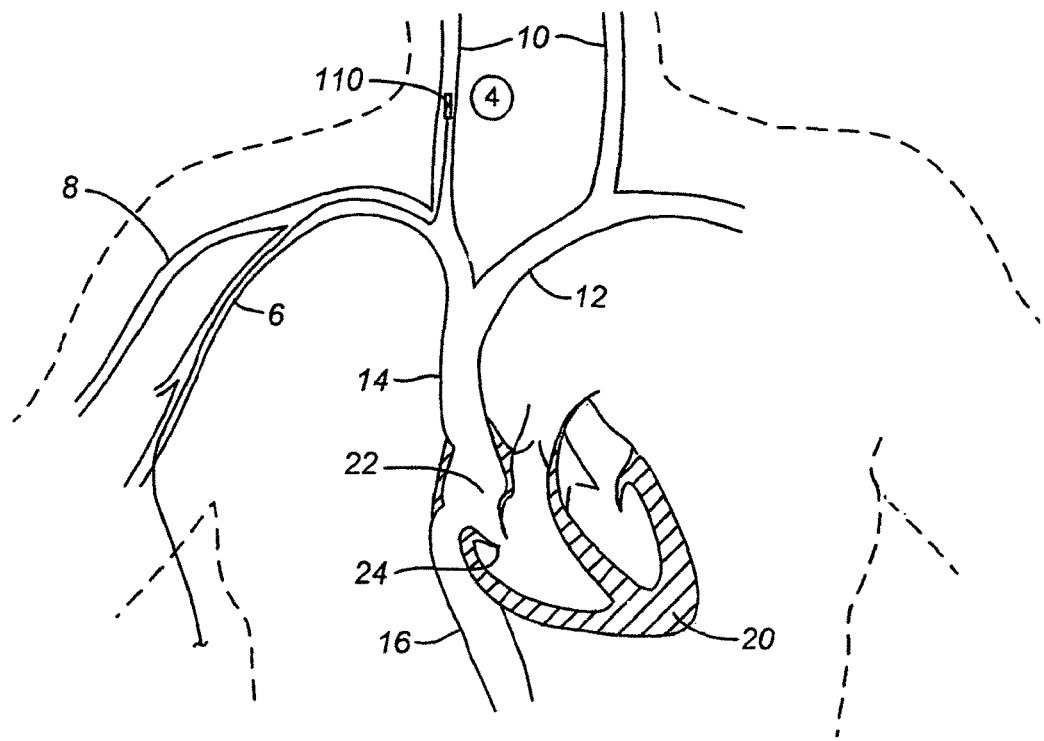
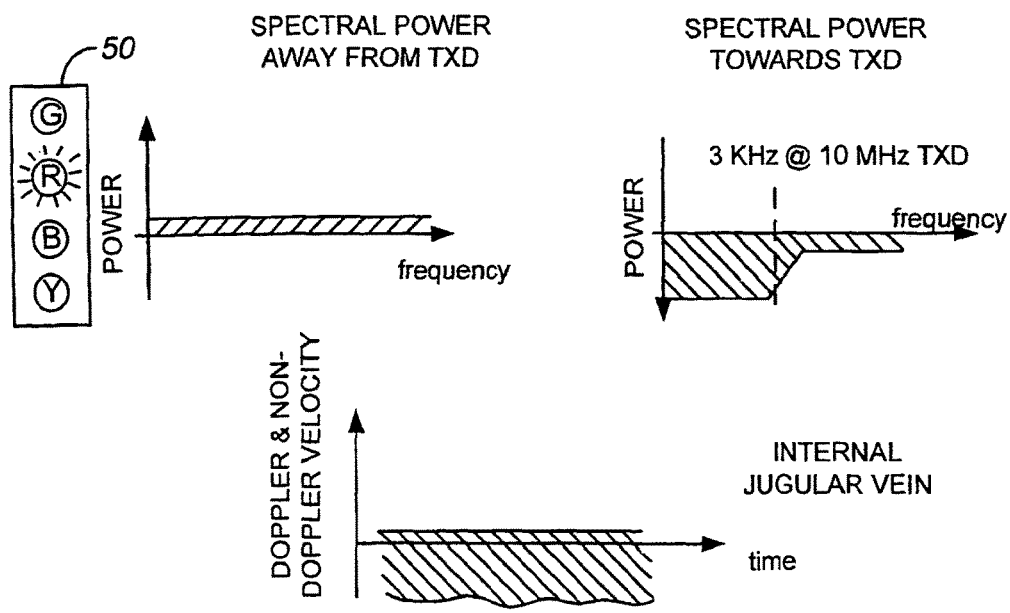
FIG. 37

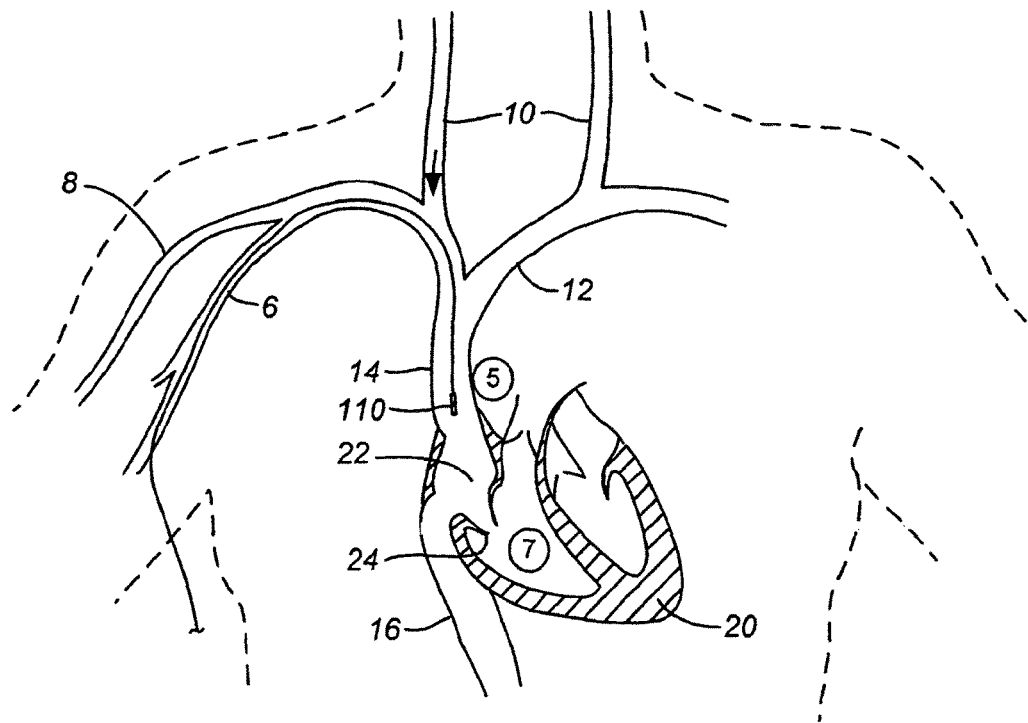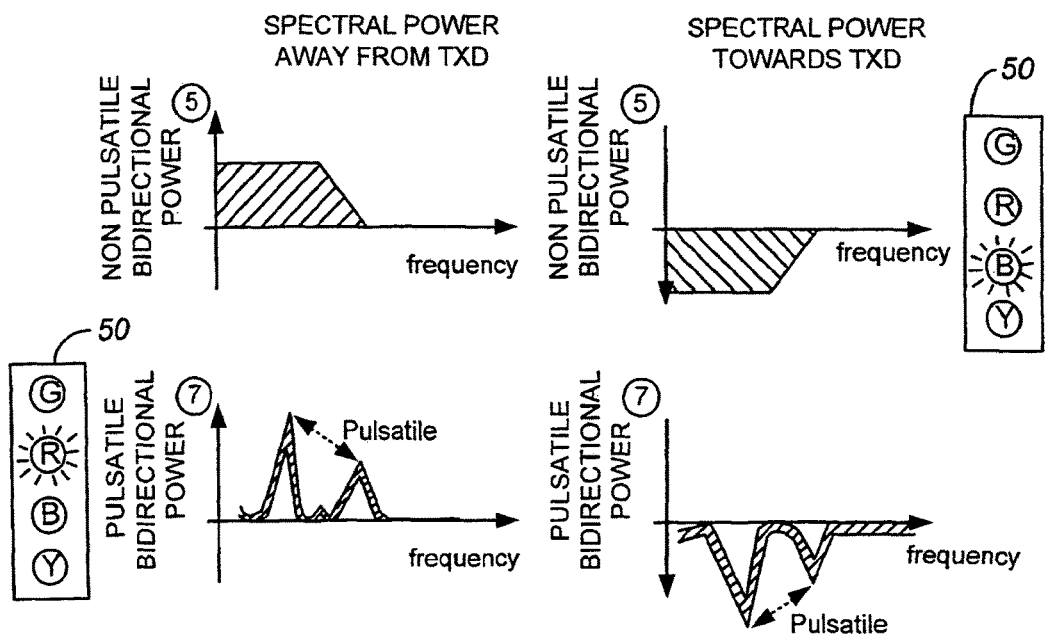
FIG. 39

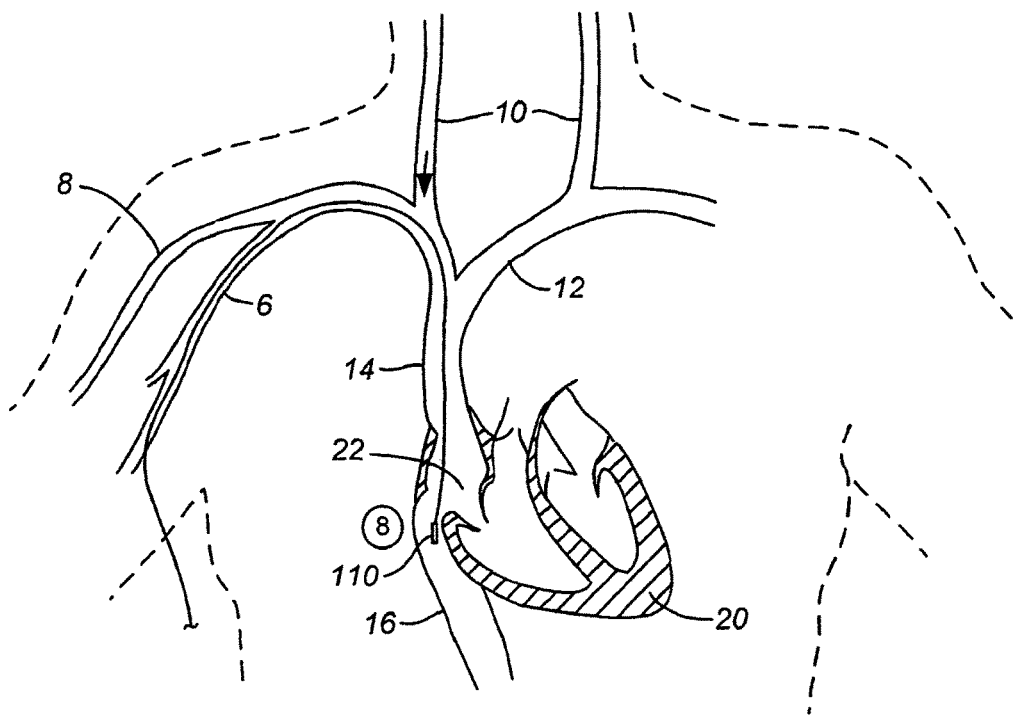
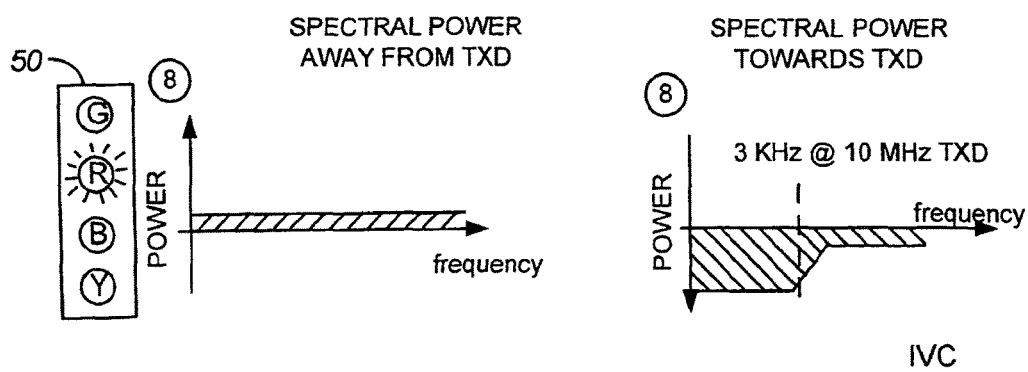
FIG. 40

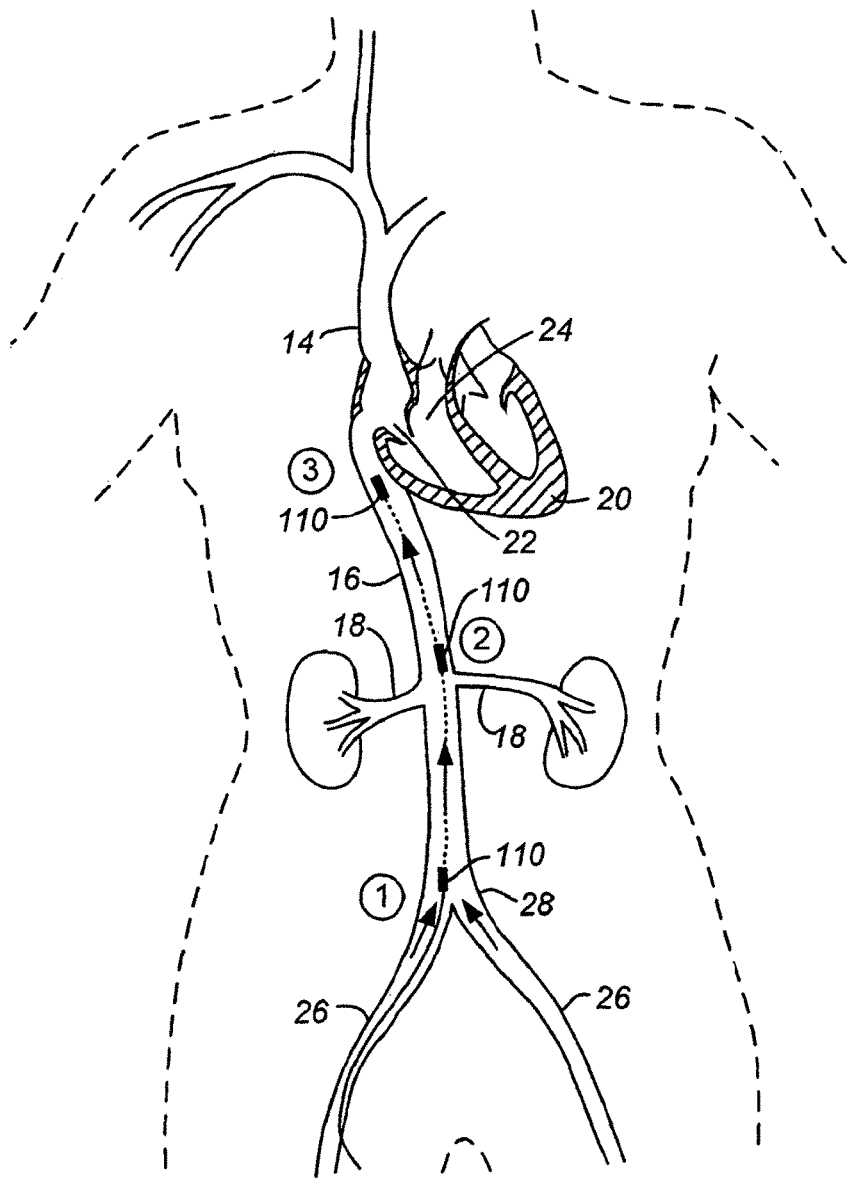
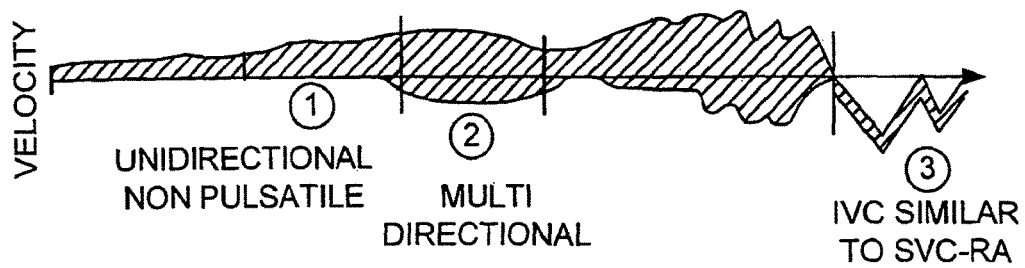
FIG. 41

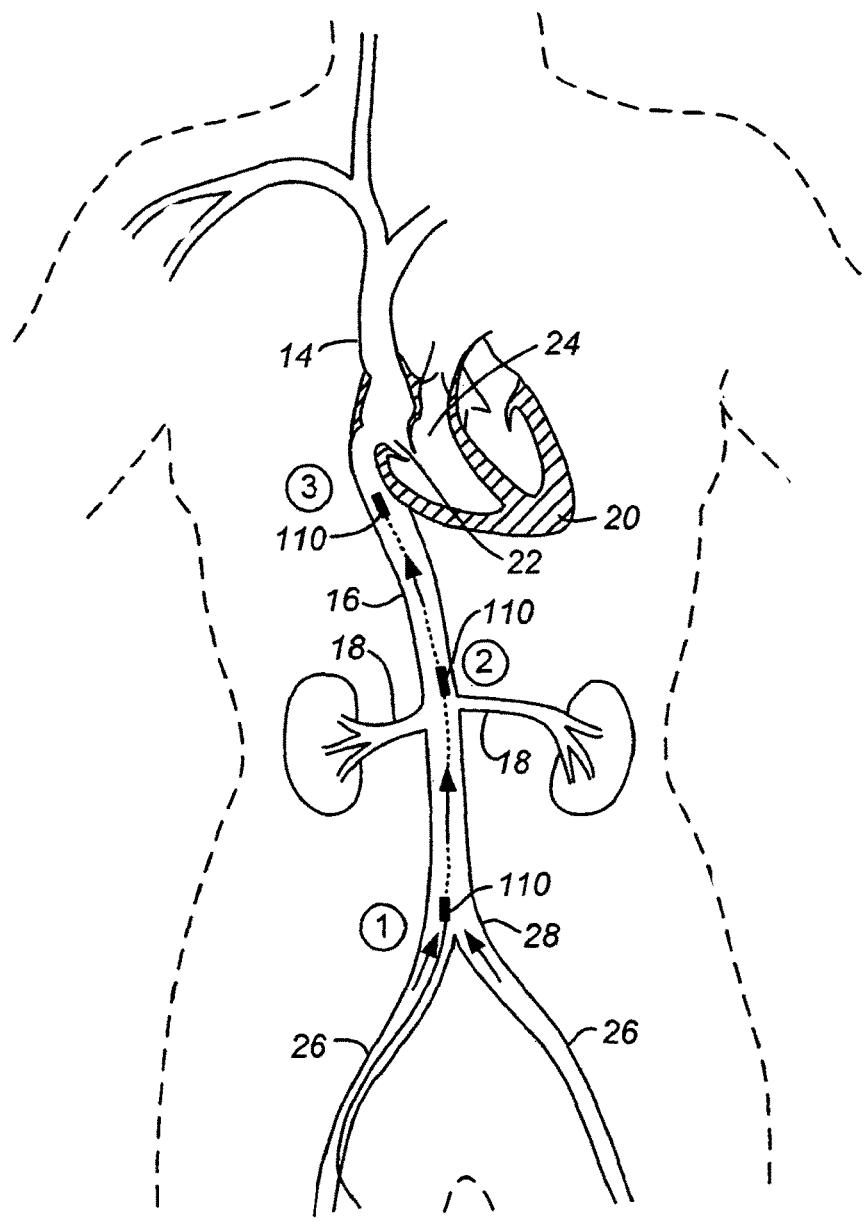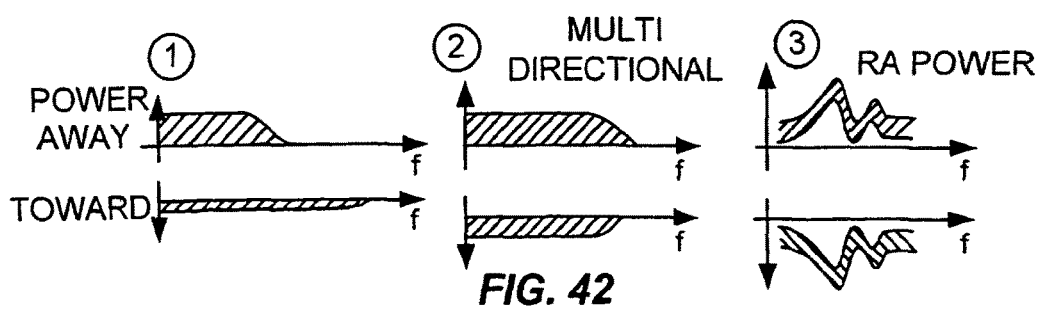
FIG. 42

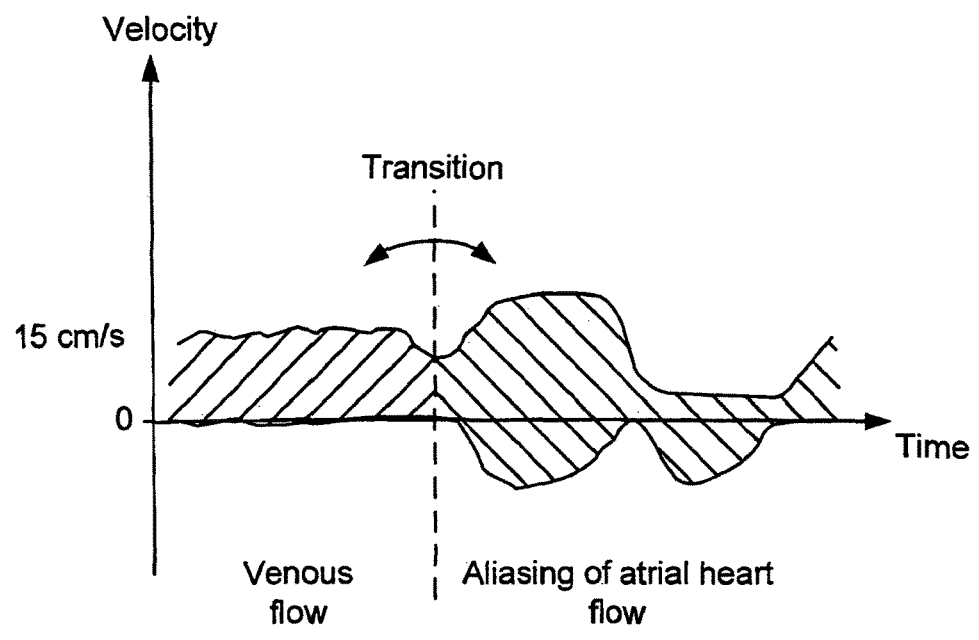
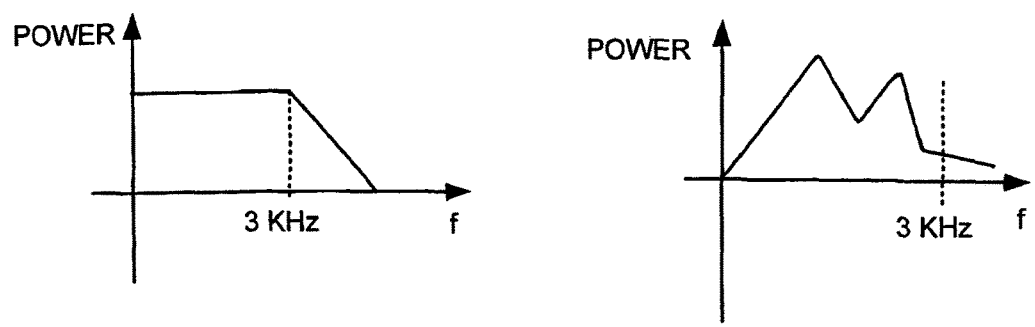
FIG. 45

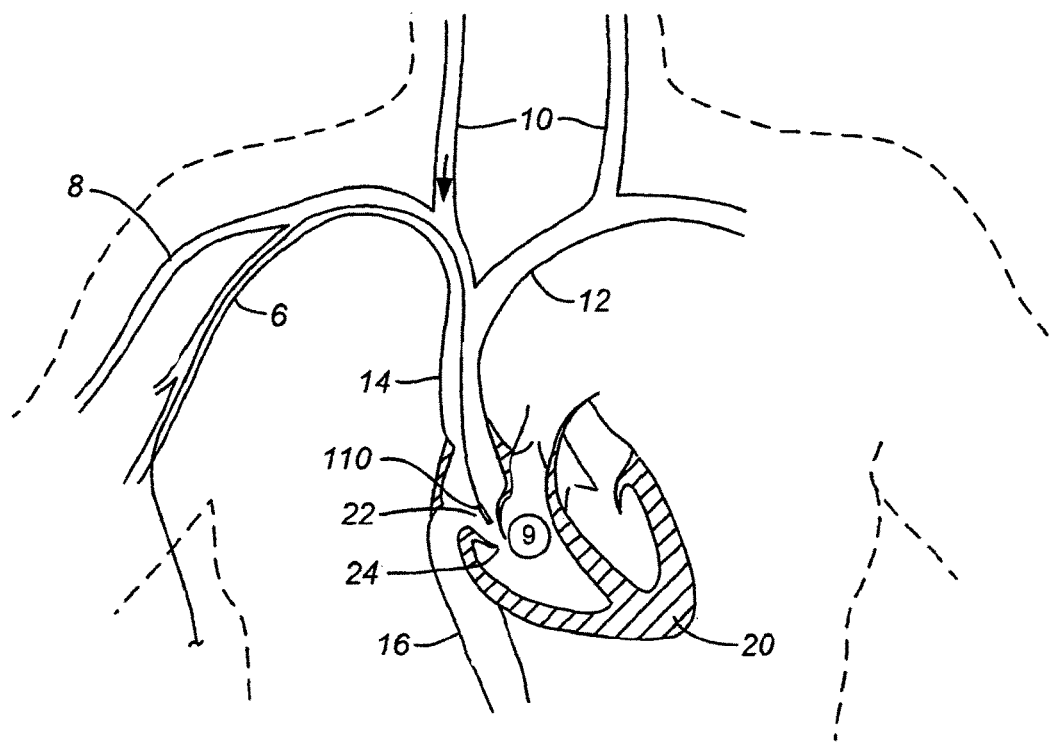
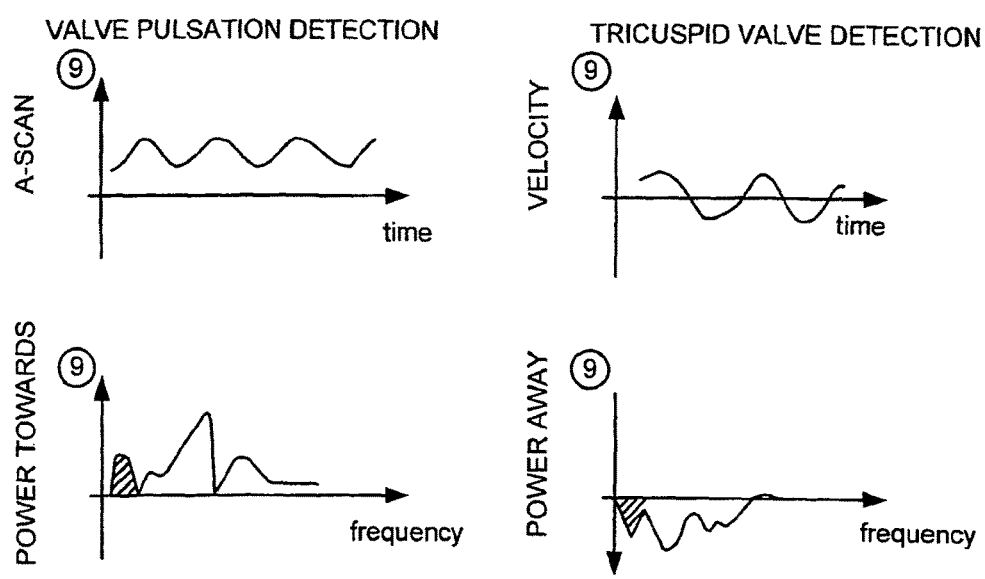
FIG. 46

ENDOVASCULAR NAVIGATION SYSTEM AND METHOD

CROSS-REFERENCE TO RELATED APPLICATIONS

This application is a continuation application of U.S. patent application Ser. No. 11/431,118, filed May 8, 2006, which claims the benefit of U.S. Provisional Patent Application No. 60/678,209, filed May 6, 2005, and of U.S. Provisional Patent Application No. 60/682,002, filed May 18, 2005, each of which is incorporated herein by reference in its entirety.

BACKGROUND OF THE INVENTION

The invention relates to the guidance, positioning and placement confirmation of intravascular devices, such as catheters, stylets, guidewires and other elongate bodies that are typically inserted percutaneously into the venous or arterial vasculature, including flexible elongate bodies. Currently these goals are achieved using x-ray imaging and in some cases ultrasound imaging. This invention provides a method to substantially reduce the need for imaging related to placing an intravascular catheter or other device. Reduced imaging needs also reduce the amount of radiation that patients are subjected to, reduce the time required for the procedure, and decrease the cost of the procedure by reducing the time needed in the radiology department.

The vasculature of mammals has long been accessed to provide therapy, administer pharmacological agents and meet other clinical needs. Numerous procedures exist in both venous and arterial systems and are selected based on patient need. One challenge common to all vascular-based therapies is health care provider access to the specific location or section of the vascular tree.

One common venous access procedure is central venous access. Central venous access is the placement of a venous catheter in a vein that leads directly to the heart. Central venous catheters are ubiquitous in modern hospital and ambulatory medicine, with up to 8 million insertions per year in the U.S. and a similar number outside the U.S.

Venous access devices are most often used for the following purposes:

Administration of medications, such as antibiotics, chemotherapy drugs, and other IV drugs Administration of fluids and nutritional compounds (hyperalimentation)

Transfusion of blood products

Hemodialysis

Multiple blood draws for diagnostic testing.

Central venous access devices are small, flexible tubes placed in large veins for people who require frequent access to their bloodstream. The devices typically remain in place for long periods: week, months, or even longer.

Central venous access devices are usually inserted in 1 of 3 ways:

a) Directly via a catheter. Catheters are inserted by tunneling under the skin into either the subclavian vein (located beneath the collarbone) or into the internal jugular vein (located in the neck). The part of the catheter where medications are administered or blood drawn remains outside of the skin.

b) Through a port. Unlike catheters, which exit from the skin, ports are placed completely below the skin. With a port, a raised disk about the size of a quarter or half dollar is felt underneath the skin. Blood is drawn or medication delivered by placing a tiny needle through the overlying skin into the port or reservoir.

c) Indirectly via a periphal vein. Peripherally inserted central catheter (PICC) lines, unlike central catheters and ports, are not inserted directly into the central vein. A PICC line is inserted into a large vein in the arm and advanced forward into the larger subclavian vein.

Central catheters and ports are usually inserted by a surgeon or surgical assistant in a surgical suite. An alternative is placement under the guidance of a special x-ray machine so that the person inserting the line can make sure that the line is placed properly. A PICC line can be put in at bedside, usually by a specially trained nurse. In this later case, confirmation by X-ray is currently required for assessing the success of the PICC placement.

Traditional surgically placed central catheters are increasingly being replaced by peripherally inserted central venous access devices. PICC lines usually cause fewer severe complications than central venous access devices. Peripherally-Inserted-Central-Catheter (PICC) is used in a variety of clinical procedures. The PICC line placement procedure is performed by interventional radiologists to deliver long-term drug delivery, chemotherapy procedures, delivery of intravenous medications or intravenous nutrition (hyperalimentation) and taking blood samples via a Hickman catheter. Insertion of PICC lines is a routine procedure in that it is carried out fairly often for a variety of treatments, and more than once in the same patient when the catheter is to be left in place for any length of time. Even though it is routine, it is a very time and labor-intensive procedure for the hospital staff, which also makes it expensive. During the procedure the physician or nurse places the catheter into a superficial arm vein such as the cephalic, basilic, antecubital, median cubital, or other superficial vein with the goal of having the distal end of the catheter reach the superior vena cava. After entering the superficial vein around the area where the arm bends (elbow), the catheter is advanced up the subclavian vein, then the brachiocephalic vein and finally it enters the superior vena cava. One caveat is to make sure that the PICC line does not enter the jugular vein via the subclavian vein.

Hemodialysis therapy via a hemodialysis catheter is another example of a procedure requiring central venous access. A dialysis catheter is a specialized type of central venous catheter used for dialysis. Dialysis catheter placement involves the insertion of a catheter into a large vessel, utilizing X-ray guidance. The challenges of inserting a hemodialysis catheter in terms of guidance and positioning are similar to those of a central venous catheter, only they are typically larger and require a peel-away sheath for insertion.

Another therapy achieved via providing access to the venous system is the percutaneous treatment of varicose veins. Published population studies indicate that approximately 25 million people in the U.S. and 40 million people in Western Europe suffer from symptomatic venous reflux disease. Percutaneous treatment of varicose veins involves the placement of an energy delivery catheter (laser or RF) after navigation the vasculature to locate the treatment site. One common treatment site is the sapheno-femoral junction and less common sites are the sapheno-popliteal junction and sites of perforator veins, which connect the superficial venous system to the deep venous system of the leg at a variety of different locations, mostly below the knee. As such, in the case of percutaneous treatment of varicose veins using specific venous junctions, the position the laser or the RF catheter at an optimal location with respect to the venous junction is critical for the success of the intervention. Currently X-ray or ultrasound imaging or both are used for such positioning.

In addition to guiding the catheter through the vasculature, the location of the catheter tip is very important to the success of the procedure. Catheters will generally function equally well for pressure measurement and fluid infusion if the tip is situated in any major vein, above or below the heart. For dialysis or the infusion of irritant/hypertonic fluids, a high rate of blood flow past the catheter tip is desirable and this requires the placement of the luminal opening in as large a vessel as possible. However, the package inserts of many central venous catheters give very strong warnings about the absolute requirement for catheter tips to lie outside the heart to avoid perforation and subsequent pericardial tamponade. Likewise positioning the catheter tip away from small peripheral veins is important to avoid damaging the vein wall or occluding the vein due the caustic effects of the infusing solution. It is also of major interest that the catheter tip stays in place after placement for the whole duration of the treatment. If the catheter tip moves, not only its effectiveness diminished but, in some situations, it can perforate the heart. In the USA, the Food and Drug Administration has issued advice emphasizing this point. Typically, the interventional radiologist uses a fluoroscopic agent to delineate the veins in the body and subsequently verifies the correct positioning of the catheter tip using a post-operative X-ray. Currently, post-operative X-ray is performed routinely while some studies have shown that only 1.5% of the cases are subject to complications that would indeed require X-ray imaging.

What is needed are methods and apparatuses to optimize guidance and placement of catheters in order to reduce the risk associated with wrong placement and the cost associated with the X-ray imaging. Further there remains a need for a catheter guidance and placement system that may be used to safely guide and place catheters in healthcare provider or clinical environments other than in the radiology department or surgical suite wherein a radiological or other external imaging modality is used to confirm catheter placement. As such, there remains a need in the medical arts for instruments, systems and associated methods for locating, guiding and placing catheters and other instruments into the vasculature generally. In addition remains a need in the medical arts for instruments, systems and associated methods for locating, guiding and placing catheters and other instruments into the vasculature to meet the challenges presented by the unique characteristics and attributes specific to the vascular system of interest.

SUMMARY OF THE INVENTION

An aspect of the invention includes an endovenous access and guidance system. The system comprises: an elongate flexible member adapted and configured to access the venous vasculature of a patient; a sensor disposed at a distal end of the elongate flexible member and configured to provide in vivo non-image based ultrasound information of the venous vasculature of the patient; a processor configured to receive and process in vivo non-image based ultrasound information of the venous vasculature of the patient provided by the sensor and to provide position information regarding the position of the distal end of the elongate flexible member within the venous vasculature of the patient; and an output device adapted to output the position information from the processor. In some embodiments, the elongate flexible member is further adapted to provide a catheter, a guidewire, and/or a stylet. In other embodiments, the device is adapted to deliver therapy to a patient, or provide venous access for another device. In still another embodiment, the system is adapted to further comprise a sensor attachment mechanism adapted to removably detach the sensor from the elongate flexible member while the elongate flexible member remains in the vasculature of the patient. In yet another embodiment, the system is configured such that the processor processes in vivo non-image based ultrasound information of the vasculature system of the patient provided by the sensor to indicate in the output information the proximity of the sensor to a structure within the vasculature of the patient. In still other embodiments, the processor can be further configured to process in vivo non-image based ultrasound information of the vasculature system of the patient to indicate in the output information movement of the elongate flexible member in a desired direction within the vasculature of the patient. Alternatively, the processor is further configured to process in vivo non-image based ultrasound information of the vasculature system of the patient based on a parameter selected from a group consisting of: a venous blood flow direction, a venous blood flow velocity, a venous blood flow signature pattern, a pressure signature pattern, A-mode information and a preferential non-random direction of flow. In another aspect of the invention, the system further comprises a divergent lens associated with the sensor, or a plurality of lenses associated with the sensor. The divergent lens can be adapted to attach the sensor to the elongate flexible member. The sensor may be further configured such that it is a first sensor adapted to transmit an ultrasound signal, the system further comprising a second sensor adapted to receive non-image based ultrasound information. Additionally, a sensor drive mechanism adapted drive the sensor in a plurality of ultrasound transmission modes can be provided. In some embodiments, the sensor is a first sensor, the system further comprising a second sensor disposed at the distal end of the elongate flexible member and configured to provide in vivo non-image based ultrasound information of the venous vasculature of the patient to the processor. In other embodiments, a centering element adapted to substantially center the distal end of the elongate member within a vessel. In some instances, two or more additional sensors wherein the sensor and the two or more additional sensors are attached to the elongate flexible member in an arrangement that mimics an endovascular junction. Additionally, a steering element for directing the device tip in response to feedback information derived from the acquired data. Further embodiments can include a torque control element for directing the device tip in response to feedback information derived from the acquired data.

According to another aspect of the invention, an endovascular access and guidance system, comprising: an elongate flexible member adapted and configured to access the vasculature of a patient; a sensor and an associated divergent lens disposed at a distal end of the elongate flexible member and configured to provide in vivo non-image based ultrasound information of the venous vasculature of the patient; a processor configured to receive and process in vivo non-image based ultrasound information of the venous vasculature of the patient provided by the sensor and to provide position information regarding the position of the distal end of the elongate flexible member within the venous vasculature of the patient; and an output device adapted to output the position information from the processor is provided. The elongate flexible member can be adapted to comprise a catheter, a guidewire, or a stylet. In some embodiments, the system can further be adapted such that the elongate flexible member is adapted to deliver a therapy to the patient and/or provides endovascular access for another device. In still other embodiments, a sensor attachment mechanism adapted to removably detach the sensor from the elongate flexible member while the elongate flexible member remains in the vasculature of the patient. Some embodiments of the system can be adapted such that the processor is further configured to process in vivo non-image based ultrasound information of the vasculature system of the patient provided by the sensor to indicate in the output information the proximity of the sensor to a structure within the vasculature of the patient. In some instances, the processor is further configured to process in vivo non-image based ultrasound information of the vasculature system of the patient to indicate in the output information movement of the elongate flexible member in a desired direction within the vasculature of the patient. In other instances, the processor is further configured to process in vivo non-image based ultrasound information of the vasculature system of the patient to indicate in the output information the proximity of the sensor to a structure within the vasculature of the patient. In still other instances, the processor is further configured to process in vivo non-image based ultrasound information of the vasculature system of the patient based on a parameter selected from a group consisting of a blood flow direction, a blood flow velocity, a blood flow signature pattern, a pressure signature pattern, A-mode information and a preferential non-random direction of flow. The divergent lens can be adapted in some embodiments to attach the sensor to the elongate flexible member. In other embodiments, the sensor is a first sensor adapted to transmit an ultrasound signal, the system further comprising a second sensor adapted to receive non-image based ultrasound information. In still other embodiments, the sensor is a first sensor adapted to receive non-image based ultrasound information, the system further comprising a second sensor adapted to transmit an ultrasound signal. The system can also be adapted such that it comprises a sensor drive mechanism adapted drive the sensor in a plurality of ultrasound transmission modes. In some embodiments, the sensor is a first sensor, the system further comprising a second sensor disposed at the distal end of the elongate flexible member and configured to provide in vivo non-image based ultrasound information of the venous vasculature of the patient to the processor. In other embodiments, the endovascular access and guidance system is adapted to further comprise a centering element adapted to substantially center the distal end of the elongate member within a vessel. The system can further comprise a steering element for directing the device tip in response to feedback information derived from the acquired data. In other embodiments, the system can be adapted to further comprise a torque control element for directing the device tip in response to feedback information derived from the acquired data. In still other embodiments, the system comprises a plurality of lenses associated with the sensor.

Another aspect of the invention includes an ultrasound sensor assembly comprising: an ultrasound sensor; and an airtight and ultrasound transparent seal encapsulating at least one side of the ultrasound sensor. The sensor assembly can be configured to include an airtight and ultrasound transparent seal shaped into an acoustic lens. Further, the acoustic lens can be adapted to be shaped to spread a beam generated by the ultrasound sensor. In some embodiments, the lens is made from epoxy. Other embodiments of the invention include an ultrasound sensor formed from a piezoelectric crystal, a piezoelectric ceramic, silicon, and/or a thin piezoelectric film. The lens of the system, in some embodiments, comprises a plurality of microlenses. In another aspect of the invention, the ultrasound sensor is attached to the catheter to provide a forward looking beam, and/or a lateral looking beam. In other embodiments, the ultrasound sensor is disposed in a recess formed in a wall of the catheter. The ultrasound sensor can, in some embodiments, be adapted to provide Doppler readings from a fluid passing over the external surface of the catheter. In some aspects of the invention an airtight and ultrasound transparent seal is shaped into an acoustic lens is provided. The acoustic lens is shaped, in some embodiments, to spread the beam generated by the ultrasound sensor.

Still another aspect of the invention includes a method for positioning an instrument in the venous system of a body. The method comprises the steps of: accessing the venous system of the body; positioning an instrument in the venous system of the body; using the instrument to transmit an ultrasound signal into the venous system of the body; using the instrument to receive a reflected ultrasound signal from the vasculature indicating flow rates between 2 and 20 cm/s; processing the reflected ultrasound signal to determine one or more parameters from a group consisting of: a venous blood flow direction, a venous blood flow velocity, a venous blood flow signature pattern, a pressure signature pattern, A-mode information and a preferential non-random direction of flow; and advancing the instrument within the vasculature using the one or more of the determined parameter or parameters within the vasculature. Using the instrument to transmit an ultrasound signal into the vasculature of the body comprises, in some aspects of the invention, transmitting or receiving an A mode ultrasound signal into or from the vasculature of the body. In some embodiments, using the instrument to transmit an ultrasound signal into the vasculature of the body comprises transmitting or receiving Doppler ultrasound signal into or from the vasculature of the body. In other embodiments, using the instrument to transmit an ultrasound signal into the vasculature of the body comprises transmitting or receiving a non-imaging target tracking ultrasound signal into or from the vasculature of the body. In some embodiments, processing the reflected ultrasound signal to determine a flow pattern determines a flow direction within the vasculature towards the instrument and further comprises processing the reflected ultrasound signal to determine a flow pattern determines a flow direction away from the instrument. In other embodiments, the reflected ultrasound signal is processed to determine the presence of a signal indicating a specific blood flow pattern. In still other embodiments, processing the reflected ultrasound signal is performed to determine the presence of a signal indicating a specific pressure pattern. In yet other embodiments, processing the reflected ultrasound signal to determine the position of the instrument relative to the caval-atrial junction is performed. Other aspects of the invention can include processing the reflected ultrasound signal to determine the presence of flow after processing the reflected ultrasound signal to determine the presence of both antegrade and retrograde flow. Still other aspects can further comprise processing the reflected ultrasound signal to determine the presence of flow away from the instrument and after processing the reflected ultrasound signal to determine the presence of flow both away and towards the instrument. In some embodiments of the method, the method comprises processing the reflected ultrasound signal to determine the presence of a signal indicating a specific structure. In other aspects of the invention, the specific target vasculature for positioning an instrument is included, for example, the specific structure is a valve of a heart, a blood vessel wall, a heart wall. In another aspect of the invention, the method further comprises processing the reflected ultrasound signal to determine the presence of a signal indicating a position where two or more vessels join. For example, the two or more vessels can comprise a superior vena cava and an inferior vena cava, an inferior vena cava and a renal vein; a right common iliac vein and a left common iliac vein; an external iliac vein and an internal iliac vein; a right brachiocephalic vein and a left brachiocephalic vein; a superior vena cava and an azygous vein; a common femoral vein and a great saphenous vein; a superficial femoral vein and a deep femoral vein; a popliteal vein and a lesser saphenous vein; a perforator vein and a superficial vein; a perforator vein and a deep tibial vein; a great saphenous vein and a varicose vein; a jugular vein and a subclavian vein; or a cephalic vein and an axillary vein. In another aspect of the invention, the method can further comprise: using the instrument determine a location to secure a device within the vasculature of a body; and securing the device to the body to maintain the device in the location determined by the instrument. In still another aspect of the method, the method can further comprise: using the instrument to calculate the current position of the device; and determining if the device is in the location determined by the instrument by comparing the current calculated position of the device to the location determined by the instrument. In some aspects of the method, the method further comprises processing the reflected ultrasound signal to determine the position of the instrument within the right atrium relative to the coronary sinus. In still other aspects the method further comprising processing the reflected ultrasound signal to determine the position of the instrument within the left atrium relative to a pulmonary vein.

INCORPORATION BY REFERENCE

All patents, publications and patent applications mentioned in this specification are herein incorporated by reference in their entirety to the same extent as if each individual patent, publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 5 is a table that summarizes some of the features of the devices of the invention;

FIG. 6A is a plan view catheter steering system for use with steerable guided vascular access devices including an oximetric catheter.

FIG. 6C is a side view of a guiding catheter with multi-single beam ultrasound capability of the present invention with an electrophysiology catheter within the guiding catheter and two thumb slides for steering the guiding catheter;

FIG. 6D is a side view of a guiding catheter with multi-single beam ultrasound capability of the present invention with an electrophysiology catheter within the guiding catheter and four thumb slides (only three of which are shown) for steering the guiding catheter;

FIGS. 8A and 8B illustrate end and section views of a catheter based, multiple sensor, guided vascular access device;

FIGS. 11A-B illustrate an embodiment of the invention with the sensor disposed in a recess of the elongate body;

FIGS. 13A-C illustrate an embodiment of the invention in which sensors are disposed at the distal end of the catheter and one sensor is disposed on the side of the catheter;

FIGS. 16A-B illustrate the tip of a stylet, or other elongate body, in which a seal covers the sensors;

FIGS. 18A-C illustrate the use of a location device with a guidewire;

FIGS. 19A-B illustrate a sensor disposed on a convex side of a distal portion of a guidewire;

FIG. 20 illustrates sensors on both the concave and convex side of the distal portion of a bent guidewire;

FIGS. 34-42 illustrate techniques for positioning a device according to the invention within the venous system;

FIG. 45 illustrates a transition from venous flow into an aliasing of atrial flow;

FIG. 46 illustrates a representative signal detected by a system as a device according to the invention is positioned in the right atrium;

DETAILED DESCRIPTION OF THE INVENTION

Figure 1:
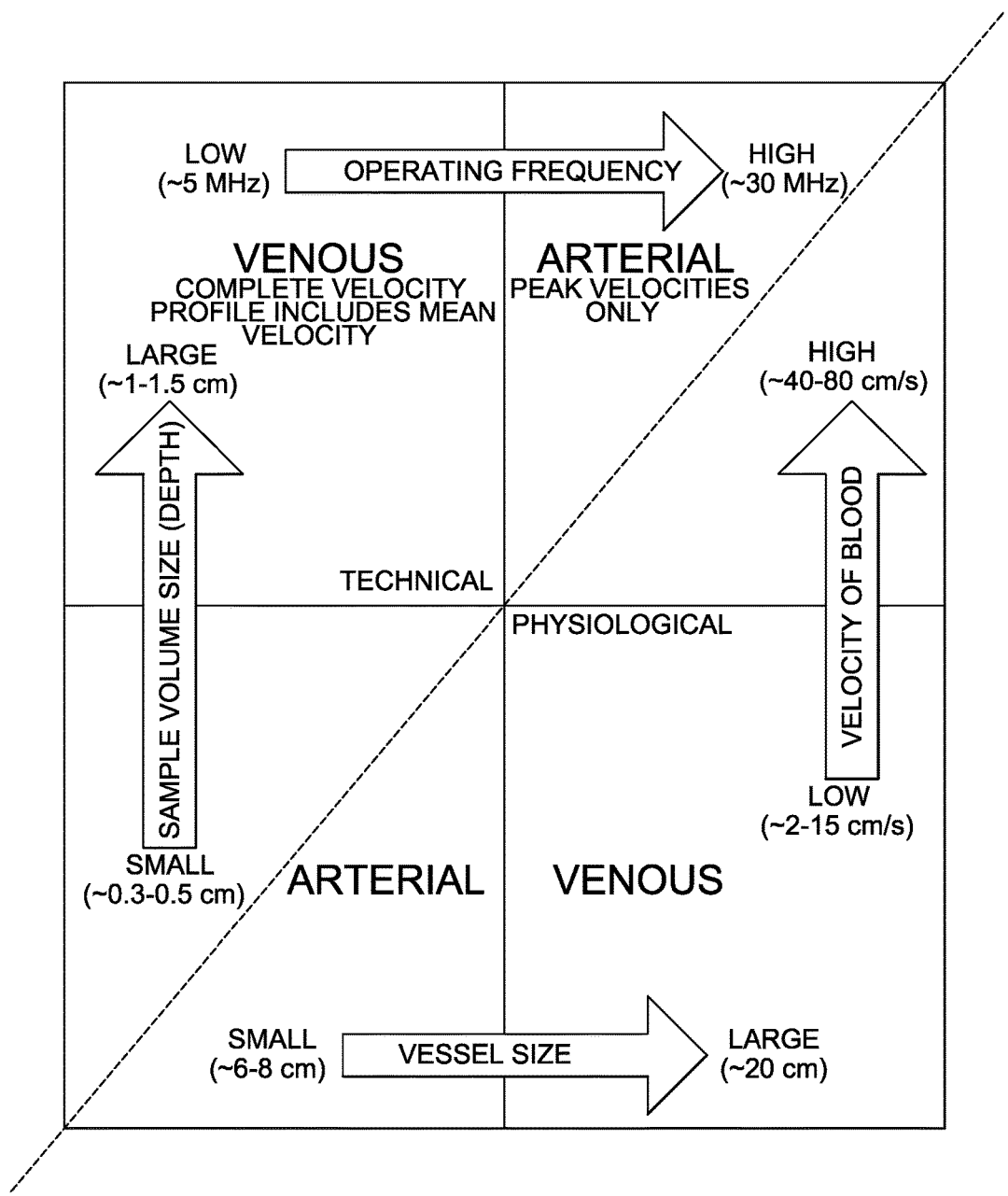
FIG. 1 is a diagram that illustrates an overview of the technical and physiological differences between the venous and arterial systems.

Embodiments of the present invention provide guided vascular access devices, systems for processing signals from the guided vascular access devices and user interface for providing information to a user based on outputs from the processing system. Other aspects of embodiments the invention relate to the use of intravascularly measured physiological parameters for locating, guiding, and placing catheters in the vasculature (see FIG. 1). In one aspect, the present invention relates to a catheter assembly with built-in sensors for measuring of physiological parameters such as blood flow, velocity, or pressure. In a different aspect, the present invention relates to data processing algorithms that can identify and recognize different locations in the vasculature based on the pattern of physiological parameters measured at that location. In a third aspect, the present invention relates to an instrument that has a user interface which shows guiding and positioning information. The fourth aspect of the present invention relates to the method of guiding and positioning a catheter within the vasculature by the user based on location information provided by the catheter itself. Other aspects of embodiments the invention relate to the use of intravascularly measured physiological parameters for locating, guiding, and placing catheters or guide wires for use as guides to particular locations within the vasculature that have been identified using the guided vascular access devices and systems described herein.

The present invention provides a new apparatus and method for intravascular guidance and placement of catheters and for monitoring their location within the vasculature based on the recognition of blood flow patterns at the locations of interest. A major benefit of the new apparatus and method introduced herein is that it increases the chances of correct placement of the devices in a procedure performed at the bedside without the need for imaging guidance, in particular without X-ray imaging. Another benefit is related to the fact that the guided vascular access devices and the systems described herein may be inserted into the existing healthcare workflow for placing instruments into the vasculature. More specifically, a new apparatus and method for intravascular guidance and placement of catheters and/or guide wires to then guide the deployment of other devices or therapies in the body such as, for example, location of heart valves for replacement heart valve procedures; identification of the renal veins and inferior vena cava for IVC filter placement; location of coronary sinus for placement of pacing leads or mitral valve modification devices; location of pulmonary veins for sensor placement and/or performance of therapy such as ablation treatment for atrial fibrillation; as well as the placement of device or performance of therapy at specific locations in the vasculature identified by the techniques described herein.

In some embodiments, the systems and methods of embodiments of the inventive guidance system described herein are utilized to locate, guide and position catheters and/or guide wires equipped with sensors described herein within the vessels of the venous system. The embodiments described herein may also be utilized in the vessels of the arterial system as well. In one aspect, the guided vascular access devices described herein may be used for the guidance, positioning, and placement confirmation of intravascular catheters used in a wide number of clinical applications. Exemplary clinical applications that would benefit from embodiments of the invention include the placement of, for example, central venous access catheters, hemodialysis catheters and the placement of catheters or therapy devices or treatment systems for percutaneous treatment of varicose veins.

The present invention is based on the ideas that: a) certain locations in the vasculature can be identified by specific blood flow patterns at those locations as quantified by blood pressure or Doppler measurements; and b) the direction of traveling of a catheter can be determined relative to the direction of blood flow by using the Doppler effect.

For example, in the case of a PICC line, by determining and real-time monitoring the direction of catheter movement in the blood vessels using the sensors, techniques, data acquisition and processing described herein, a user receives feedback on advancing a guided vascular access device to allow the PICC to advance along a desired path from the arm vein into the vena cava. The system may also recognize unintended entry into other veins because of the differences in flow patterns received from the sensors. As such, the system may recognize unintended entry into the jugular vein, the subclavian one or even if the sensor is against the vessel wall. By monitoring the data acquired from sensors positioned on the guided vascular access device, the user can be notified when the catheter tip reaches the ideal placement point next to the root of the vena cava. The system recognizes the root of the vena cava, and other vascular components, by analyzing sensor acquired data to identify unique patterns and signatures.

The technology described herein is essentially non-imaging, i.e., does not require all the elements that make imaging possible, e.g., scanning with a moving transducer or working with phased arrays and beam forming. Non-imaging ultrasound refers to the one dimensional representation of ultrasound information. In contrast, imaging ultrasound utilizes 2D or 3D ultrasound information, moving transducers, phased arrays and beam forming techniques. As such, embodiments of the present invention provide a venous ultrasound based guidance system for: endovascular characterization of venous blood flow; venous catheter guidance; endovascular characterization of slow moving anatomical targets; providing a disposable (single use) ultrasound data acquisition unit; and providing a hand-held, simple, inexpensive user interface.

Most prior art relating to the use of intravascular ultrasound for diagnostic and therapeutic purposes addresses problems on the arterial side of the vasculature where blood flow velocities are higher and artery diameters are smaller than their accompanying venous counterparts (FIG. 1.) As such, devices and data processing algorithms that are designed for the arterial circulation do not function well within the venous circulation where blood flow velocities are typically in the range of 2-15 cm/second instead of 40-80 cm/second as seen in normal arteries. Likewise, for catheter-based ultrasound devices to function within the venous circulation a lower ultrasound operating frequency of approximately 10 MHz is required and a larger sample volume size (depth) is needed than on the arterial side.

An exemplary arterial ultrasound system, such as that described by Franzin in Doppler-guided retrograde catheterization using transducer equipped guide wire (U.S. Pat. No. 5,220,924), uses a single crystal 20 MHz pulsed wave (PW) Doppler to detect peak velocities in the pulsatile flow in the arteries. Arterial measurement systems such as this system do not work for venous system (see FIG. 1) applications such as PICC insertion guidance for several reasons. One reason is that the penetration depth of such systems is inadequate. The penetration depth of ultrasound in tissue including blood is maximally about 3-5 mm at an operating frequency of 20 MHz. This penetration depth is not deep enough to measure velocities in vessels with 10-20 mm or larger inner diameters like the SVC or in other large diameter veins. Moreover, such a system with an operating frequency of 20 MHz is not capable to characterize flow and determine the caval-atrial junction which may require up to 15 mm of penetration depth. In order to be able to monitor the high peak velocities of the arterial system where blood flow of approximately 80 cm/s is expected, a parameter called pulse repetition frequency (PRF) must be relatively high, potentially higher than 100 KHz. In contrast, peak velocities of the venous system where blood flow of approximately 15 cm/s is expected, the PRF parameter can be approximately 40 KHz in order to successfully characterize such a relatively slow flow rate.

A third reason, related to PRF, involves the relatively large sample volume size needed to accurately characterize venous blood flow patterns according to the inventive processing techniques described herein. The PRF of 100 KHz required for high velocity detection produces a sample volume size on the order of only approximately 2 mm wide. Such a sample volume size is wholly inadequate for the accurate characterization of blood flow patterns in the large veins. A sample volume of approximately 15 mm is needed for the characterization of large veins and additional modifications are needed to ensure adequate penetration depth is obtained.

A fourth reason that conventional arterial ultrasound systems are not suited for the venous system monitoring techniques described herein are that arterial systems are optimized to detect the high arterial flow velocities or even just peak velocities. Using the Franzin arterial system as an example, such an arterial monitoring system would detect only the high peak velocities of the arterial flow and not the entire velocity pattern. Arterial systems are configured neither to discriminate low velocities and nor detect patterns of flow containing low velocities, e.g., venous flow.

Relevant Anatomic and Physiologic Considerations

For the placement of intravenous lines characterization of venous flow along the placement path is of importance, e.g., from the basilic and cephalic veins to the subclavian, brachial and into the superior vena cava. The internal jugular vein flow needs to also be characterized as does the inferior vena cava flow.

The superior and inferior vena cava are referred to as the "great veins" and are of special interest for central venous access applications. Their combined internal diameter at the right atrium is between 2.5 and 3 cm and their combined cross-sectional area of approximately 6 $cm^2$. The blood velocities in the great veins can reach 15 cm/sec in order to allow for a blood flow of approximately 5 L/min. These are the highest velocities on the venous side. Moving away from the heart towards the capillaries, the venous velocities decrease because the total cross-sectional area of the blood vessels increases while the amount of blood flowing is the same. In the basilica or cephalic veins the blood flows at approximately 2 to 5 cm/sec. Venous flow is non-pulsatile. The variation in velocities are small and due mainly to the mechanism of propagation helped by the locally distributed venous valves and the effect of respiration which alters blood flow velocities within the deep and central veins proportional to changes in intrathoracic and intraabdominal pressures.

In comparison, on the arterial side and in the heart blood flows at velocities around 50 cm/sec and can reach 80 cm/sec peak velocity. The mean velocities are higher in the arteries than in veins in addition to the fact that arterial flow is pulsatile with high peak velocities. The pulsatile pattern of the arterial flow follows the pulsatile pattern of the heart beats, which represent the centralized mechanism of propagation of blood through arteries.

The table below summarizes the parameters which can be used to characterize blood flow and the differences between these parameters in venous, arterial, and heart chamber flows. Because of these differences, different requirements are imposed on the technology in order to characterize venous flow vs. arterial or heart chamber flow.

TABLE 1

| Parameter | Large Veins | Large Arteries | Heart Chambers |
| --- | --- | --- | --- |
| Velocities (cm/s) | 2-15 | 40-80 | 40-80 |
| Vessel inner diameter (mm) | SVC and IVC: app. 20 Subclavian: app. 8 Internal Jugular: app. 10 | Subclavian: 6 Femoral: 8 | N/A |
| Flow pattern | Non-pulsatile | Pulsatile | Pulsatile |
| Directionality | Unidirectional | Bidirectional (pulsatile) | Multidirectional (pulsatile) |

Figure 2:
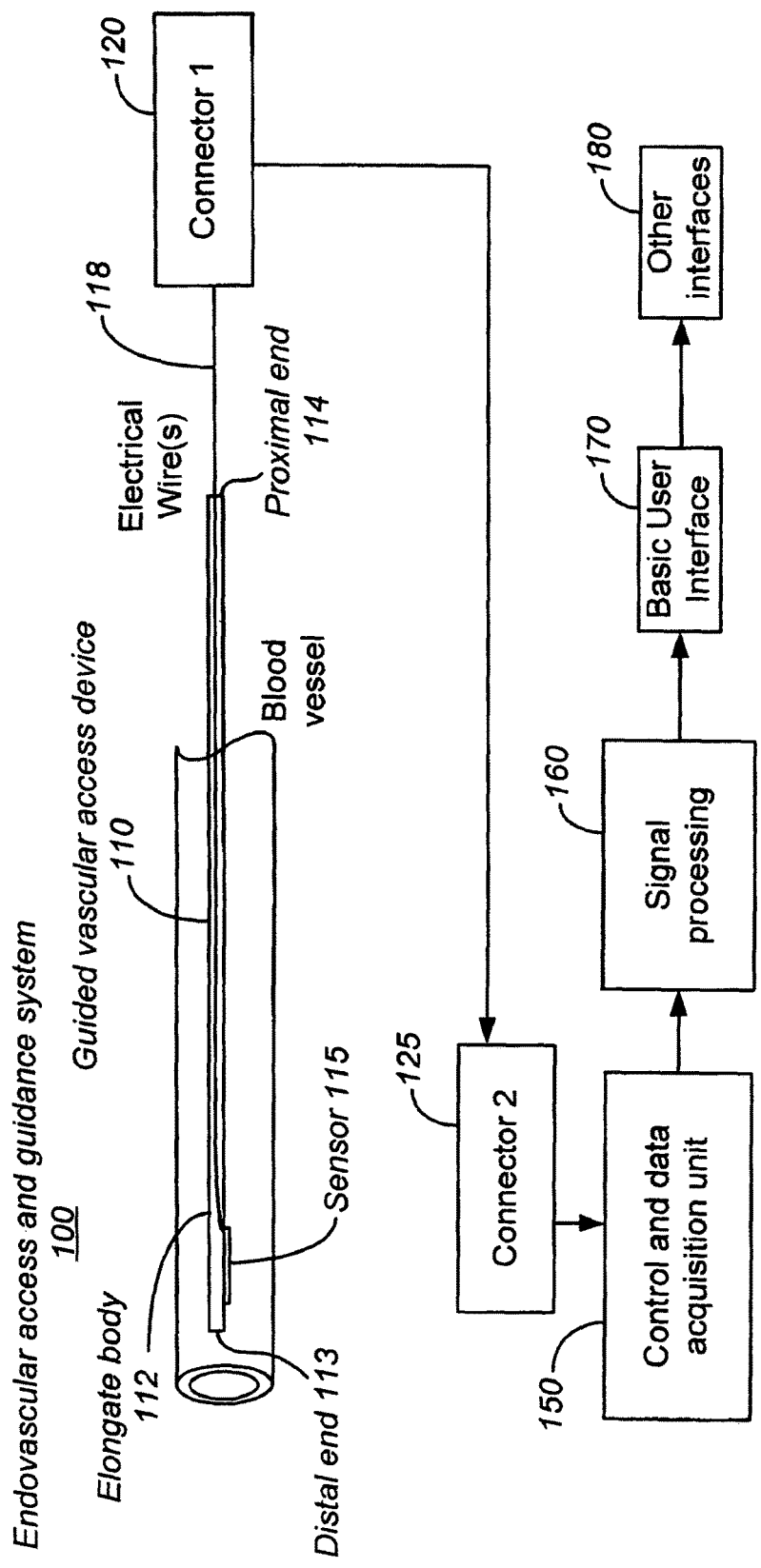
FIG. 2 illustrates the main components of an embodiment the multi-single beam ultrasound processing system of the invention. A guided vascular access device, a system for processing the signals from the guided vascular access device and a user interface.

FIG. 2 schematically represents the components of the endovascular access and guidance system. A sensor is attached to a catheter and connected through an electrical connection through a catheter lumen to an external connector. The external connector is connected to a signal processing unit that can identify the location of the sensor in the vasculature based on physiological parameters of said location. The signal processing unit is connected to a user interface.

A catheter assembly is provided that has a sensor attached close to the catheter tip (distal end). The sensor can be a pressure, Doppler, or temperature sensor, or any other type of sensor that can be used to detect physiological parameters within the blood vessel. A wire is connected to the sensor that provides and electrical connection from the sensor to the outside of the body. This can be achieved for example through an electrical connection running through the catheter wall or lumen from the sensor to a connector placed at the proximal end of the catheter. The catheter assembly containing a sensor can be built in different ways and is described in more detail below.

The connector 1 in FIG. 2 provides a means for electrically attaching the catheter assembly to a data acquisition and processing device. The possible components of a data acquisition and processing device include a connector 2 that is adapted to mate electrically or wirelessly with connector 1 of the catheter assembly, a control and data acquisition unit, signal processing unit, basic user interface, and other interfaces unit.

In one embodiment, the catheter assembly is used in the sterile field while the device is non-sterile. Therefore, the device must be bagged with a sterile bag prior to use. The connector provides a means to pierce the bag and connect to the device in the sterile bag, such that sterility is ensured for the operation of the device in the sterile field. In another embodiment, the device is sterile and is attached to the sterile catheter directly.

The apparatus implements the data processing algorithm and indicates to the user the location of the catheter or catheter tip in the vascular tree a user interface or display. In one embodiment, the user interface may be colored lights that indicate the position or status of the guided vascular access device within the vasculature. For example, a green light may indicate blood flow away from the guided vascular access device, meaning that the guided vascular access device is being advanced in the correct or desired direction, e.g., toward the heart in some applications. A red light may indicate blood flow towards the guided vascular access device, meaning that the guided vascular access device is being advanced the wrong way or in a direction away from the heart. A blue light may indicate that a blood flow pattern or other unique signature or aspect has been detected that indicates that the guided vascular access device is in proximity of the desired position within the vasculature. The desired location may be any location within the vasculature where the multi-single beam ultrasound processing techniques and the guided vascular access devices may detect a blood flow pattern or other unique signature, aspect or anatomical landmark. For example, guided vascular access devices described herein may be used to identify the junction between the vena cava and the right atrium (see, e.g., FIGS. 38, 39, 41, 42), the sapheno-femoral junction (see, e.g., FIG. 48) or in other portions of the vasculature identifiable using the systems and methods described herein. Also the invention allows for the catheter to be self-guiding without the need for an external imaging modality such as fluoroscopy or ultrasonography which is currently required with existing catheters.

Figure 3:
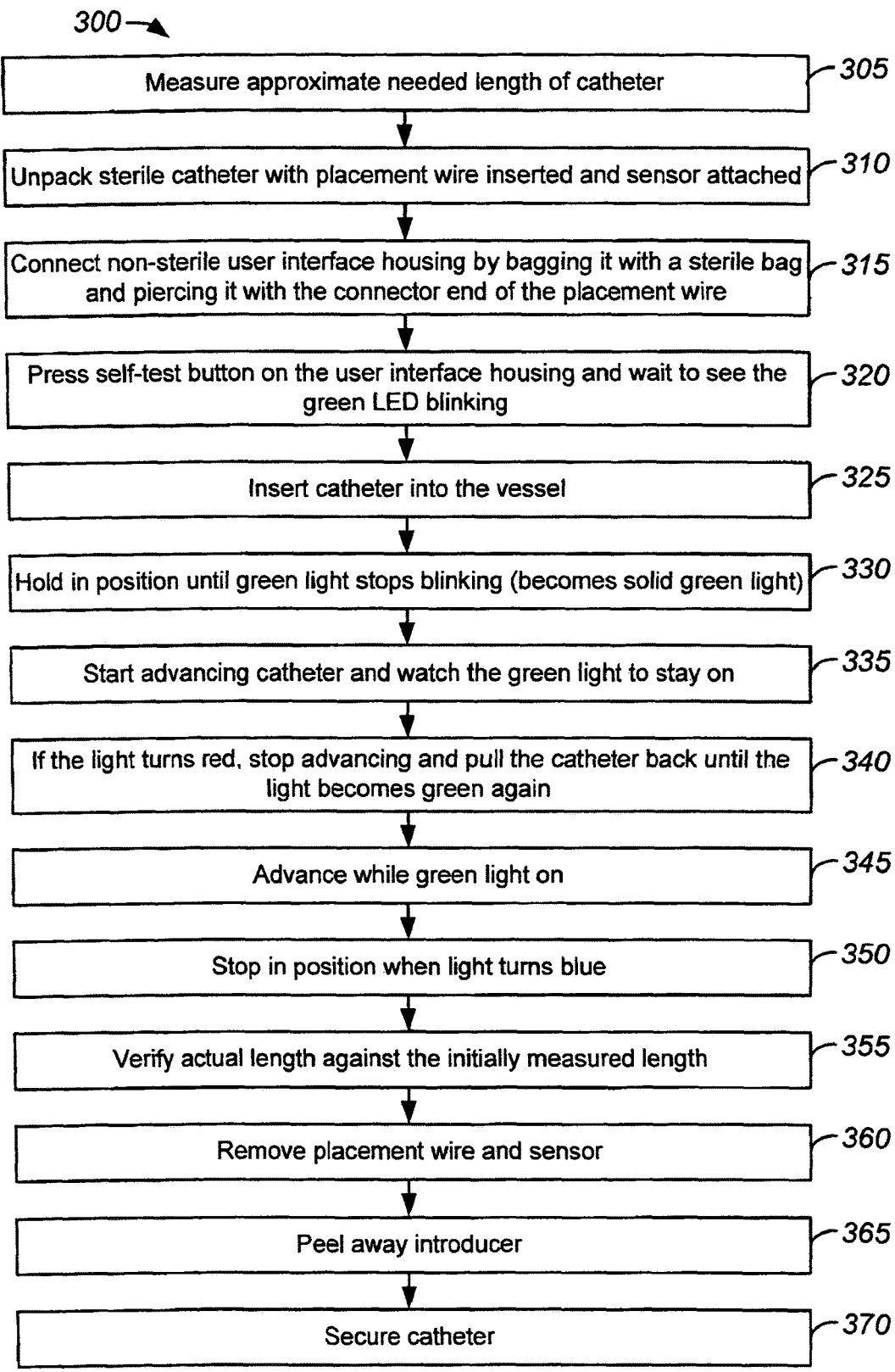
FIG. 3 is a flow chart that illustrates an exemplary method of catheter placement.

FIG. 3 illustrates an exemplary method 300 of catheter placement. In this example, the method 300 describes how a user would place a PICC catheter using a guided vascular device with guidance information provided using the multi-single beam ultrasound system and processing techniques described in greater detail below. This example is for illustration purposes only. Similar conventional catheter, guide wire or device introduction procedures, may be tailored for the requirements of other therapeutic devices such as, for example, for placement of hemodialysis catheters as well as for the placement of laser, RF, and other catheters for percutaneous treatment of varicose veins, among others described in greater detail below.

While the techniques described herein may be practiced in a number of clinical settings, the placement method 300 will be described for bedside catheter placement. The workflow presented in catheter placement method 300 begins with step 305 to measure approximate needed length of catheter. This step is recommended in order to verify the location indicated by the apparatus. This step is currently performed by the medical professional in the beginning of the procedure.

Next, at step 310, unpack sterile catheter with placement wire inserted and the sensor attached. In a preferred embodiment, the packaged catheter already contains a modified stylet with Doppler sensors. Currently, some PICC catheters are already packaged with stylets which are used by the medical professionals to push the catheter through the vasculature. Currently such catheters and the corresponding stylets do not contain any sensors.

Next, at step 315, connect non-sterile user interface housing by bagging it with a sterile bag and piercing it with the connector end of the placement wire. In a preferred embodiment, the catheter containing the stylet with sensor is sterile and disposable while the user interface, control, and signal processing unit is reusable and potentially non-sterile. If the unit is not sterilized and cannot be used in the sterile field, it has to be bagged using a commercially available sterile bag. The catheter is then connected to the user interface unit by piercing the sterile bag with the stylet connector. Alternatively, a sterile cord or cable can be passed off the sterile field and subsequently attached to a non-sterile control unit without having to puncture a bag. Other aspects of connecting the components are described below with regard to FIGS. 51 and 52.

Next, at step 320, press self-test button on the user interface housing and wait to see the green LED blinking. Once the sensor is connected the system can execute a self test protocol to check connection and sensor.

Next, at step 325, insert catheter into the vessel. This step is similar to the catheter introduction currently performed by medical professionals. One preferred insertion point in the basilic is labeled "1" in FIG. 4.

Next, at step 330, hold in position until green light stops blinking (e.g., becomes solid green light). Once the catheter is in the vessel, it must be held in position for a few seconds or be slowly pushed forward. This step ensures that the signal processing algorithm can calibrate the data acquisition and pattern recognition to the current patient data. Additionally, the processing system will analyze the sensor date to confirm that the sensor is placed in a vein not an artery. This placement confirmation aspect is described in greater detail below with regard to FIG. 34

Figure 4:
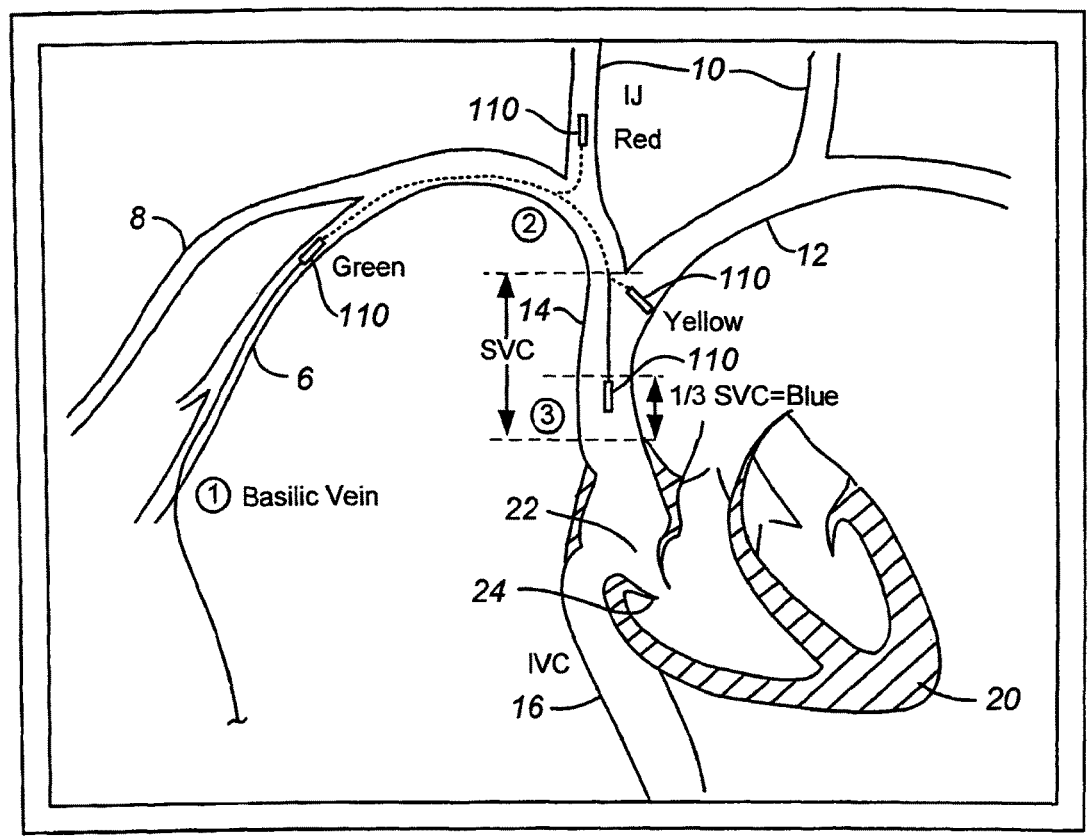
FIG. 4 illustrates a portion of a chest cavity illustrating a correct position for a catheter in the basilic vein.

Next, at step 335, after receiving confirmation from the system that the sensor/catheter has been introduced into a vein, the user may start advancing the catheter and watch the green light to stay on. If the green light is on, it means that blood flows away from the catheter tip. This "green light" indication is the desired indication while advancing the catheter/sensor to the end position. FIG. 4 shows a correct position of the catheter in the basilic vein marked "Green" and meaning that the green light is on.

Next, at step 340, if the light turns red, stop advancing and pull the catheter back until the light becomes green again. The light turns red when blood flows towards the catheter/sensor instead of away from it. This means that the catheter has been accidentally advanced into the jugular or other vein. In FIG. 4 this positioned is labeled "Red" and the catheter is shown in the internal jugular vein. In this situation the blood stream flowing towards the heart comes towards the device. In this situation the catheter must be pulled back to position labeled "2" in FIG. 4 and re-advanced on the correct path into the SVC. If accidentally the catheter is facing a vessel wall and cannot be advanced, the light turns yellow: position marked "yellow" in FIG. 4. In this situation the catheter must be pulled back until the yellow light is off and the green one is on again.

Next, at step 345, advance while green light on. The user keeps pushing while the catheter/sensor remain on the proper path toward the heart.

Next, at step 350, the user stops advancing when light turns blue. As illustrated in FIG. 4 the light turns blue when the lower third of the SVC has been identified. The light turns blue when the processing system has identified the unique flow pattern or physiological parameters corresponding to the targeted placement region. In this illustrative method, the unique nature of the flow signature in the junction of the superior vena cava and the right atrium is identified and the blue indicator light illuminated. The techniques for determining the location of such unique flow signature locations is described in greater detail below with regard to FIGS. 34-40.

Next, at step 355, the user may verify actual length against the initially measured length. This step is used to double check the indication provided by the device and compare against the expected initially measured length for the target position.

Next, at step 360, remove stylet and attached sensor.

Next, at step 360, peel away introducer and then at step 370, secure catheter.

Guided Vascular Access Devices

FIG. 5 is a table summarizing some of the features of the devices of this invention (e.g., catheters, stylets, guidewires), such as those shown in subsequent figures. In general, it may be desirable to place the sensor at or near the center of the vessel to e.g., avoid interference between the sensor and the vessel wall. In catheter embodiments, this feature may be implemented as a basket around or near the sensor. Alternatively, the distal end of the catheter may be provided with a bend or pre-formed curve to push the sensor away from the vessel wall. In stylet or guidewire embodiments, on the other hand, a J-shaped or hockey stick shaped tip may serve that purpose.

Some embodiments make use of ultrasound-derived information to enable steering a device within a blood vessel. This can be accomplished by a integrating design features that enable steering along with a sensor or sensors that provide real-time feedback information indicating tip position within the vasculature.

An important design feature enables torque control. Guided vascular access devices equipped with acoustic sensors, including catheter devices and stylets/guidewires, may be constructed using high-torque materials to enable precise control of the distal tip by rotating the shaft of the catheter or device near the insertion site. More particularly, an embodiment of a stylet (i.e., FIG. 23A) may be inserted into the lumen of a catheter (FIG. 23B) whereby the rigidity of the stylet 2312 is used to impart torque or otherwise manipulate the catheter 2370 and provide steering control in response to information provided by the system.

Another device design goal is to minimize device profile while maximizing sensor size. In catheter embodiments, this goal may be achieved by disposing the sensor in a recess formed in the distal end of the catheter.

In some embodiments, the location device may be used solely to guide another device (such as a therapy device) to a particular location in the vasculature. In other embodiments, however, location devices may be integrated with therapy delivery devices. In such embodiments, the catheter or other device may be provided with lumens for therapy delivery in addition to the device location elements. Alternatively, the catheter may be provided with slits, valves, ports, etc. for purposes of therapy delivery. Groshong describes the use of valves in closed end catheters in U.S. Pat. No. 4,549,879 for Valved two-way catheter.

Some embodiments of the invention acquire directional data that may be used, e.g., to determine the direction of blood flow. In such catheter embodiments, one or more sensors may be tip mounted and forward looking, side mounted and lateral looking, and/or rearward looking sensors. There also may be multiple sensors in one or more locations. Stylet and guidewire embodiments may also have forward looking sensor(s), rearward looking sensor(s) or a combination.

Some embodiments may provide features to maximize the sensor data acquisition volume. For ultrasound based sensors, for example, the data acquisition volume may be increased by expanding the beam to insonify a greater volume (via, e.g., a divergent beam) and/or by collecting from a larger volume by converging the collection beam. Lenses and lens assemblies (e.g., acoustic lens assemblies, shaped epoxy lens assemblies, microlens arrays, machines crystal(s)) may be used or this purpose.

The location devices may use a variety of sensor numbers, shapes, and materials depending on the application. For example, the device may use one sensor, multiple sensors, rectangular sensors, rounded sensors, etc. Suitable ultrasound-based sensor material includes piezoelectric crystals (such as quartz), piezoelectric ceramics (such as lead zirconate titanate), silicon, and piezoelectric films (such as PVDF). The lenses (e.g., converging, diverging) may be made from epoxy toughened with varying weight fractions of polymethyl methacrylate (PMMA) and polycarbonate (PC), Araldite® (Gy508/Hy956, Ciba), EPO-TEK® 353 ND (Epoxy Technology), or Rexolite® (Curbell Plastics). In some embodiments, the sensor may be made "non-flushing" (e.g., does not require flushing for purposes of purging air or other ultrasound limiting materials) by encapsulating the sensor in airtight and ultrasound transparent epoxy or other sealant. The encapsulation may also be used to attach the sensor to the catheter or other device and may be formed into the shape of a sensor lens. In addition, the seal material used for encapsulating the sensor in airtight ultrasound environment may be non-transparent to the acoustic energy generated by the sensor. As such, in some embodiments the material used to provide an air tight, sealed environment for sensor operation may also act as an acoustic lens to the sensor(s) being sealed.

Lens Arrays

The use of an array of microlenses of tens of micrometer diameter instead of a single lens with a diameter of 1-2 mm covering the entire surface of the crystal (see FIG. 17) is also disclosed. An array of lenses will allow us not only to create a divergent (e.g., defocused) beam but to orient the ultrasound energy generated by the piezoelectric crystal in different directions. Such arrays of microlenses can be etched in fused silica.

Shaped Sensors

In almost all cases, ultrasound sensors, such a ultrasound crystals, for example, use acoustical lens assemblies coupled to a piezoelectric (PZT) crystal. The use of laser micromachining of the PZT element is disclosed that produces a shaped crystal and hence alter the generated acoustic wave (FIG. 14D).

Catheter Based Guided Vascular Access Devices

Figure 7:
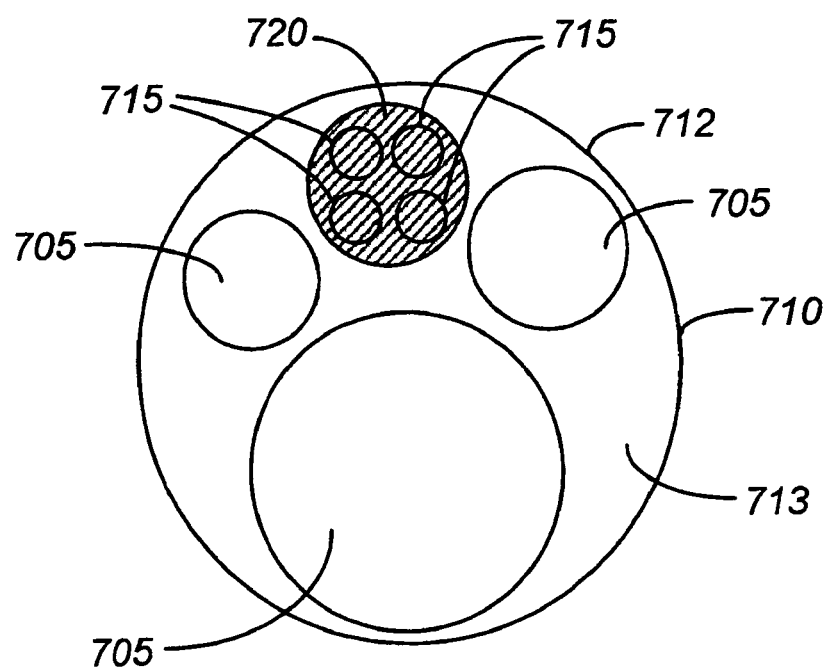
FIG. 7 shows an embodiment of the invention having four sensors at the distal end of a catheter.

FIG. 7 shows an embodiment of the invention. Four sensors 715 (e.g., Doppler crystals) are provided at the distal end 713 of a catheter 712, such as any commercially available catheter. Catheter 712 has three other lumens 705 to be used for other purposes. A disadvantage of this configuration is that it reduces the number of lumens 705 available in an existing catheter. Sensors 715 communicate with the proximal end of catheter 712 via wires (not shown) passing through lumen 720. It is to be appreciated that suitable electrical wires and connections (not shown in many of the FIGS. that follow) conventional to the ultrasonography arts connect the sensors described herein to the appropriate system components so that the sensors may be operated to produce and/or receive acoustic waves.

FIGS. 8A and 8B illustrate another possible embodiment of a catheter assembly with sensors facing laterally. In this embodiment, sensors 815A, 815B and 815C are built into the wall of catheter 810 on either side of lumen 805. Wires (not shown) extending proximally from the sensors communicate with a control system outside of the patient to provide power, data acquisition, etc. The sensors may be multiplexed to reduce the number of wires extending to the control system. In an alternative embodiment, one or more forward looking sensors may be added to the lateral sensors shown in FIGS. 8A and B. A forward looking sensor may be used, e.g., for velocity detection using Doppler techniques, while the lateral sensors may be used for wall detection using A-scan. In addition, angled sensors may be used to provide blood velocity in both directions along the catheter axis.

Embodiments of the present also relate to the use of integrated Doppler sensors into catheters, such that these sensors can monitor the direction of the blood flow, i.e., towards or away from the catheter and detect Doppler flow patterns in order to determine the location of the Doppler sensor in the vasculature. Several types of Doppler techniques can be used to achieve these goals including continuous (CW) and pulsed (PW) wave Doppler. The references to continuous wave directional Doppler are as examples and are not be considered a limitation of the invention. From a catheter assembly point of view, CW requires two transducer elements: one that transmits the ultrasound wave and another one that receives it. One such two sensor embodiment is illustrated in FIG. 8A. PW requires only one transducer element but more electronics such that the same element can be used sequentially for transmitting and receiving the ultrasound wave.

Figure 9A:
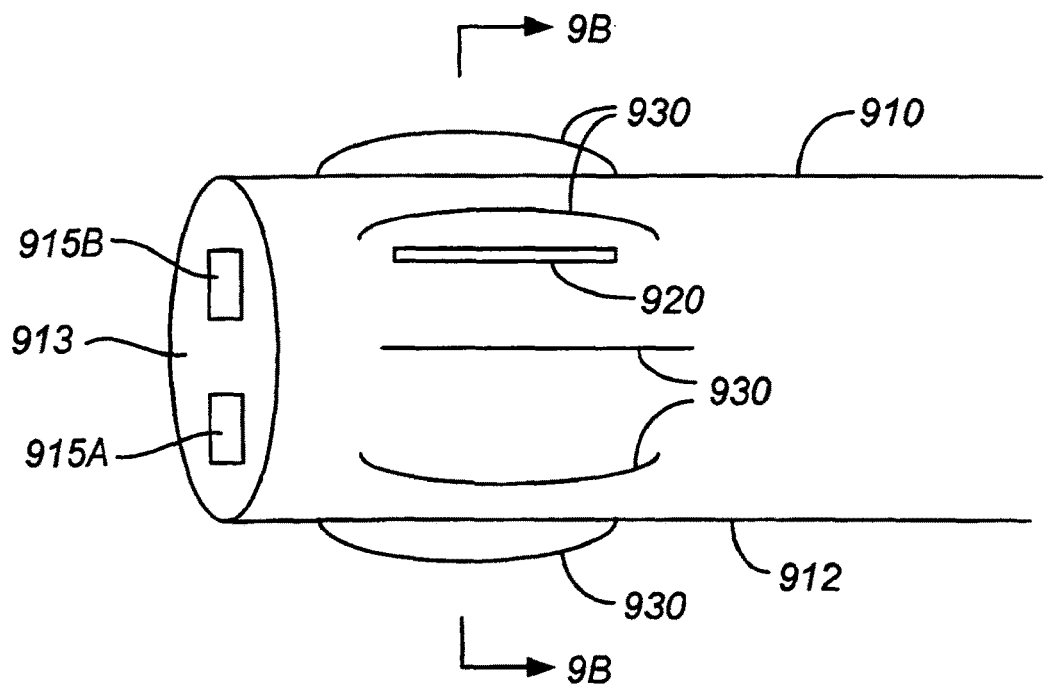
FIGS. 9A to 9D illustrate a centering device on a catheter based guided vascular access device.
Figure 9B:
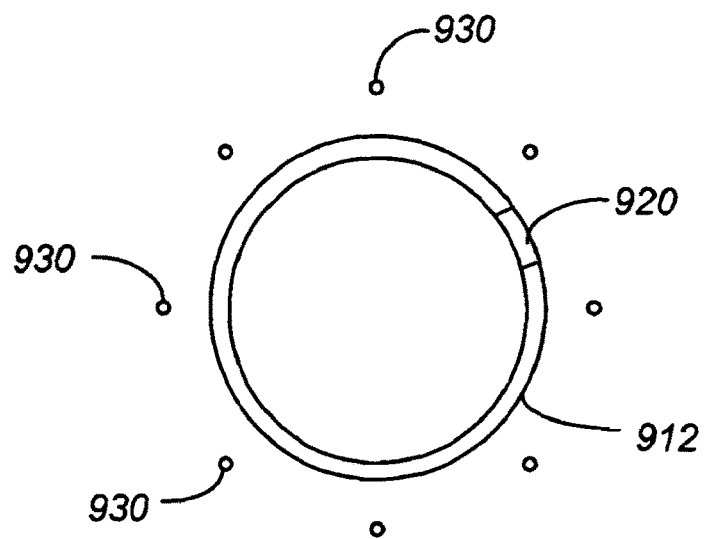
Figure 9C:
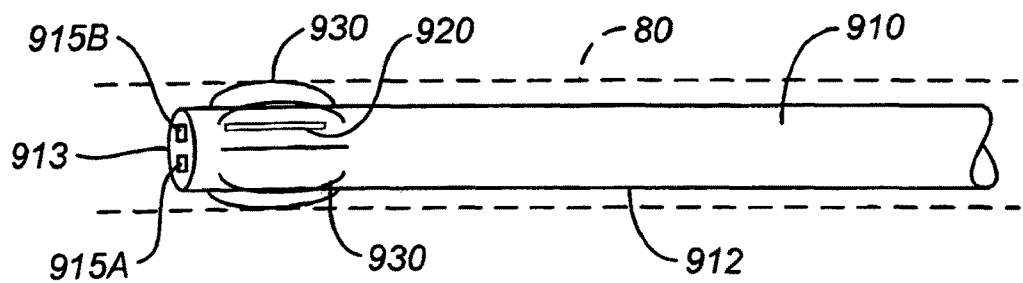
Figure 9D:
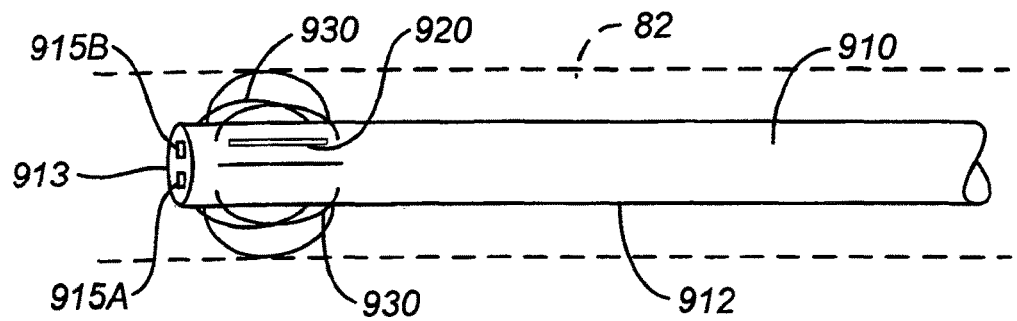

FIGS. 9A-D show a centering feature for a catheter with location devices according to this invention. In this embodiment, sensors 915A and 915B are disposed at the distal end 913 of a catheter 912. Expandable centering wires 930 (formed, e.g., from a superelastic material, such as the shape memory material Nitinol, or a biocompatible plastic) are disposed radially around catheter 912. The centering wires 930 may also take the form of narrow strips or be replaced by a balloon that may be selectively inflated to maintain centering. Selectively inflating the balloon allows the balloon to be more inflated when centering the device in a larger sized vessel and less inflated for centering the device within a smaller sized vessel. Whether strips, a balloon, or other inflatable element, the centering elements 930 expand substantially uniformly around catheter 912 to keep the catheter approximately in the center of the vessel 80. FIG. 9C shows the device in a small diameter vessel, and FIG. 9D shows the device in a larger diameter vessel, in which centering wires 930 are more fully expanded. In this embodiment, centering wires 930 are self-expanding. In alternative embodiments, the centering wires, strips, or inflatable element may be actuated by a user. Catheter 912 is also provided in this embodiment with a side delivery port 920 for providing therapy, such as a pharmacological agent, via a lumen (not shown) within catheter 912 as is conventionally done with closed end catheters.

Figure 10A:
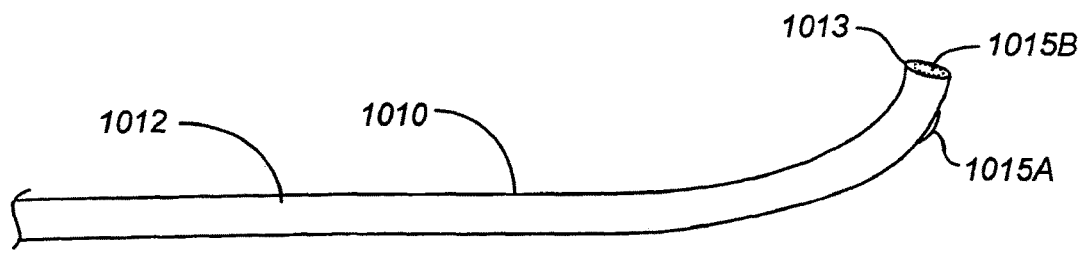
FIGS. 10A to 10C illustrate a catheter based guided vascular access device having a pre-formed shape.
Figure 10B:
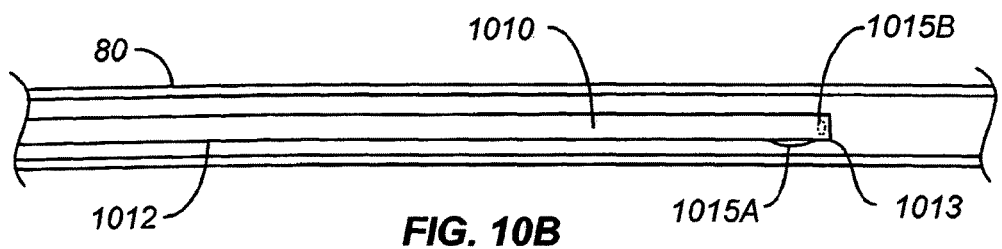
Figure 10C:
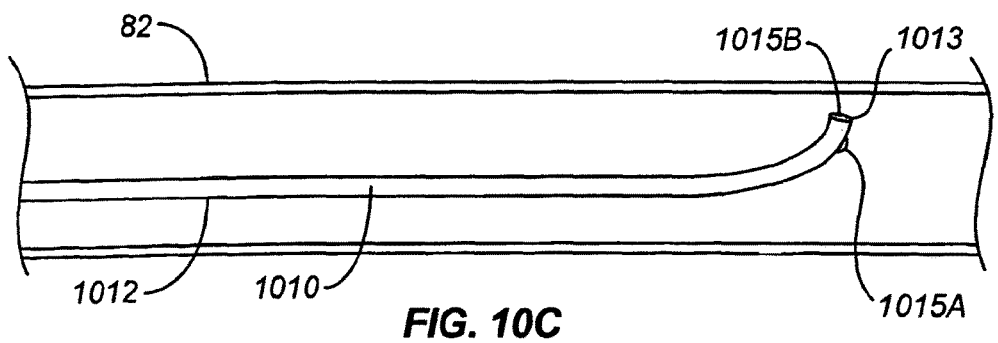

FIGS. 10A-C show another feature for a catheter with location devices according to this invention to adapt the catheter for use in different size vessels. In this embodiment, a sensor 1015A is disposed on the side of catheter 1012, and a sensor 1015B is disposed at the distal end 1013 of the catheter. The distal end of catheter 1012 may be bent by the user, as shown in FIG. 10A, using conventional catheter tip steering techniques. The amount of bending may be changed depending on the way sensors 1015A and 1015B are being used and on the size of the vessel, as shown in FIGS. 10B and 10C. Alternatively, the catheter 1012 may have a preformed bend that the catheter assumes when it is inside of a vessel as illustrated in FIG. 10C. The pre-formed bend provides a centering functionality by maintaining sensor 1015A oriented toward the flow within vessel 82.

FIG. 11A shows an embodiment of the invention in which a sensor 1115 is disposed in a recess 1122 of the elongate body 1112. The recess 1122 is within the elongate body 1112 and bounded by the surfaces 1128, 1129 and the seal 1130. The angle $\theta_2$ is formed by surface 1128 and surface 1129. The surface 1128 in the recess 1122 deflects from the surface of the catheter 1112 or other elongate body as indicated by the angle $\theta_1$. The angle $\theta_1$ indicates the angle of sensor 1115 with respect to the axis of catheter 1112. Variations of angle $\theta_1$ are useful when using sensor 1115 for Doppler readings. One or more sensors 1115 may be positioned on the surfaces 1128, 1129 and the angles $\theta_1$ and $\theta_2$ may be varied to generate and/or receive acoustic signals with the qualities and characteristics described herein.

The recess 1122 may be filled with a seal material, a lens material or a seal material having lens characteristics as indicated by the 1140/1130 reference numeral. An airtight, ultrasound transparent seal 1130 is provided over the recess 1122 and sensor 1115. Seal 1130 and/or the fill in recess 1122 may also serve as a lens for the sensor 1115. The sensor 1115 and its seal and/or lens is substantially or nearly flush with the outside surface of catheter 1112 in this embodiment. The size of the seal 1130 is not illustrated to scale and would in actuality not present so apparent an edge against the surface elongate body 1112 but would be atraumatic if it contacted a vessel wall.

FIG. 11B shows an embodiment in which the sensor 1115 and its seal 1130 and/or lens 1140 extend beyond the cylindrical outside surface of the catheter 1112. The recess 1122 may be filled with a seal material, a lens material or a seal material having lens characteristics as indicated by the 1140/1130 reference numeral. An airtight, ultrasound transparent seal 1130 is provided over the recess 1122 and sensor 1115. Seal 1130 and/or the fill in recess 1122 may also serve as a lens for the sensor 1115. The size of the seal 1130 and the size/shape of the recess 1122 extending above the surface is not illustrated to scale and would in actuality not present so apparent an edge on seal 1130 or bulge on filled portion compared to the plane of the surface of elongate body 1112. The sensor, seal/lens and seal assembly is so constructed as to remain atraumatic if placed in contact with a vessel wall.

Figure 12A:
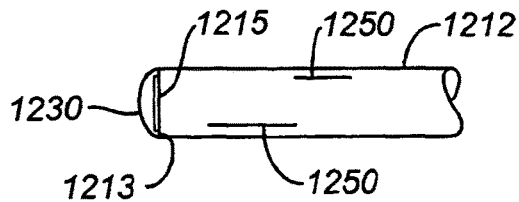
FIGS. 12A-B illustrate an embodiment of the inventor in which the sensor is disposed at the distal end of a closed end catheter.
Figure 12B:
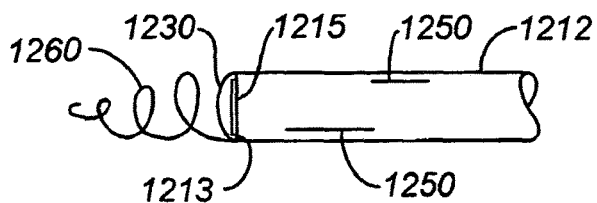

FIG. 12A shows an embodiment in which a sensor 1215 (possibly covered by a lens 1230) is disposed at the distal end 1213 of a closed end catheter 1212. Slits 1250 permit substances to be delivered through catheter 1212. Ports or valves may be used in place of the slits. Slits 1250, the use of ports and valves and additional information regarding the operation and use of closed end catheters are further described by Groshong in U.S. Pat. No. 4,549,879. One or more additional sensors could be included on the closed end catheter 1212 such as on distal end 1213 or laterally mounted as described below with regard to FIG. 13C. FIG. 12B shows the addition of an atraumatic tip 1260 at the catheter distal end 1213.

FIG. 13A shows an embodiment in which three sensors 1315A-C are disposed at the distal end 1313 of the catheter and one sensor 1315D is disposed on the side of the catheter. A lens-shaped seal 1340 covers sensor 1315D. FIG. 13B shows an embodiment with only two sensors 1315E and 1315F at the distal end of the catheter. A lens/seal (not shown) may also be placed in FIGS. 13A, 13B over the distal ends to seal and/or modify the acoustic waves generated by the sensors 1315A-F. In FIG. 13C, the sensor 1315D sits on an angled surface 1328 and is covered by a lens/seal 1340.

Figure 14A:
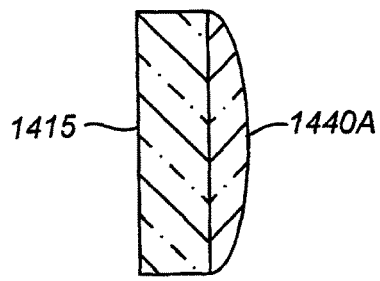
FIGS. 14A-E illustrate a variety of sensor and lens arrangements.
Figure 14B:
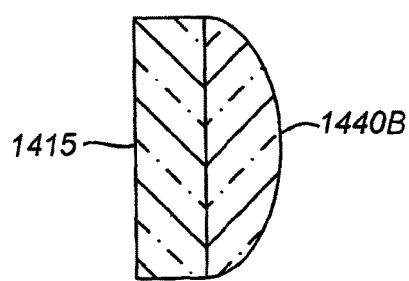
Figure 14C:
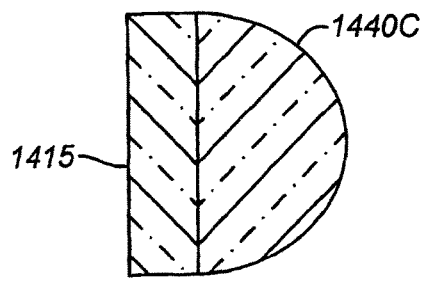
Figure 14D:
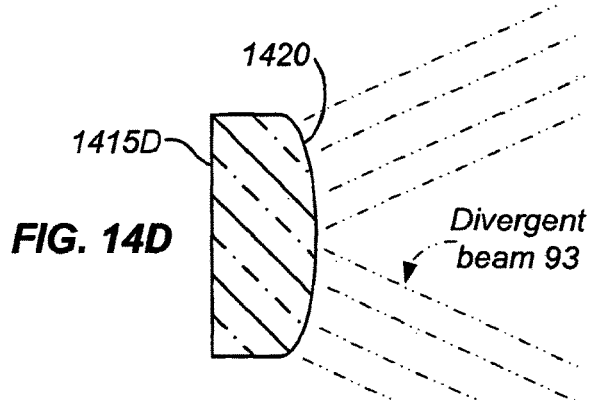
Figure 14E:
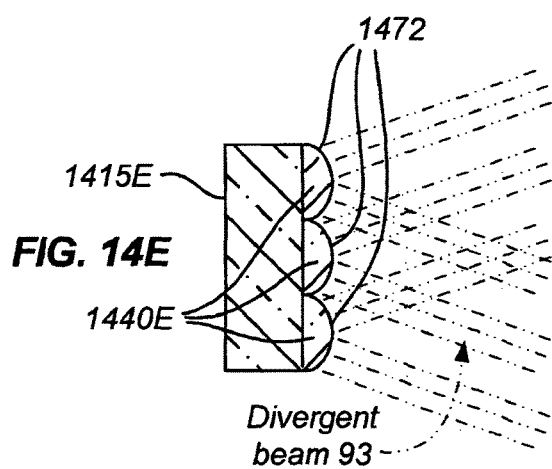

FIGS. 14A-E show different sensor and lens arrangements. In FIGS. 14A-C, a different shaped lenses 1440 A-C are illustrated covering a sensor 1415. The shape of the lenses 1440A-C can be used to modify the acoustic waves transmitted or collected by the sensor 1415 to have the desired characteristics to accomplish the ultrasound techniques described herein. In FIG. 14D, the surface of the sensor 1415D itself has been altered to produce a shaped surface 1420. Shaped surfaces 1420 may be formed in sensors using suitable shaping processes such as, for example, the use of laser micromachining of a sensor that is made from piezoelectric material. Because of the characteristics of the shaped surface 1420, an activated sensor 1415D produces a divergent ultrasound beam 93, as shown. In FIG. 14E, a plurality of lenses 1440E (such as fused silica lenses) having shaped surfaces 1472 cover sensor 1415E to provide a plurality of divergent beams 93.

Figure 15:
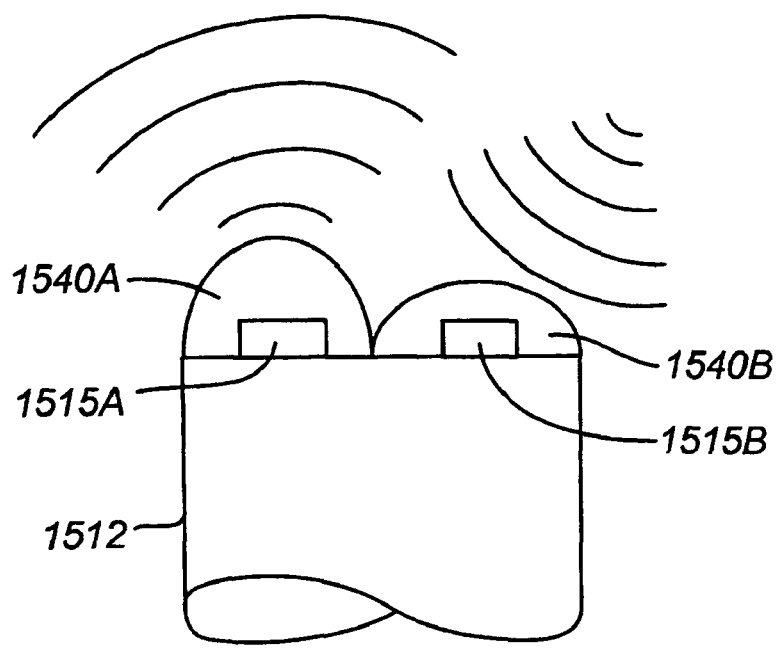
FIG. 15 illustrates the tip of a stylet, or other elongate body, with sensors positioned at its distal end.

FIG. 15 shows a stylet or other elongate body 1512 with sensors 1515A and 1515B at its distal end. Lenses 1540A and 1540B cover sensors 1515A and 1515B, respectively, have different shapes and provide different beam shapes for transmission or collection. In this embodiment, one sensor may be used as a transmitter (i.e., 1515A) and the other as a collector (i.e., 1515B).

FIG. 16A shows a stylet or other elongate device 1612 with a distal end 1613 in which a seal 1630 covers the sensor 1615. The seal 1630 may be formed from a suitable ultrasound transparent material to provide an airtight environment for the operation of the sensor 1615. Alternatively, the seal 1630 may have acoustic beam altering properties such that it acts like a lens in addition to providing an air tight environment for sensor 1615. In contrast, the seal 1630 is separate from the lens 1640 in FIG. 16B. The lens 1640 is sized to conform to the size and surface of sensor 1615. As illustrated, the seal 1630 covers the stylet distal end 1613 and can be used to secure the lens 1640 to the sensor 1615 and both of these components to the distal end 1613.

Figure 17:
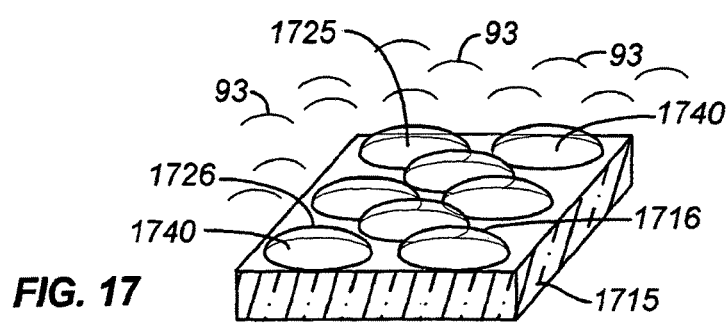
FIG. 17 illustrates an array of microlenses attached to a sensor.

FIG. 17 shows a sensor 1715 to which an array of microlenses 1740 have been attached. The lens shape 1726 can provide a divergent (e.g., defocused) beam 93 and can orient the ultrasound energy generated by the sensor (such as a piezoelectric sensor) in different directions. The lens shape 1726 need not be the same on every lens 1740 at all locations in the array. Instead, in some embodiments, the shape, size and density of the microlenses 1740 varies across the surface of sensor 1715 to produce the desired ultrasound beam characteristics. The microlens array can be formed from etched fused silica, for example, or from other suitable lens material as described herein or known in the ultrasonography arts.

Guide Wire Based Guided Vascular Access Devices

Figure 18B:
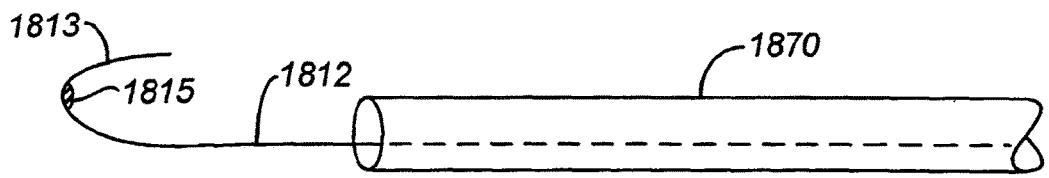
Figure 18C:
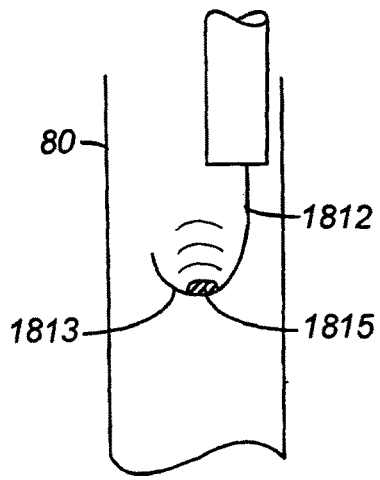

FIGS. 18A-C show the use of a location device with a guidewire 1812. In FIG. 18A, sensor 1815 is disposed at the distal portion 1813 of guidewire 1812. Guidewire portion 1813 is bent into a substantially J shape, and the sensor 1815 is disposed on the concave side of the bent portion to face toward the proximal end of the guidewire 1812. When a sheath or other device 1870 is loaded over guidewire 1812, sensor 1815 faces the device 1870, as shown in FIG. 18B. The J shape of the guidewire 1812 also provides a centering feature within the vessel lumen 80, as shown in FIG. 18C. Techniques for attaching sensors to guidewires and inserting them directly into the blood stream as disclosed by Millar in U.S. Pat. No. 5,046,497 for Structure for coupling a guidewire and a catheter and U.S. Pat. No. 4,966,148 for Assembly for positioning diagnostic devices in a biological vessel.

Figure 19B:
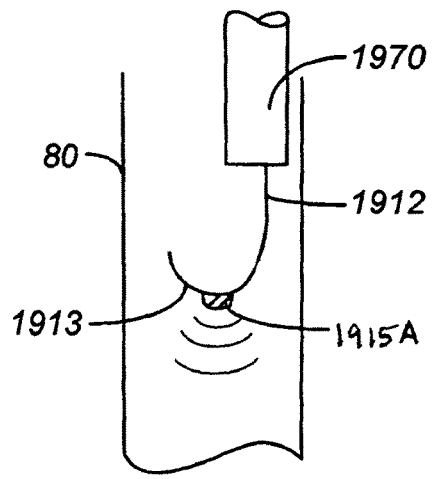

In FIGS. 19A and B, the sensor 1915 is disposed on the convex side of the distal portion 1913 of guidewire 1912 so that it faces away from the sheath 1970 or other device loaded over the guidewire. As in the FIG. 18 embodiment, the J shape of the guidewire provides a centering feature for the device to keep the sensor away from the vessel wall. FIG. 20 shows sensors 2015A and 2015B on both the concave and convex sides of the guidewire bent distal portion 2013. The J shape 1913 of the guidewire 1912 also provides a centering feature within the vessel lumen 80, as shown in FIG. 19B.

Figure 21A:
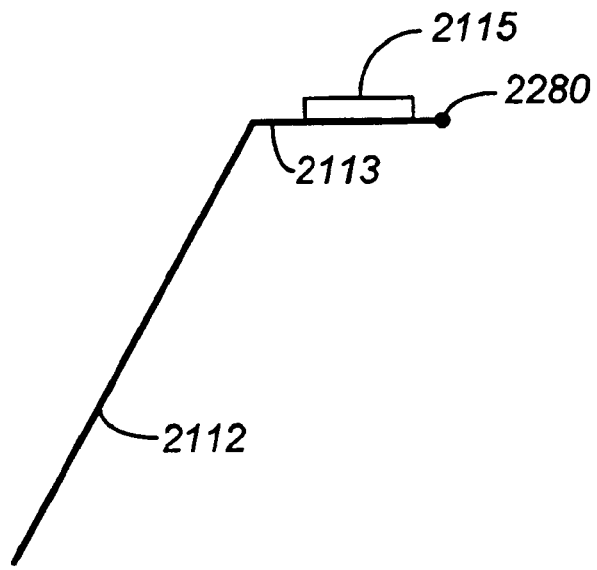
FIGS. 21A-B illustrate a guidewire having a hockey stick shaped distal portion with a sensor positioned thereon.
Figure 21B:
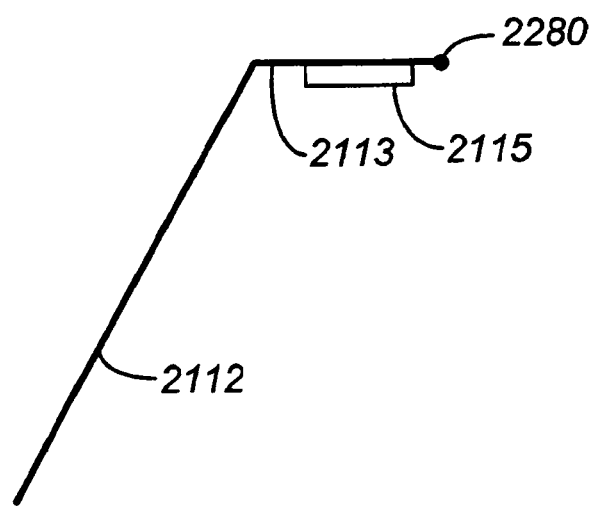

FIGS. 21A and 21B show an alternative to the embodiments of FIG. 20. In FIGS. 21A and B, guidewire 2112 has a hockey stick shaped distal portion 2113. In FIG. 21A, the sensor 2115 is disposed on a surface of the bent portion 2113 facing away from the proximal portion of the guidewire (i.e., the portion of the guidewire positioned before the bend of the guidewire), and in FIG. 21B the sensor 2115 is disposed on a surface of the of bent portion 2113 of the guidewire facing toward the proximal portion of the guidewire. As in the FIG. 20 embodiments, the bent portion of the guidewire helps to center the device within the vessel to keep the sensor away from the vessel wall. The guidewire may also be provided with an atraumatic tip 2280.

Figure 22A:
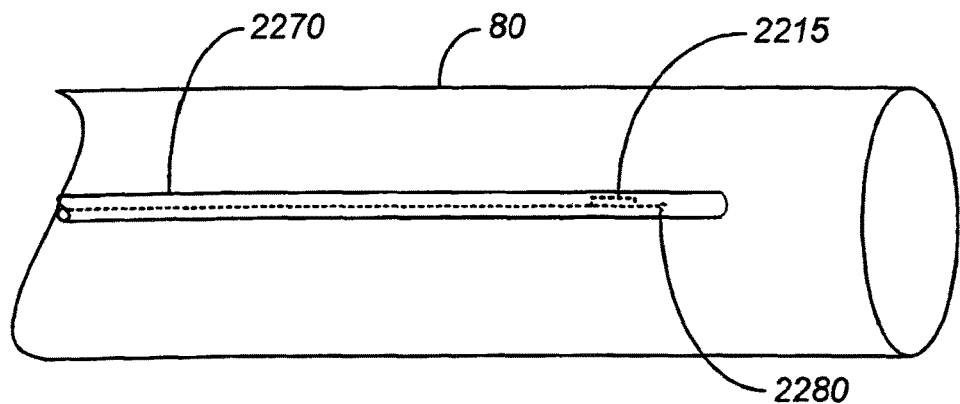
FIGS. 22A-B illustrates a sheath for use in introducing the guidewire of FIGS. 20-21.
Figure 22B:
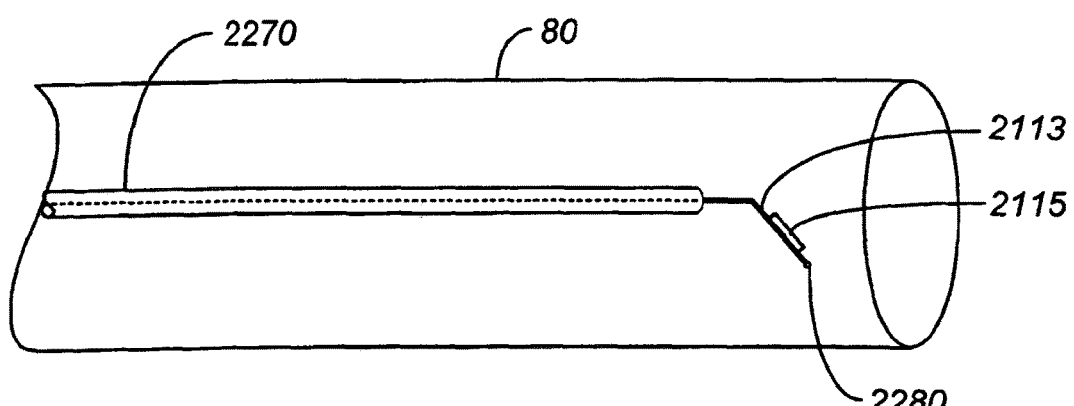

FIGS. 22A and B show a sheath 2270 for use when introducing the guidewire of FIG. 20 or 21. As shown in FIG. 22A, sheath 2270 maintains the guidewire substantially straight for introduction into the vasculature 80. When the sheath is withdrawn from the guidewire (or when the guidewire is advanced beyond the sheath), the distal end 2213 of the guidewire 2212 assumes its pre-shaped bend (shown here as the hockey stick shape). A sensor 2215 is shown on the distally directed face of the guidewire. The guidewire may also be provided with an atraumatic tip 2280.

Stylet Based Guided Vascular Access Devices

Figure 24:
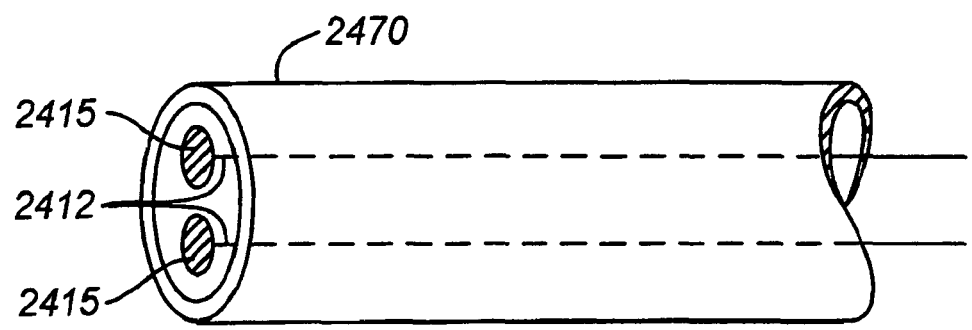
FIG. 24 illustrates an embodiment of the invention where the guided vascular device is a stylet with two sensors on the distal end.
Figure 23A:
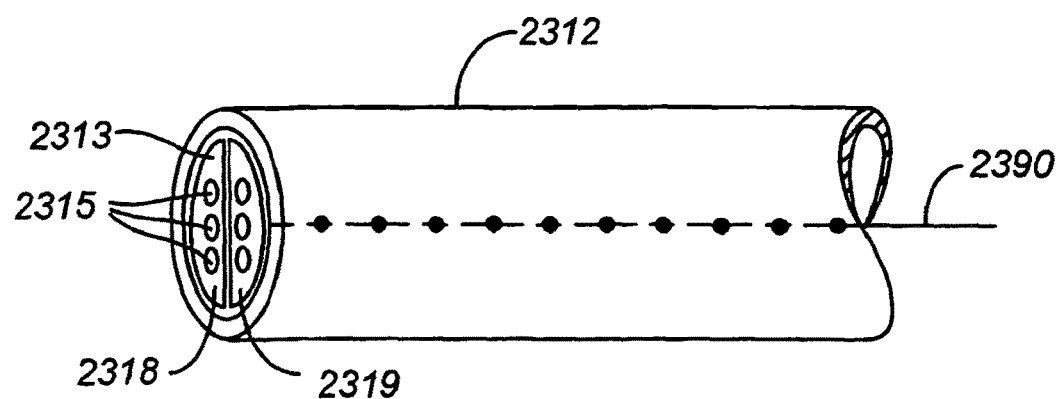
FIGS. 23A-B illustrates an embodiment of the invention in which a plurality of sensors are disposed on the distal end of a stylet.
Figure 23B:
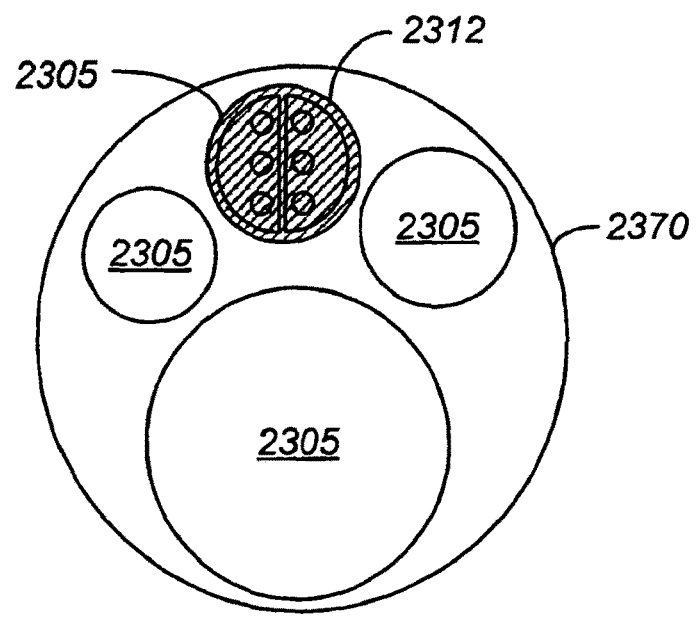

FIG. 23A shows an embodiment in which a plurality of sensors 2315 are disposed on the distal end 2313 of a stylet 2312 or other elongate body. In this embodiment, the sensors 2315 are arranged in two sensor areas 2318 and 2319. In one alternative embodiment, the sensors in one sensor area operate as emitters and the sensors in the other sensor area act as collectors. A seal, lens, or sealing lens may be used to cover one or more of the sensors 2315 in a sensor area, all the sensors in a sensor area or all the sensors in both sensor areas. In other embodiments, more than two sensor areas are used. The number of sensors 2315 in a sensor may vary depending upon the function and location of specific sensor area, such as tip mounted as shown, laterally mounted (i.e., FIGS. 13C, 11A, 11B) or angle mounted (FIG. 8A, 8B). A wire or other electrical connection 2390 extends proximally from the sensors. As shown in FIG. 23B, stylet 2312 may be disposed in a lumen 2305 of a multi-lumen catheter 2370 for guidance. As illustrated in FIG. 24, two guidance stylets 2412 with distal sensors 2415 may be disposed in a catheter 2470. Sensors 2415 may also be covered by a seal, a lens or a sealing lens as described herein. In alternative embodiments, the guidance stylets may include one or more lateral sensors such as the arrangement shown in FIG. 13C that are used together with or in place of the illustrated distal end sensors 2415.

FIG. 24 illustrates an embodiment where the guided vascular access device is a stylet with two sensors on the distal end. In one embodiment, a sensor is attached to the distal end of a stylet used to navigate the PICC through the vasculature. At the proximal end, a data acquisition unit acquires the Doppler frequency shifts using, for example directional continuous wave Doppler. A signal processing unit analyzes the Doppler frequency shift, i.e., the blood velocities, and determines the direction of blood flow relative to the catheter tip. The signal processing unit is also responsible for identifying the unique flow pattern characteristic to the junction of the superior vena cava and the right atrium. The sensors may be a piezoelectric crystal, a piezoelectric ceramic, comprise silicon or a thin piezoelectric film. The sensors may be made of the same or different materials.

Figure 6:
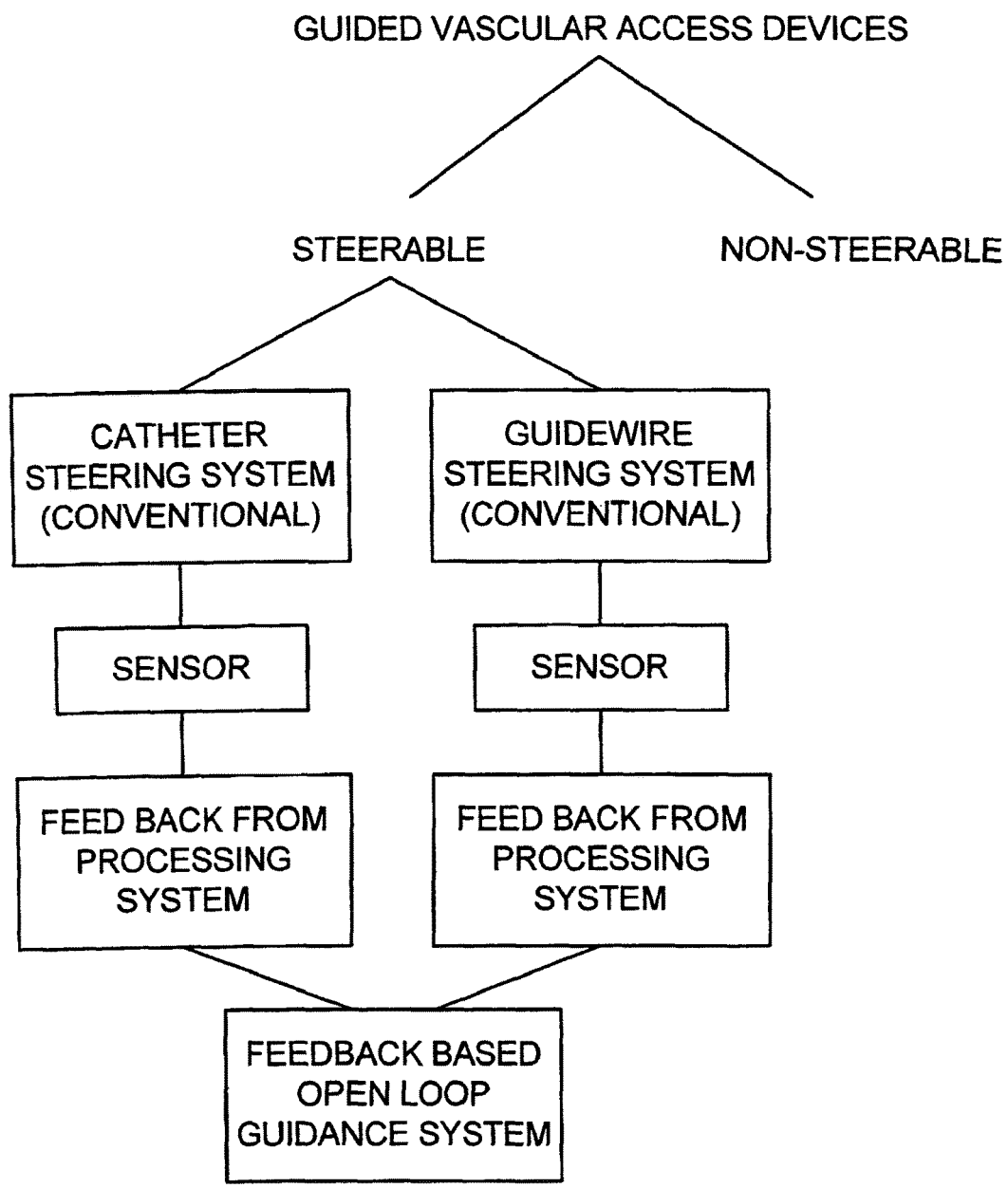
FIG. 6 is a chart describing characteristics of steerable and non-steerable guided vascular access devices.

As illustrated in FIG. 6, guided vascular access devices described herein may also be categorized as steerable or non-steerable. As illustrated in FIG. 6. a suitable conventional steering system (i.e., catheter based or guidewire based) may be used to provide steering control of the inventive guided vascular access devices described herein. The result is a feedback based open loop vascular guidance system. Similarly, FIG. 6 illustrates how suitable conventional steering system from a guide wire based steering system, when used to provide steering control of a guide wire based guided vascular access device, results in a feedback based open loop vascular guidance system. Steering capabilities may be provided in a number of ways. A guided vascular access devices of the present invention may be modified to include and be controlled by the components of a conventional catheter of guidewire steering system. Alternatively or additionally, a guided vascular access device of the present invention may be incorporated into an existing steerable interventional or diagnostic medical device. Examples of catheter steering systems are described in the following patents related to steerable catheters U.S. Pat. No. 7,037,290 to Gardeski et al. for Multi-lumen steerable catheter; U.S. Pat. No. 5,938,603 to Ponzi for Steerable catheter with electromagnetic sensor; U.S. Pat. No. 6,866,677 to Douk et al. for Temporary intraluminal filter guidewire and methods of use; U.S. Pat. No. 6,591,144 to Pigott for Steerable catheter and method for locating coronary sinus, and U.S. Pat. No. 5,803,083 to Buck et al. for Guiding catheter with ultrasound imaging capability. Examples of steerable guidewire control systems are described in the following patents: U.S. Pat. No. 6,500,130 to Kinsella et al. for Steerable Guidewire; U.S. Pat. No. 6,638,243 to Kupiecki for Balloon catheter with delivery side holes; and U.S. Pat. No. 6,973,352 to Tsutsui for Steerable cardiac pacing and sensing catheter and guidewire for implanting leads.

Figure 6B:
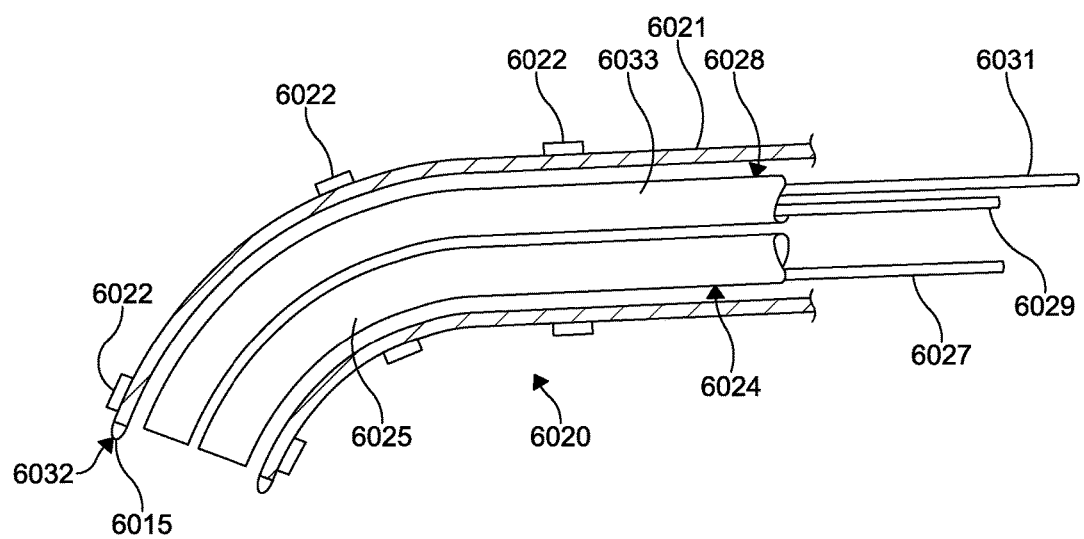
FIG. 6B illustrates an enlarged view of a portion of the embodiment of FIG. 6A, shown cut-away.

FIGS. 6A and 6B show a steerable embodiment of a guided vascular access device of the present invention adapted for use with an oximetric catheter 6010 that can be used to practice the present invention. The catheter 6010 includes a steerable cannula 6020, including a blood-contacting sheath 6021 that is fabricated from biocompatible polymers with low thrombogenicity. One or more lateral sensors described herein may be placed along the length of the cannula 6020 for to assist in guidance. Preferably encased within the sheath 6021 of cannula 6020 is a steering mechanism including a steerable guide 6024, and a blood characteristic sensor such as a fiber optic oxygen sensor assembly 6028. The fiber optic oxygen sensor assembly 6028 and other suitable cardiac monitoring sensors of the type suited to the heart access methods described with regard to FIGS. 46 and 47 and associated methods for guiding or accessing the left heart via the inventive methods of locating the coronary sinus. The electrical leads for all sensors, steerable guide 6024 and fiber optic oxygen sensor assembly 6028 preferably run the entire length of cannula 6020 to the distal end 6032 and also extend from the proximal end 6026 of cannula 6020. The fiber optic oxygen sensor assembly 6028 could be replaced by another sensor appropriate to other blood characteristics that are correlated with the blood of the coronary sinus, such as pH or $CO_2$ content.

Steerable guide 6024 preferably includes an outer tube 6025 and an internal wire 6027 that runs from the distal end 6032 to steering control module 6030. Finger grips 6034 and thumb grip 6036 of control module 6030 are reciprocally movable relative to each other along the axis of steerable guide 6024. Thumb grip 6036 is affixed to the outer tube 6025 of guide 6024 and finger grips 6034 are affixed to the proximal end of the internal wire 6027. The distal end of the internal wire 6027 is affixed to the distal end of the outer tube 6025 of steerable guide 6024 in an axially offset manner as is known in the art. Alternatively, the outer tube 6025 can be eliminated and the internal wire 6027 instead affixed directly to the sheath 6021 of cannula 6020, in which case the thumb grip 6036 could be affixed to sheath 6021 with finger grips 6034 being affixed to wire 6027. By pulling finger grips 6034 toward thumb grip 6036, the internal wire 6027 is placed in tension, thereby deflecting the distal end of steering guide 6024, and hence sheath 6021 and cannula 6020, to one side. Through a combination of deflecting the distal end of cannula 6020 via grips 6034 and 6036, and rotating the entire catheter 6010 about its longitudinal axis, likewise via grips 6034 and 6036, the distal end of catheter 6010 can be steered anywhere within a 360 degree range. Other steering mechanisms as known in the art can also be used. The user may apply steering controls based on the output of the processing system of the present invention.

One blood characteristic sensor uses fiber optics to sense oxygen content, but alternatively or additionally, pH or $CO_2$ sensors can be used. The fiber optic assembly 6028 includes a pair of optical fibers 6029 and 6031 encased in a tube 6033.

These fibers—along with electrical connections to sensors 6015—run the entire length of assembly 6028 and are connected at their proximal end to a photodetector optical module 6038, and to processor and display 6041 (modified for generating, collecting and processing the ultrasound data of the inventive system), respectively.

According to a well known phenomenon, the color of the blood is a function of the percentage of oxygen saturation of the blood. Consequently, the color of the light absorbed by the blood, and hence the color of the light reflected back to the optical module 6038, is also a function of oxygen content of the blood. The photodetector in optical module 6038 is differentially responsive to different wavelengths of light, and generates an electrical signal indicative of the wavelength of the reflected light received via the optical fiber. The generated signal can be conveyed via suitable conductors 6039 to a processor and display module 6041 that can process the signal and display the percentage oxygen saturation in a form that is directly readable by a human, such as a digital display. The processor and display module 6041 also includes the necessary components for the operation of the illustrated sensors as described herein. The output of the oxygen content or other parameter measured herein may also be indicated as part of the user display, such as in FIGS. 49, 50A and 50B.

Steerable oximetric catheter 6010, which combines the inventive ultrasound sensors described herein with an oxygen sensing optical fiber assembly 6028 with a wire-steerable guide 6024 in a common cannula 6020. provides a new technique useful for locating the coronary sinus. The oxygen content of blood in the coronary sinus is known to be among the lowest in the human body. This phenomenon is exploited by the steerable oximetric catheter 6010 in cooperation with the sensor and processing abilities of the present invention to identify unique flow signatures and patterns to facilitate locating the coronary sinus. By monitoring the oxygen content along with flow pattern information, and other characteristic of the blood in the vicinity of the distal end of catheter 6010 in real time as catheter 6010 and the sensors 6015 are advanced through the right atrium (initially located using the techniques of FIGS. 45, 46 and 47), the operator can know whether the distal end of the catheter is either on or deviating from a path approaching the coronary sinus. The detection by the system of a signature flow pattern in conjunction with sensed percentage of oxygen saturation continues to drop as catheter 6010 is advanced, then the operator knows that the distal end of the catheter is getting closer to the coronary sinus. If the oxygen saturation begins to rise or the detected flow patterns and parameters indicated by sensors 6015 change as the catheter is advanced, then the operator knows that the catheter is off course and he can correct the course using the steerability feature of the catheter. In effect, the operator is seeking to detect the unique flow patterns and parameters of the coronary sinus in combination with the low oxygen blood that exits from the coronary sinus into the right atrium. With an iterative procedure, the operator can make use of the percentage oxygen saturation being sensed in real time along with detected flow patterns and parameters to guide and adjust his steering of the catheter to find the coronary sinus. The iterative procedure above may be used to augment the blood flow information provided by the methods described herein and also displayed on a suitable user display.

FIG. 6C is a side view of a guiding catheter with multi-single beam ultrasound capability of the present invention with an electrophysiology catheter within the guiding catheter and two thumb slides for steering the guiding catheter.

FIG. 6D is a side view of a guiding catheter with multi-single beam ultrasound capability of the present invention with an electrophysiology catheter within the guiding catheter and four thumb slides (only three of which are shown) for steering the guiding catheter. One exemplary use of such a device is to use the sensors and methods described herein for use as a identification of unique flow patterns to be used in locating an endocardial ablation site and, thereafter, deploying an electrophysiology catheter for accessory pathway diagnosis and ablation.

The guiding catheter 6110 comprises three primary components. The guiding catheter body 6111 defines a central lumen 6130 (shown and described with reference to FIG. 6D) within which is guided an electrophysiology catheter 6015. One or more ultrasound sensors 6118 and lateral sensors 6117 are fixedly attached to the distal end of the catheter body 6111. In turn, the guiding catheter body 6111 is fixedly attached at its proximal end to a hub 6113 by conventional means.

An exit hole 6114 is defined towards the distal end of the guiding catheter body 6111 through which the electrophysiology catheter 6115 exits the central lumen 6130. The electrophysiology catheter 6115 comprises a tip electrode 6116 at its distal end for mapping and/or ablating endocardial tissue and is mounted at its proximal end to a control handle 6119. Preferably, the electrophysiology catheter 6115 is steerable by longitudinal movement of the control handle 6119 relative to the body of the electrophysiology catheter 6115. Aberrant conductive pathway signals can be received from the tip electrode 6116 and transmitted to a remote detector and displayed via a molded electronic connector 6120. RF energy can be transmitted to the tip electrode 6116 via a remote RF source also connected to the molded connector 6120. An exemplary example of an electrophysiology catheter suitable for use with the present invention is a steerable open lumen catheter as described in U.S. Pat. No. 5,431,168 to Webster, Jr. for Steerable open-lumen catheter, and manufactured by Cordis Webster, Inc., Baldwin Park Calif. However, many other electrophysiology catheters could be used without departing from the scope of the invention.

The guiding catheter body 6111 can be of any suitable length for intravascular insertion. In the described embodiment, a length of about 100 cm is used. Similarly, the exit hole 6114 can be of any suitable size to allow an electrophysiology catheter to exit the guiding catheter body 6111. In the described embodiment, a size of 0.04.+−0.03 inches is used and the distance between the distal edge of the exit hole 6114 and the distal end of the catheter tip 6112 is approximately 2.5 cm. One or more ultrasound sensors 6118, 6117 are fixedly attached to the distal end of the guiding catheter body 6111. The sensors 6118, 6117 emits and receive ultrasound as determined by the control system described herein and in FIGS. 25, 26 and 27, for example. In addition, other sensor configurations described herein can be employed to obtain additional flow information. The exact dimensions of the sensors 6118, 6117 are not critical and any sensor of suitable construction or described herein can be employed. Preferably, the sensor is cylindrical with a rounded tip approximately 1 to 2 cm in length and has an outer diameter of about 12 to 12.5 French so as to form a continuous outer surface with the guiding catheter body 6111.

The guiding catheter body 6111 comprises four main sections as follows (from proximal to distal end): a main body 6127, a first transitional tip 6126, a second transitional tip 6125 and the distal catheter tip section 6112. Each of these four sections can be of any suitable construction and dimensions.

A braided wire sleeve 6134 also runs the length of the guiding catheter body 6111 but only up through the second transitional tip 6125, ending slightly proximal to the end of the second transitional tip 6125 to form a proximal catheter tip joint section 6128. In the described embodiment, the width of the proximal catheter tip joint section 6128 is approximately 0.04+/−0.03 inches and the braided wire sleeve 6134 is preferably constructed of stainless steel.

Figure 6E:
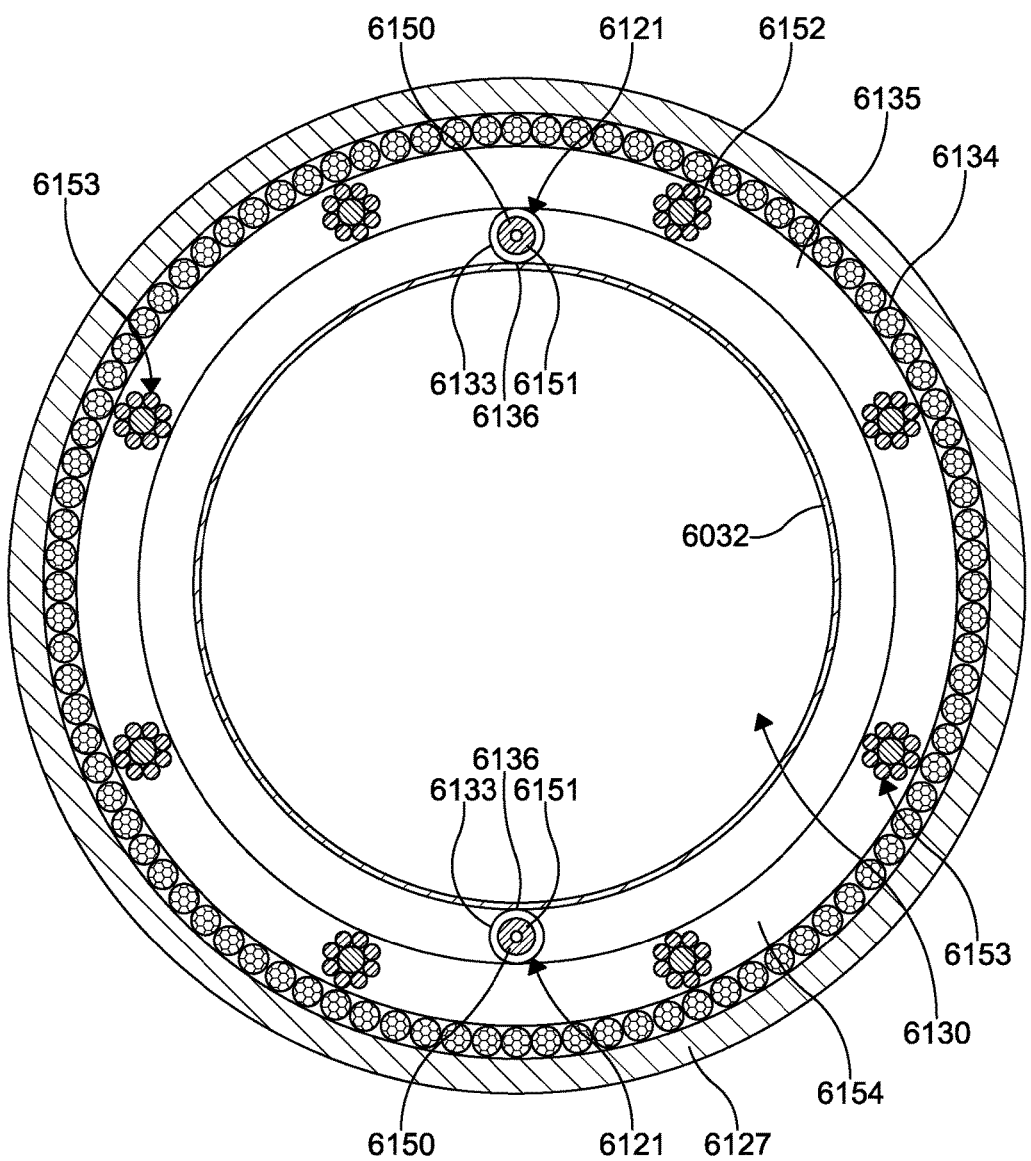
FIG. 6E is a cross sectional view of the guiding catheter body of FIGS. 6C and 6D.

A cross sectional view of the guiding catheter body 6111 taken along line 4-4 of FIG. 6C is shown in FIG. 6E. With the exceptions as indicated herein, the construction of each of the four sections comprising the guiding catheter body 6111 is substantially similar and involves the following layers. The innermost layer is an inner liner 6132, preferably constructed of PTFE, and defining a central lumen 6130 running longitudinally its entire length.

In the described embodiment, the central lumen 6130 has an inner diameter of about 0.110 inches. Preferably, the inner liner 6132 defines two longitudinal grooves 6136 on its outer surface at opposite sides from each other. A pair of small puller wire tubes 6133 are situated in the grooves 6136 to maintain their orientation. Preferably, the puller wire tubes 6133 are constructed of polyamide with an inner diameter of approximately 0.012 inches. Puller wires 6121 run axially within the puller wire tubes 6133. The puller wires 6121 (not shown for clarity) have a diameter of about 0.01 inches. The puller wires 6121 are constructed of stainless steel cable 6150 with a PTFE sleeve 6151 covering them to provide lubricity within the polyamide tubes 6133.

A layer 6135 of eight braided ribbon cables 6153 run longitudinally along either side of the puller wire tubes 6133 and arranged to surround the inner liner 6132. In the described embodiment, the lead wires for sensors 6118, 6117 may be disposed within the braided ribbon cable layer 6123 which may include ribbon cables bundled together and with individual microcoax wires 6152 of about 8 mils thickness. The braided wire sleeve 6134 runs longitudinally over the puller wire tubes 6133 and the braided ribbon cables layer 6135. Preferably, the braided wire sleeve is constructed of stainless steel. Finally, the above-described outer jacket 6127, preferably constructed of nylon, surrounds the braided wire sleeve layer 6134.

The catheter tip 6112 is steerable using the pair of puller wires 6121. To aid in steering, each of the puller wires is connected to a thumb slide 6170 which is slidably mounted on the outer surface of the handle, preferably proximate to its distal end (FIG. 6C). The pair of thumb slides are positioned opposite each other on the handle 6173.

Sliding of the thumb slides in the proximal direction relative to the catheter pulls on the puller wire to which it is connected and causes the catheter tip 6112 to deflect in a horizontal direction. The deflection is such that the catheter tip 6112 becomes concave on the side of the puller wire that was moved proximally. Reverse deflection of the catheter tip occurs by sliding the opposite thumb slide proximally relative to the guiding catheter. Deflection of the catheter tip 6112 may be used to alter the position of the sensors 6117, 6118 alter the divergent ultrasound beam produced for accurately characterizing the adjacent flow patterns. Bidirectional movement in a left-right horizontal plane is achieved using the thumb slides 6170 which are connected to puller wires 6121. As described, the catheter tip 6112 is capable of 1 to 4 movement degrees of freedom. In an embodiment having a single puller wire only a single thumb slide is needed.

Figure 6F:
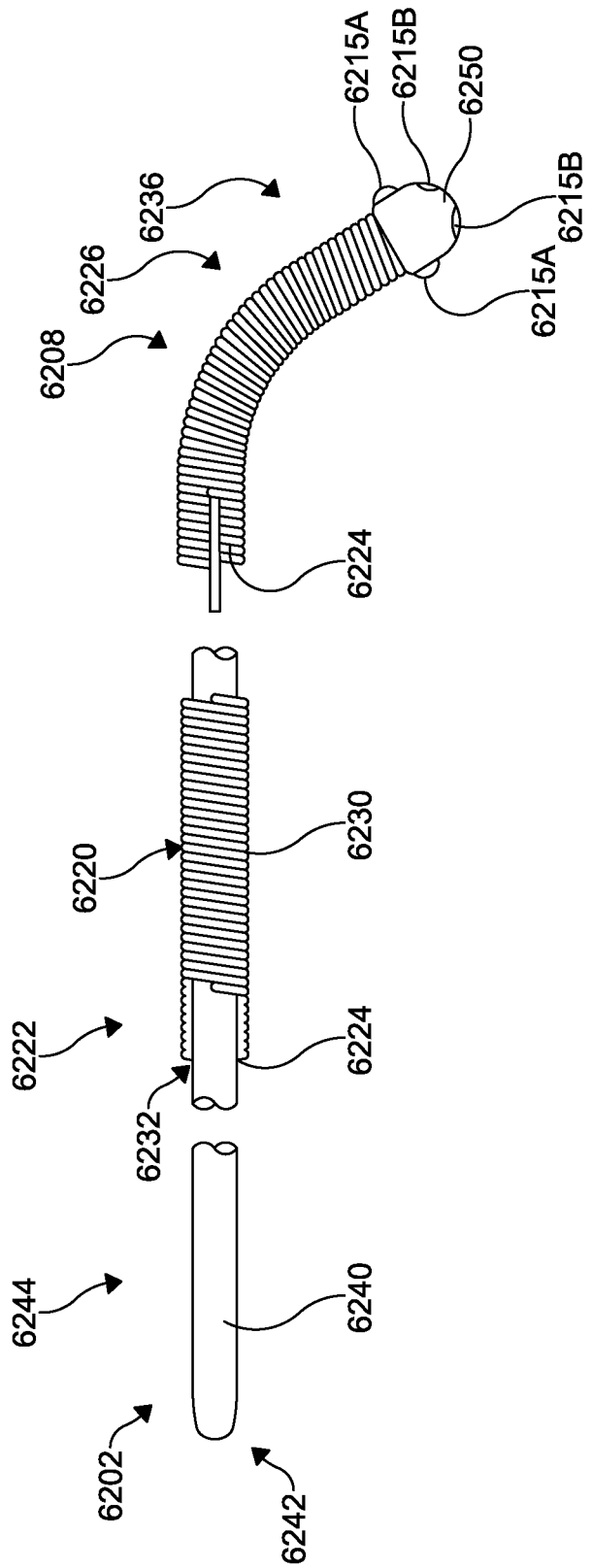
FIGS. 6F-G is a plan view of a distal portion of a guidewire in accordance with an exemplary embodiment of the present invention.

FIG. 6E is a plan view of a steerable guidewire 6200 having lateral sensors 6215A and forward looking sensors 6215B in accordance with embodiments of the present invention. FIG. 6F is a plan view of a distal portion of a guidewire in accordance with an exemplary embodiment of the present invention. Guidewire 6200 includes a distal end 6206, a distal portion 6208, and a proximal end 6202. Guidewire 6200 also includes a shaft assembly 6220 having a distal end 6226 and a proximate end 6222. As shown in FIG. 6E, shaft assembly 6220 includes a coil 6230 defining a lumen 6224 and a wire 6240 disposed in lumen 6224 of coil 6230. A distal end 6236 of coil 6230 is fixed to a tip member 6250. Likewise, a distal end 6246 (not shown) of wire 6240 is fixed to tip member 6250. Wire 6240 extends beyond a proximal end 6232 of coil 6230 forming a proximal portion 6244 of wire 140 terminating at a proximal end 142 of wire 140.

Wire 6240 of guidewire 6200 includes a curved portion 152 disposed proximate distal end 6206 of guidewire 6200. In the illustrated embodiment, curved portion 6252 of wire 6240 is shown in a substantially unbiased position. In the embodiment shown, coil 6230 is urged into a substantially curved shape by curved portion 6252 of wire 6240. The curved portion 6252 of wire 6240 is biased to return to a generally curved shape after being deflected. It may be appreciated that coil 6230 is comprised of a plurality of turns 6254. The longitudinal axis of coil 6230 is disposed along a generally curved path. The coil 6230 defines a plurality of gaps 6256 disposed between adjacent turns of coil 6230. Those of skill in the art will appreciate that curved portion 6252 of wire 6240 may have any radius of curvature depending upon need. Likewise curved portion 6252 may have any bend angle depending upon need.

Figure 6G:
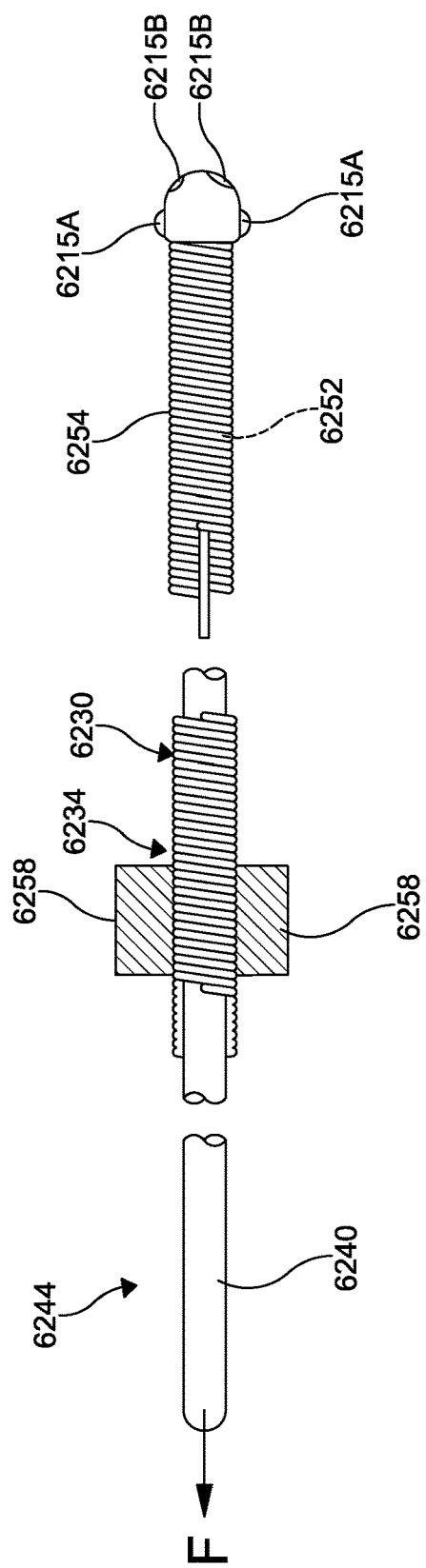

FIG. 6G is a plan view of guidewire 6200. In this embodiment, a plurality of grabbers 6258 are disposed about a proximal portion 6234 of coil 6230. Also illustrated is a force F is acting upon proximal portion 6244 of wire 6240. As described previously, curved portion 6252 of wire 6240 is biased to assume a generally curved shape. The application of force F to proximal portion 6244 of wire 6240 has urged turns 6254 of coil 6230 into close proximity with each other, and urged wire 6240 into a substantially straightened state. In use, for example, a physician could grasp proximal portion 6234 of coil 6230 with the thumb and index finger of his left hand. Also in this example, the physician could grasp proximal portion 6244 of wire 6240 with the thumb and index finger of his right hand. The physician could then urge proximal portion 6244 of wire 6240 proximally with respect to proximal portion 6234 of coil 6230.

In a method in accordance with the present invention, guidewire 6200 may be inserted into the vascular system of a patient and urged forward through the vasculature until tip member 6250 of guidewire 6200 is proximate a desirable target site as determined through use of the inventive guidance techniques described herein. As guidewire 6200 is advanced through the vasculature of a patent, it may be necessary to "steer" the guidewire. For example, the distal end of guidewire 6200 may reach a branch in the vasculature. The physician may direct the distal end of the guidewire toward the desired branch of the vasculature based on feedback provided by processing the data acquired by sensors 6215A, 6215B. Curved portion 6208 of guidewire 6200 may facilitate the steering process. Torsional forces may be applied to the proximal portion of guidewire 6200 to alter the angular orientation of curved portion 6252 relative to the blood vessel. In this manner, the distal end of guidewire 6200 may be directed to place the sensors 6215A, 6215B into a different orientation within a vessel for the acquisition and processing of additional sensor data to aid in guiding guidewire 6200. Once guidewire 6200 is positioned within the vasculature, the proximal end 6202 of guidewire 6200 may be inserted into a guidewire lumen of a catheter (not shown). The tip of the catheter may be advanced along the length of the guidewire until it reaches a desirable target site. In this manner, guidewire 6200 may aid a physician in delivering the distal tip of a catheter to a desired target site, in particular target sites identified using the ultrasound signal processing techniques described herein.

The term "wire", as used in describing wire 6240 and elsewhere in this application should not be mistaken as limiting wire 6240 to elements having a circular cross section. The cross section of wire 6240 may be any number of shapes. For example, the cross section of wire 6240 could be rectangular, elliptical, etc. Likewise, the term "wire", as used in describing wire 6240 should not be mistaken as being limited to metallic materials. In fact, wire 6240 may comprise many metallic and non-metallic materials. Examples of metallic materials which may be suitable in some applications include stainless steel, tantalum, and titanium. Wire 6240 may also include a nickel-titanium alloy known in the art as Nitinol. Nitinol is commercially available from Memory Technologies (Brookfield, Conn.), TiNi Alloy Company (San Leandro, Calif.), and Shape Memory Applications (Sunnyvale, Calif.). Examples of non-metallic materials which may be suitable in some applications may be found in the list immediately below which is not exhaustive: polycarbonate, poly(L-lactide) (PLLA), poly(D,L-lactide) (PLA), polyglycolide (PGA), poly(L-lactide-co-D,L-lactide) (PLLA/PLA), poly(L-lactide-co-glycolide) (PLLA/PGA), poly(D, L-lactide-co-glycolide) (PLA/PGA), poly (glycolide-co-trimethylene carbonate) (PGA/PTMC), polyethylene oxide (PEO), polydioxanone (PDS), polycaprolactone (PCL), polyhydroxylbutyrate (PHBT), poly (phosphazene), polyD,L-lactide-co-caprolactone) (PLA/PCL), poly(glycolide-co-caprolactone) (PGA/PCL), polyanhydrides (PAN), poly(ortho esters), poly(phosphate ester), poly(amino acid), poly(hydroxy butyrate), polyacrylate, polyacrylamid, poly(hydroxyethyl methacrylate), polyurethane, polysiloxane and their copolymers. Additionally, guidewire 6200 may also include a wire 6240 having a tubular cross section. For example, wire 6240 may comprise Nitinol hypodermic tubing.

Processing System

Examples of ultrasound control systems are described in the following patents: related to ultrasound imaging U.S. Pat. No. 6,896,658 to Ji et al. for Simultaneous multi-mode and multi-band ultrasonic imaging; U.S. Pat. No. 6,251,073 to Imran et al. for Miniaturized ultrasound apparatus and method; U.S. Pat. No. 5,492,125 to Kim et al. for Ultrasound signal processing apparatus; U.S. Pat. No. 6,561,979 to Wood et al. for Medical diagnostic ultrasound system and method; and U.S. Pat. No. 5,477,858 to Norris et al. for Ultrasound blood flow/tissue imaging system; related to Doppler ultrasound U.S. Pat. No. 4,324,258 to Huebscher et al. for Ultrasonic doppler flowmeters; U.S. Pat. No. 4,143,650 to Hatke for Directional doppler ultrasound systems for biosignal acquisition and method of using the same; U.S. Pat. No. 5,891,036 to Izumi for Ultrasonic wave Doppler diagnosing apparatus; related to guidance U.S. Pat. No. 5,220,924 to Frazin for Doppler-guided retrograde catheterization using transducer equipped guide wire; U.S. Pat. No. 6,704,590 to Haldeman for Doppler guiding catheter using sensed blood turbulence levels; U.S. Pat. No. 5,311,871 to Yock for Syringe with ultrasound emitting transducer for flow-directed cannulation of arteries and veins; U.S. Pat. No. 6,612,992 to Hossack et al. for Medical diagnostic ultrasound catheter and method for position determination related to tracking method U.S. Pat. No. 5,785,657 to Breyer et al. for Blood flow measurement device; and related to pressure estimation U.S. Pat. No. 5,749,364 to Sliwa Jr. et al. for Method and apparatus for mapping pressure and tissue properties.

Figure 25:
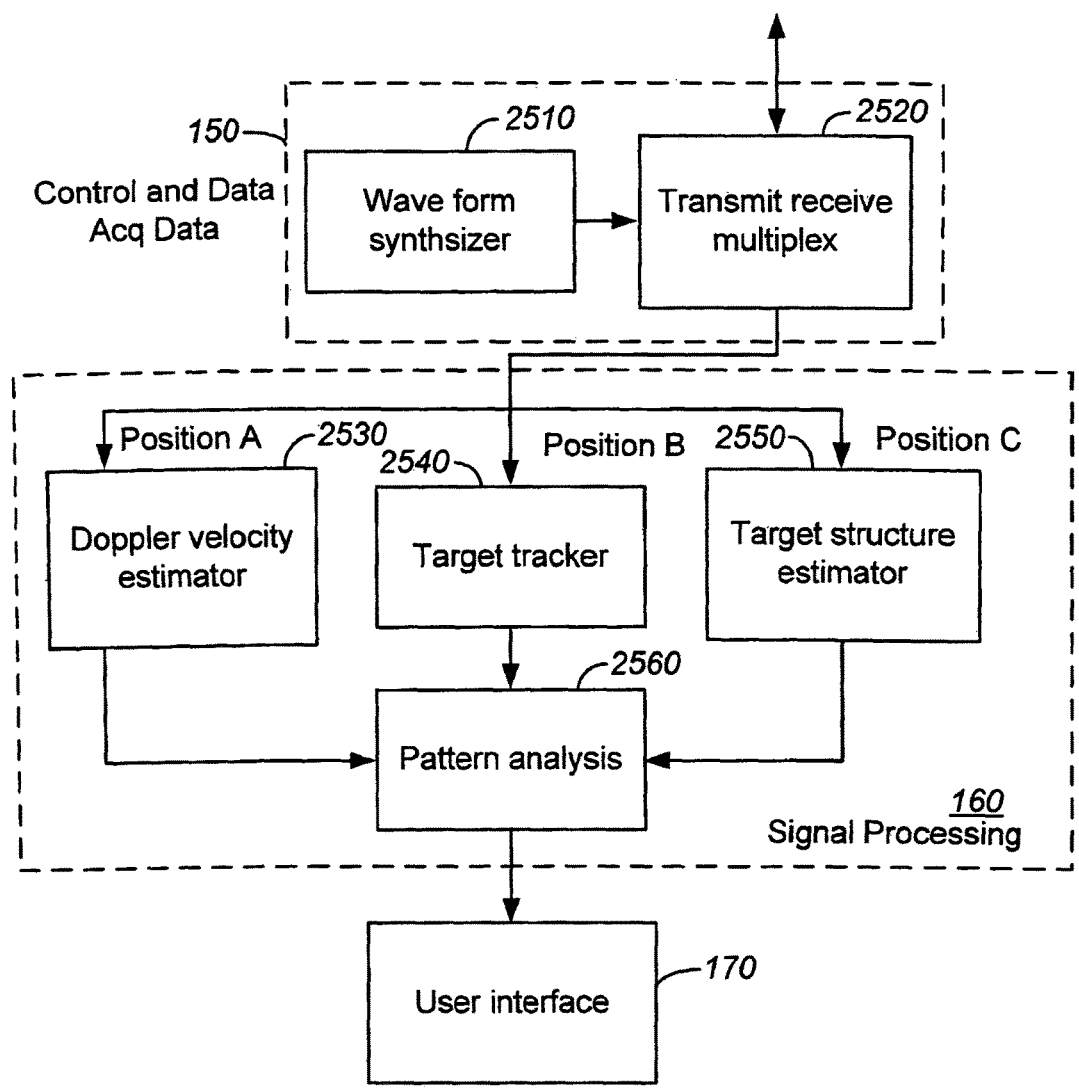
FIG. 25 illustrates a block diagram of additional components within a control and acquisition unit.

FIG. 25 illustrates a more detailed block diagram of additional components within the control and data acquisition unit 150 and the signal processing unit 160 introduced in FIG. 2. As illustrated in FIG. 25, the control and data acquisition unit 150 includes a waveform synthesizer 2510 and a transmit and receive switch and a multiplexer 2520.

Figure 32:
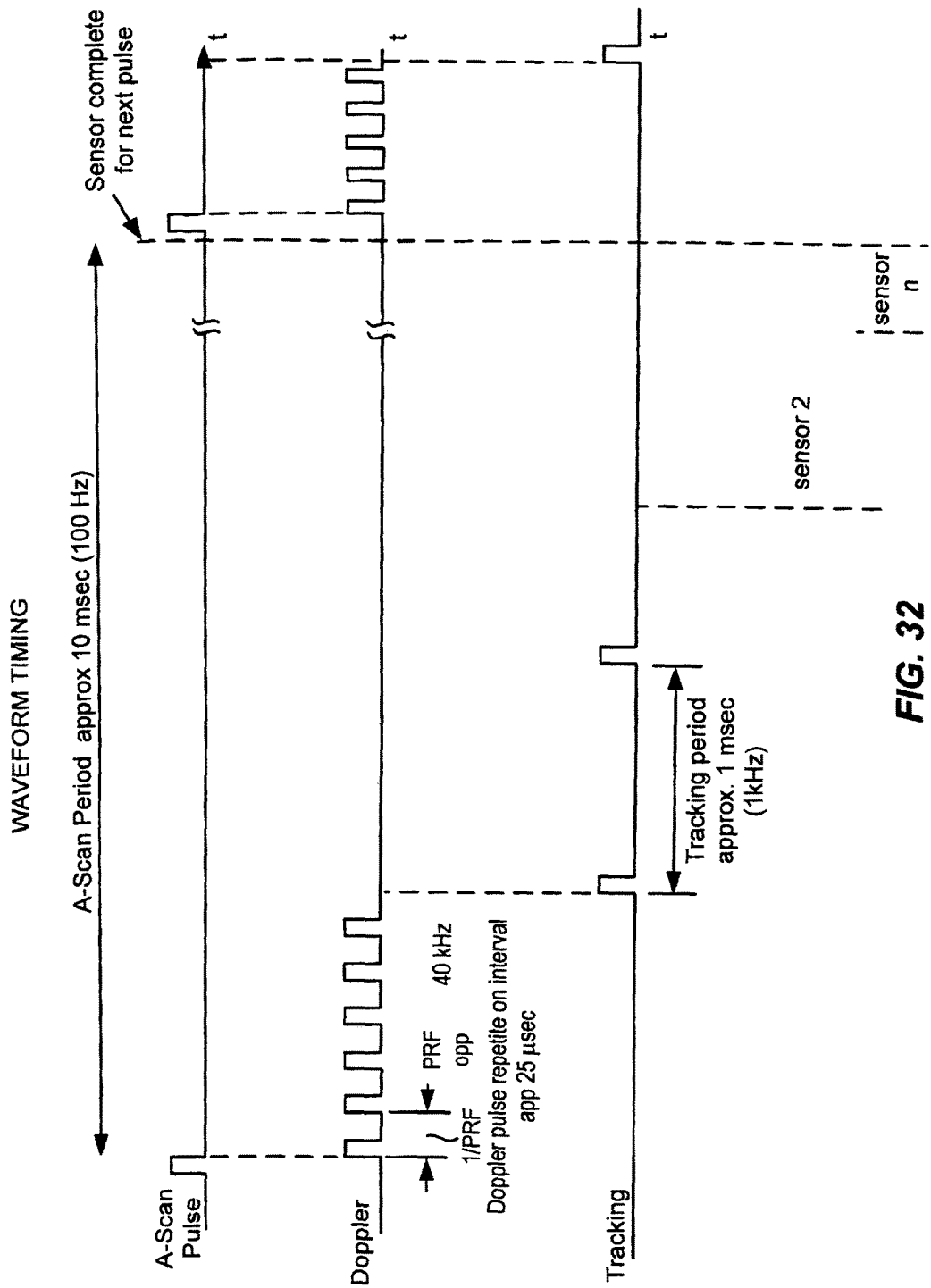
FIG. 32 illustrates electronic pulses generated by a waveform synthesizer wherein each sensor can be driven in real-time in a sequence of operating modes.

The waveform synthesizer 2510, such as a programmable pulse sequence generator or the like, is used to generate electronic signals, such as electronic pulses in FIG. 32, that are used to drive ultrasound sensors 115. The electronic signals are individually delayed as their sequence is programmed to generate the sequences shown in FIG. 32 depending upon what mode of processing is determined by the system control logic.

The output of the wave synthesizer is coupled to a power amplifier included in the transmitter block 2520, such as a power amplifier, high speed FET, or the like where it is amplified and passed through a transmit/receive switch. The transmit and receive switch 2520 sends/receives signal data to and from the sensor(s) in the system and provides that acquired data to the components of the signal processing unit 160. Transmit/receive switch optionally includes a multiplexer configured to couple the signals from the waveform generator to the desired sensor and the desired sensor to the corresponding signal processing path in block 160. The ultrasound sensor 115 generates a single divergent ultrasound beam by transforming the electrical energy from the power amplifier into mechanical acoustical waves of frequencies between 5 and 15 MHz.

The sensor 115 is configured to transmit an ultrasound beam into a material under investigation. Echoes are generated in the material under investigation through the interaction between the single divergent ultrasound beam and back scattering objects such as blood or reflective objects such as blood vessel or heart walls. The sensor 115 receives the generated echoes and produces corresponding electrical signals by transforming the high frequency ultrasound mechanical wave into electrical energy. These electrical signals are received through the transmit/receive switch and multiplexed into the desired signal path by the block 2520.

The signal processing unit 160 receives the electrical signals representing ultrasound echoes from the multiplexer 2520 and distributes them to a processing path according to the mode selected by the mode control logic 2702. The processing path includes a Doppler velocity estimator 2530 for providing blood velocity and direction information used in determining direction and position. The signal processing unit 160 includes a target tracker 2540 for providing information about the movement of slow moving targets including vessel walls and blood clusters at low speeds. The signal processing unit 160 includes a target structure estimator 2550 for determining whether the sensor is in contact with the wall. The structure estimator 2550 is also used to provide information about the wall proximity and to estimate the blood vessel inner diameter. As indicated, outputs from the Doppler velocity estimator 2530, target tracker 2540 and the target structure estimator 2550 all received into the pattern analysis block 2560. The pattern analysis block estimates the blood pressure gradient from velocity gradient and vessel inner diameter information, determines the blood flow pattern and estimates the signature pattern of an ultrasound object of interest including a location within the blood vessel.

Figure 26:
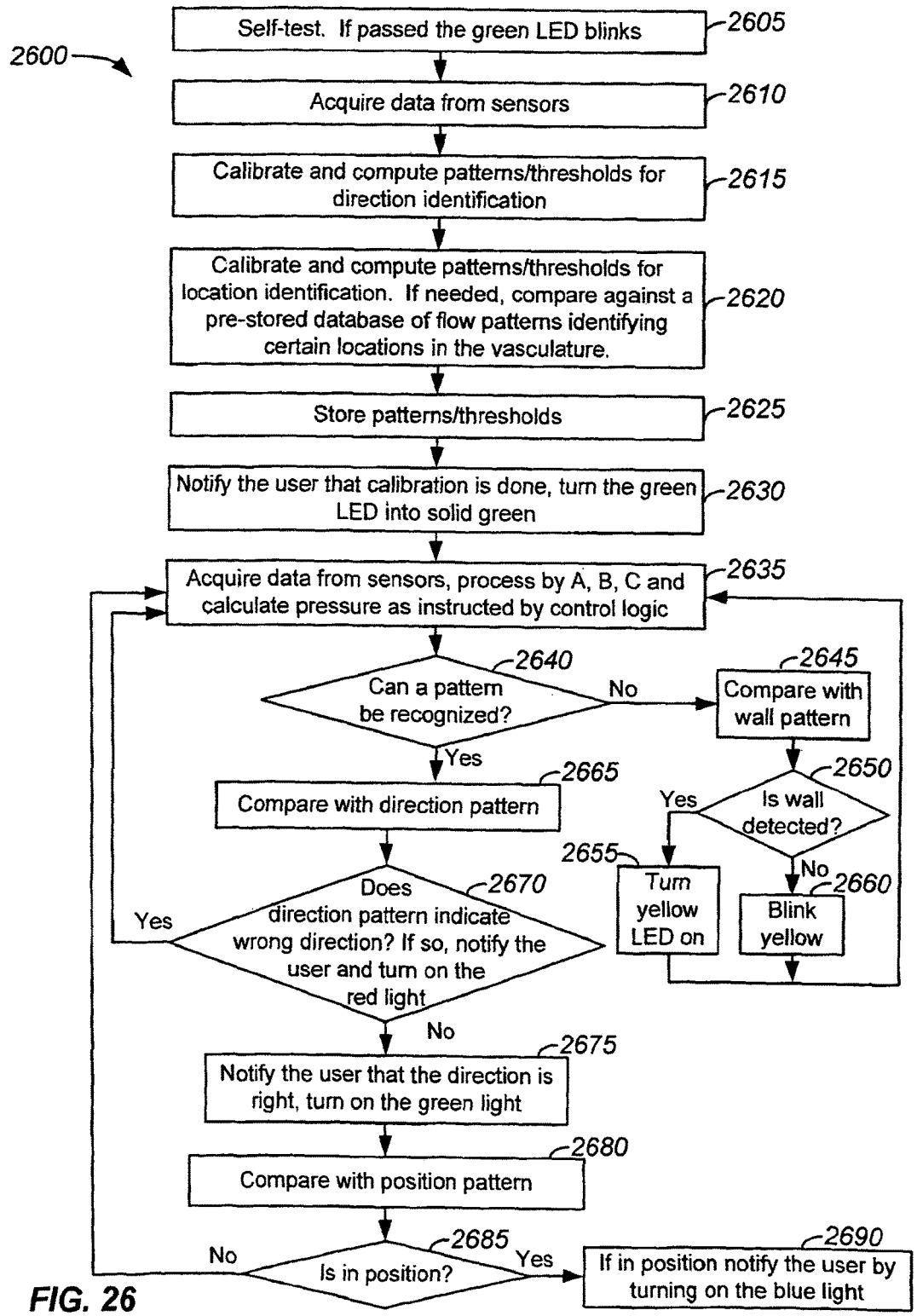
FIG. 26 illustrates a flow chart of an algorithm implemented by a multi-single beam ultrasound system.

FIG. 26 illustrates a flow chart "2600 that illustrates an embodiment of a guiding algorithm implemented by multi-single beam ultrasound system. First, at step 2605, initiate self-test. If the sensor and system passes, the green LED will blink.

Next, at step 2610, the system will acquire data from the sensors. As shown, there may be one or more single beam sensors under control of the control and data acquisition unit. Next, at step 2615, calibrate and compute patterns/thresholds for direction identification.

Next, at step "2620, calibrate and compute patterns/thresholds for location identification. If needed, compare against pre-stored database of flow patterns identifying certain locations in the vasculature. Thereafter, at step 2625, store the patterns/thresholds.

Next, at step 2630, the system will provide an indication to the user to notify the user that calibration is done by turning the green LED into a solid green light.

After completing calibration, the next step 2635, is to acquire data from the sensor or sensors in the system. The acquired data is processed using one or more of the Doppler velocity estimator, the target tracker and the target structure estimator and calculate pressure as instructed by the system control logic.

Next, at step 2640, the acquired data undergoes pattern analysis to determine whether the data from the sensors contain a pattern that can be recognized by the system. If the result in step 2640 is NO indicating that a pattern cannot be recognized, then the system will proceed to step 2645 to compare the sensor date with the data provided by the target structure estimator to determine whether the sensor is against the vessel wall.

If the result of step 2650 is "Yes" and the wall is detected by the system, the yellow LED will illuminate to notify the user that the sensor is against the wall. Next, the system returns to step 2635 and acquires data from sensors.

If the result of step 2650 is "No" and neither the earlier processing steps nor the wall pattern match, then the system us unable to determine the location of the sensor, and the yellow LED will blink yellow to indicate to the user that the system is unable to determine the sensor location. Next, the system returns to step 2635 and acquires data from sensors.

If the result in step 2640 is YES indicating that a pattern in the sensor data can be recognized, then the system will proceed to step 2665 to compare the sensor data with the direction pattern. If the result of the query in step 2665 is YES that the sensor data indicates that wrong direction of travel, then notify user by illuminating the red LED. Thereafter, the system returns to step 2635 and acquires data from the sensor to determine whether the wrong direction indication can be cleared.

If the result in step 2640 is NO indicating that the direction pattern comparison indicates that the sensor is moving in the proper direction, then the green LED will be illuminated to notify that the current direction of catheter advancement is the correct direction of catheter advancement.

Next, the sensor data is compared to the position pattern (step 2680). If the result of that comparison is NO the catheter is not in position, then the system returns to processing at step 2685 and acquires data from the sensors.

If the result of that comparison in step 2680 is YES the catheter is in position, then the system continues to step 2690 and notifies the user that the sensor is in the proper position and illuminates the blue light.

Figure 27:
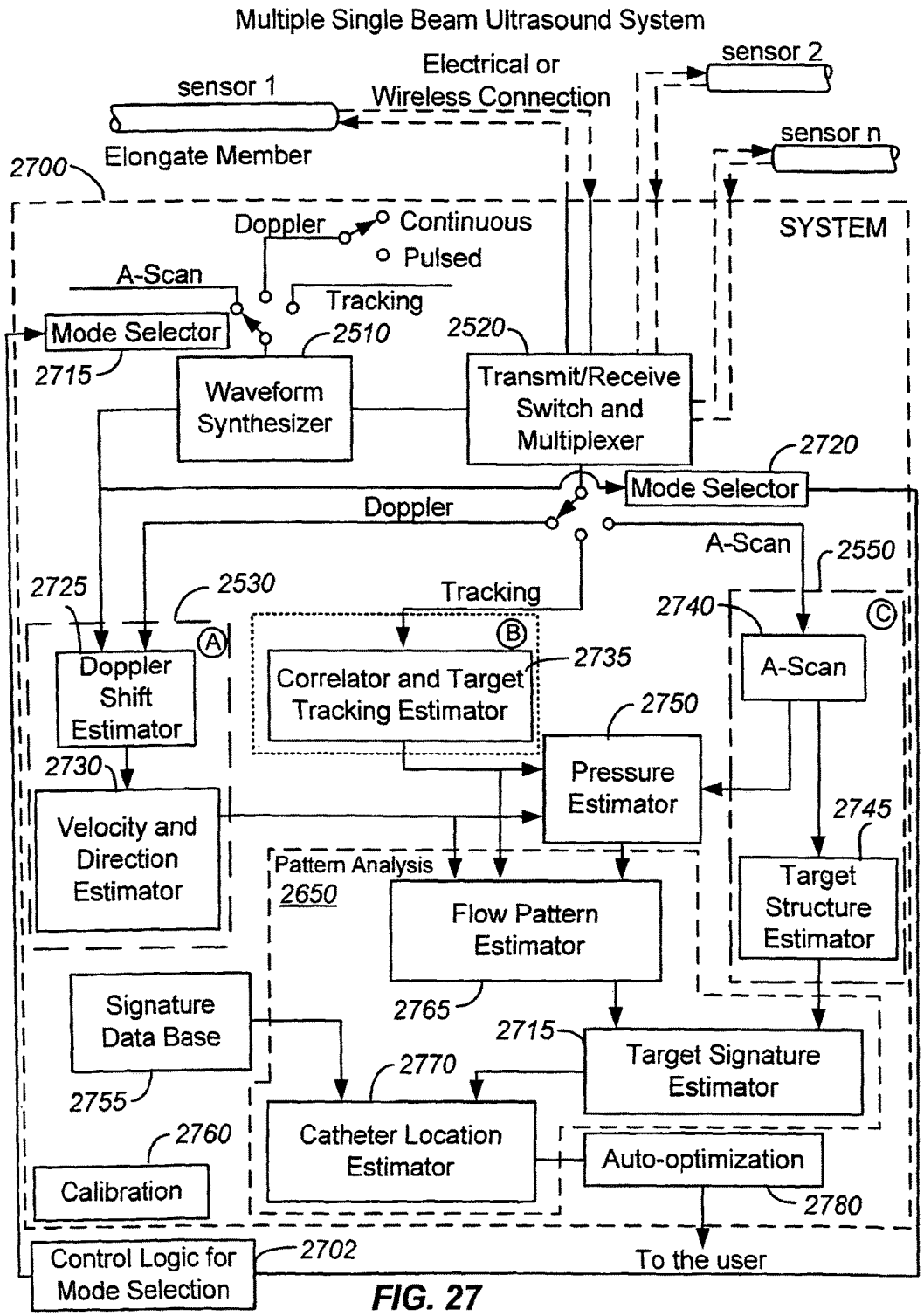
FIG. 27 illustrates a block diagram of an embodiment of a multi single beam ultrasound system.

FIG. 27 illustrates a block diagram of an embodiment of a multiple single beam ultrasound system 2700. The system consists of a mode selector 2715 which allows for the selection of one of the following operating modes: A-Mode or A-Scan, Doppler continuous wave (CW) or pulsed wave (PW), and target tracking or simply tracking. The modes can be selected individually or in sequence for each of the connected sensors through the control logic 2702. The waveform synthesizer generates excitation pulses for the sensors according to the scheme or sequence programmed by the control logic 2702. The transmit/receive switch 2520 switches the electrical paths between the system and the sensors between transmit and receive modes. The multiplexer 2520 multiplexes the use of the system among multiple sensors. The mode selector 2720 selects the signal processing path as programmed by the control logic 2702. Three signal processing paths are available which can be use independently or in any combination: Doppler processing 2725 for blood velocity and direction estimation 2730, target tracking 2735 for estimating slow movement of blood and other targets of interest, and A-Mode or A-scan 2740 for target structure estimation 2745. Pressure 2750 may be calculated using any of a number of conventional techniques where pressure is calculated using velocity information. One such technique is described in U.S. Pat. No. 5,749,364, the entirety of which is incorporated herein by reference. The pattern analysis and recognition engine 2650 estimates blood flow patterns 2765, target signatures 2775 and finally the location of the distal tip in the vasculature using 2770. Database information 2755 is used to compare detected patterns. A calibration block 2760 performs in-vivo patient specific system calibration. The auto-optimization block 2780 performs context dependent adjustment of system settings. The control logic for mode selection 2702 selects the operating mode or sequence of modes base on user input and current system settings.

Figure 33A:
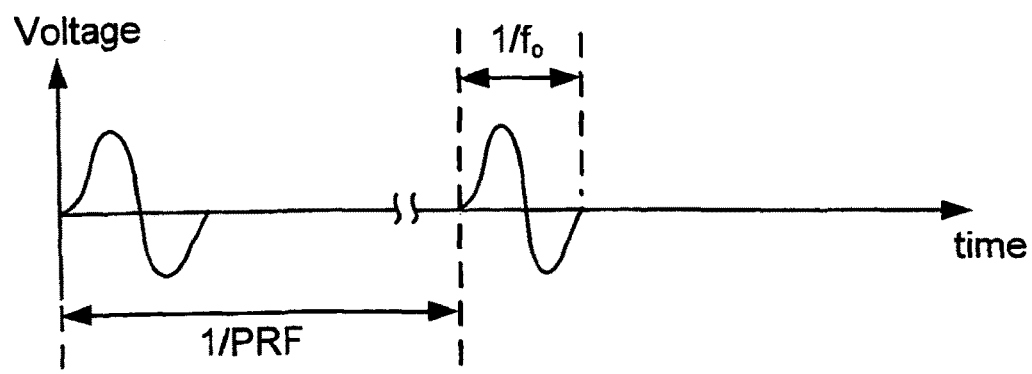
FIG. 33A illustrates a single pulse waveform at an operating frequency.
Figure 33B:
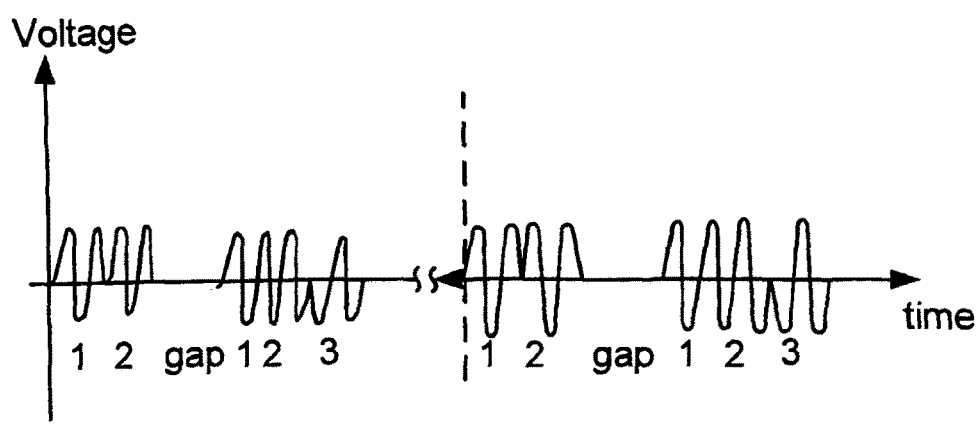
FIG. 33B illustrates a coded excitation.

The waveform synthesizer 2510 generates the excitation waveform for the sensors. The waveform depends on the operating mode: A-scan, Doppler, tracking and can be selected according to the desired mode. Any combination of operating modes can be selected at any given time. FIG. 32 shows that n sensors can be driven in real-time, whereby each sensor is driven in a sequence of operating modes. As illustrated in FIG. 32, sensor A is first driven by a pulse that periodically generates an A-scan. In the preferred embodiment an A scan is generated every 10 ms. If an additional sensor is present, the additional sensor can be immediately driven with a Doppler pulse sequence fired at a frequency called pulse repetition frequency (PRF). In the preferred embodiment the PRF is 40 KHz. If only one sensor is driven in both A-scan and Doppler modes, the Doppler pulse sequence can only be fired after 1/PRF delay after the A-scan pulse. After at least 1/PRF delay after the last Doppler pulse was fired, the sensor can be fired again in order to obtain tracking information. The tracking mode requires two pulses fired in sequence at different moments in time. In the preferred embodiment shown in FIG. 32 the delay between the two tracking pulses is approximately 1 ms. After all modes have been fired in sequence for one sensor, the next sensor can be excited in the same or a different sequence. Further all sensors can be excited and the sequence starts again from the first sensor. Any combination of excitation pulses is possible between the different modes and the different sensors. For example sensor 1 can be excited in tracking mode and sensor 2 can be excited in tracking mode immediately thereafter. In such a sequence, angle independent velocity measurements can be made. Further examples of parametric waveform generation are given in the following patents each of which is incorporated herein for reference in its entirety: See, U.S. Pat. No. 6,896,658 to Ji et al for Simultaneous multi-mode and multi-band ultrasonic imaging and U.S. Pat. No. 6,551,244 to Gee for Parametric transmit waveform generator for medical ultrasound imaging system The waveform synthesizer 2510 also allows for coded excitation. The coded excitation in FIG. 33 provides increased penetration depth for a larger sample volume. It allows for better contrast resolution which helps the tracking (correlation) algorithms with the detection of blood flow. FIG. 33A illustrates a single pulse waveform at the operating frequency. In the preferred embodiment the preferred frequency f0 is 10 MHz, 33B illustrate a coded excitation. At the same operating frequency, a sequence of pulses of positive or negative polarity is generated. In the preferred embodiment the sequence consists of 2 positive polarity pulses followed by a gap followed by one positive and 2 negative polarity pulses. U.S. Pat. No. 6,213,947 to Phillips for Medical diagnostic ultrasonic imaging system using coded transmit pulses describes an alternative method of coded excitation.

The Transmit/Receive Switch and Multiplexer 2520 are of conventional art. This functional block multiplexes the signal path alternatively to all connected sensors. In pulsed mode it also switches the signal path to the sensor between transmitting and receiving. Such functionality is described in U.S. Pat. No. 6,896,658 to Ji et al. for Simultaneous multi-mode and multi-band ultrasonic imaging and is incorporated herein in its entirety for reference.

Figure 31:
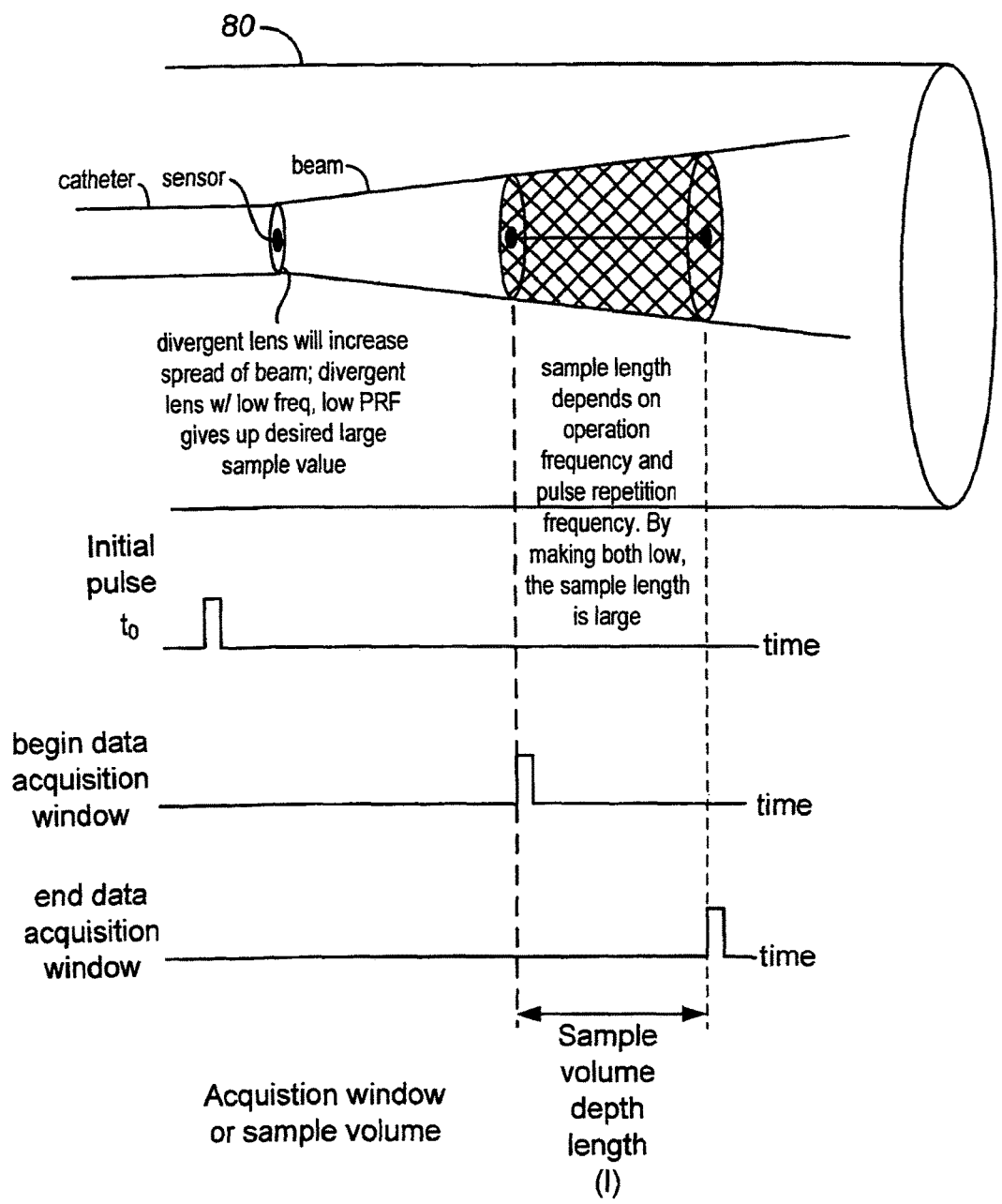
FIG. 31 illustrates some specific properties of an ultrasound beam generated by a sensor as a result of excitation.

FIG. 31 illustrates the specific properties of the ultrasound beam generated by the sensor as a result of the excitation according to the present invention. As illustrated in FIG. 5, the sensor and the elongate member are optimized to generate the largest beam possible, i.e., the largest diameter possible in FIG. 31. In order to maximize the volume of analyzed target with a given beam, the length of the volume is maximized as well. The volume of the target of interest is defined as the three dimensional region encompassed by the beam geometry and contained in the acquisition window. The maximum sample volume depth length or the length of the acquisition window is determined by two parameters: the operating frequency and the pulse repetition frequency. The operating frequency determines the depth of penetration of ultrasound in tissue. In a preferred embodiment the operating frequency is approximately 10 MHz. This allows for a maximum depth of penetration of approximately 20 mm. At 20 MHz the penetration depth is only 3-5 mm, which is insufficient to analyze venous flow in large veins of 10-20 mm inner diameter. The pulse repetition frequency in the preferred embodiment of the current invention is approximately 40 KHz. This allows the ultrasound wave to penetrate deep enough for venous flow between two pulses. It also allows to calculate the relevant Doppler velocities for venous flow. In arterial flow the pulse repetition frequency (PRF) must be around 100 KHz in order to capture the high velocities of arterial flow. A PRF of 100 KHz, i.e., pulse repetition interval of 1/PRF does not allow the ultrasound beam to travel deep enough between two pulses in order to generate a large enough sample volume.

Figure 28:
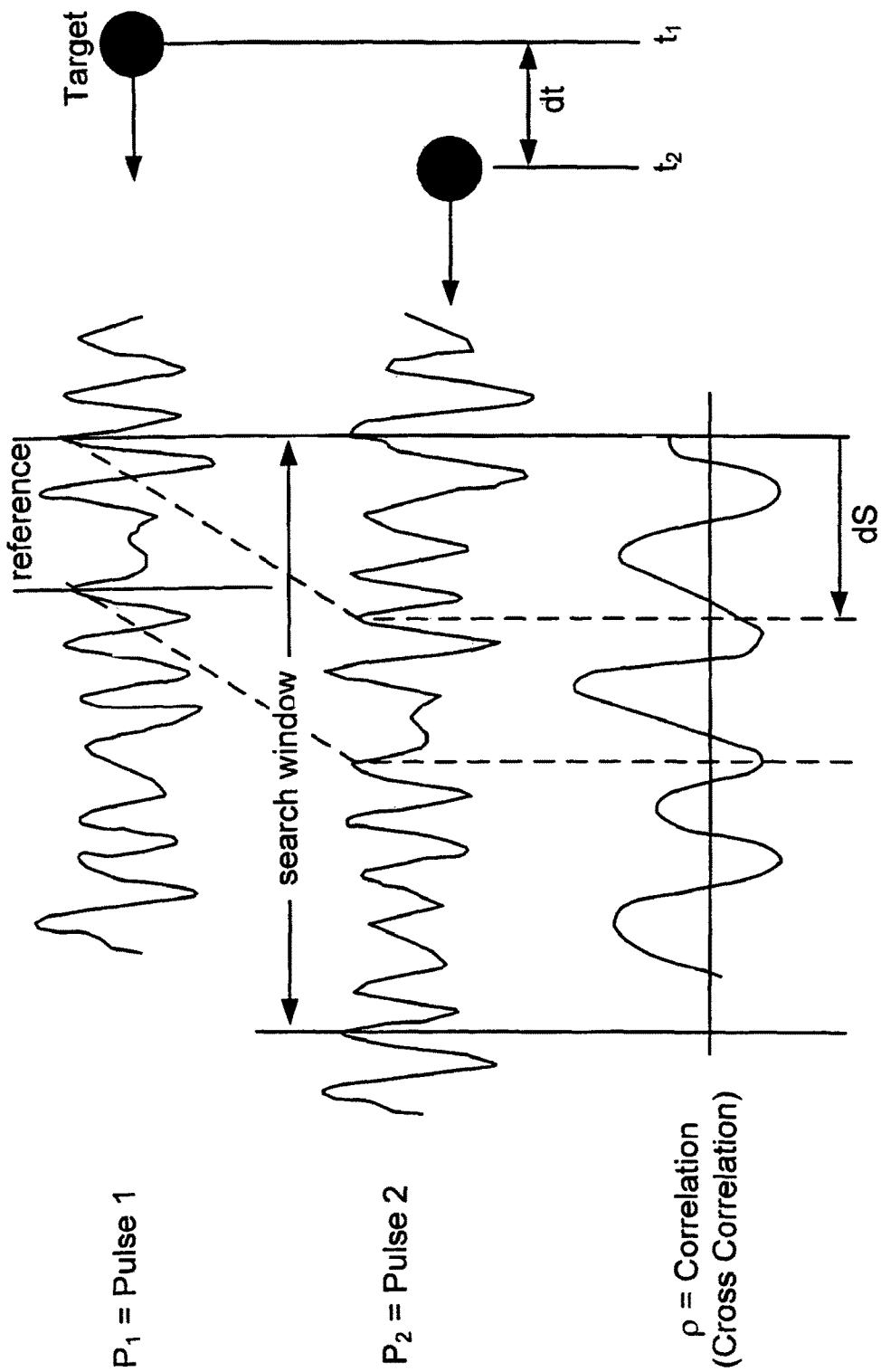
FIG. 28 illustrates the use of correlation methods in a tracking algorithm to target velocity.

The functionality of the Target Tracking block 2735 is also known as "Cross-Correlation", "Autocorrelation", and "Correlation" methods. The proposed tracking algorithm is based on the idea of following a target in time, e.g., a blood cell or cluster and detect its position at two distinct moments in time. By determining the distance traveled by the target between the two moments in time, the target velocity can be calculated. This concept is illustrated in FIG. 28. Assume that at moment $t_1$ the system receives ultrasound echoes from the target volume and at moment $t_2$ receives different echoes from the same target volume. The system uses the signal processing techniques of cross-correlation to match specific echo patterns at moment $t_1$ against echo patterns at moment $t_2$. When the patterns match, it is said that they are correlated. Velocity estimation is another result available from the cross-correlation analysis because that analysis determines the distance between matched patterns. Assuming that matched patterns represent the same target, the estimated velocity of that specific target can be calculated from the time difference and the distanced traveled. Turbulence estimation refers to another result of the cross-correlation analysis where the amount by which a target echo pattern has changed from one moment to the next. The more correlation exists, the more laminar the flow because of the lesser changes between the moments. Lesser correlation indicates more turbulent flow.

Figure 29:
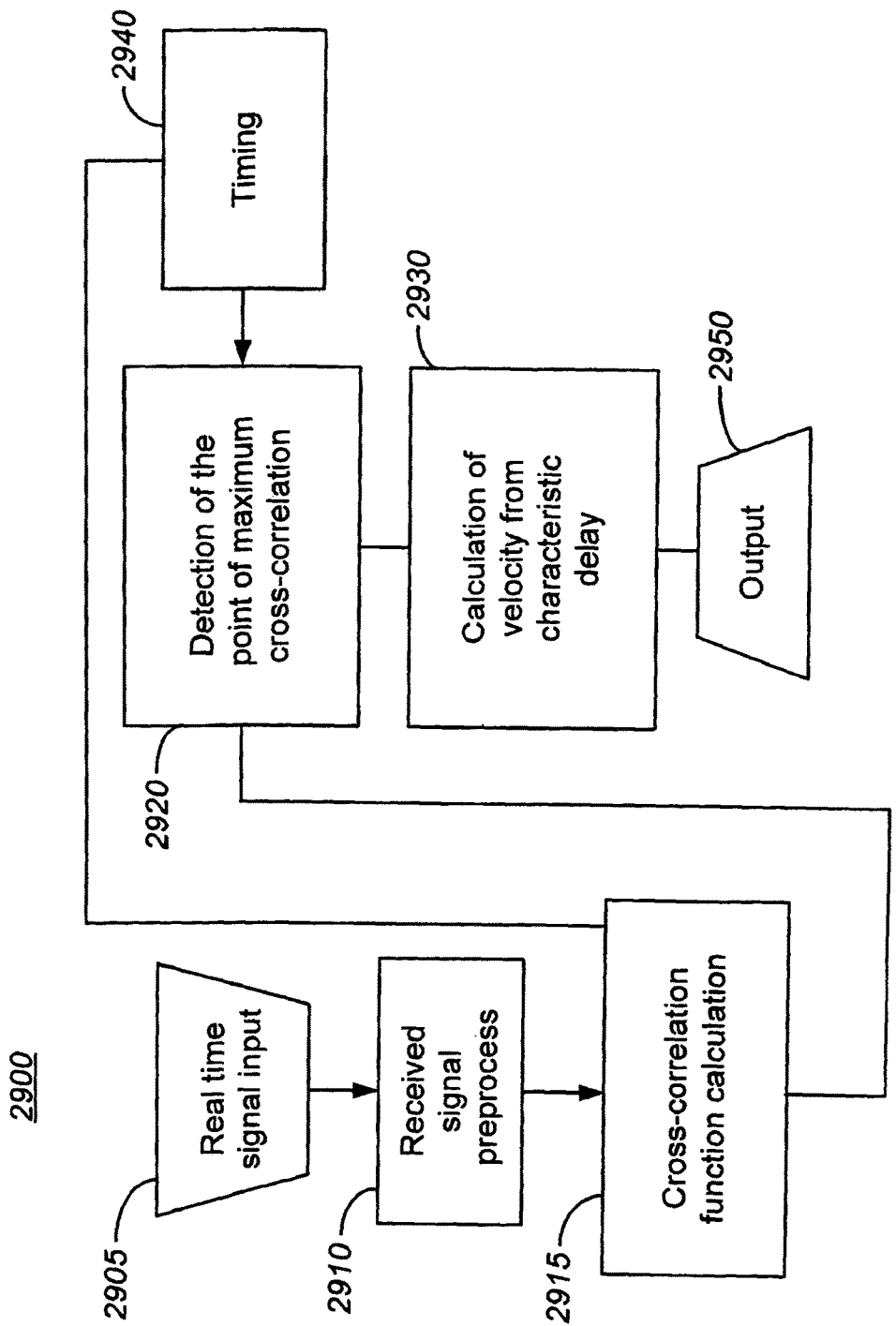
FIG. 29 illustrates a preferred embodiment of a tracking method for processing a real time signal input.

FIG. 29 illustrates a preferred embodiment for the tracking method 2900. The signal from the sensor is input in real time through the block 2905 which contains an input data buffer with memory, preferably a double ping-pong buffer with a memory of at least two A-scans. The received signal is preprocessed by 2910 to remove noise and rescaled to a predetermined value in order to facilitate cross-correlation computation. Block 2915 computes the cross-correlation function using a programmable window as illustrated and described above in FIG. 28. Block 2920 determines the characteristic point on the delay axis, i.e., the point of maximum correlation. Assuming the speed of sound is approximately 1540 m/s in human tissue including blood the distance ds from FIG. 28 corresponding to the delay of maximum correlation can be calculated. Block 2930 calculates the speed of the target from the value ds and from the delay dt between the two A-scans under analysis. The timing block 2940 synchronizes the cross-correlation computation with the waveform synthesizer 2510 (FIG. 27). The output of the velocity estimation is directed by 2950 to the pressure estimator block 2750 (FIG. 27) and to the flow pattern estimator 2765 (FIG. 27).

Unlike Doppler methods that depend on the angle between the probe or sensor and the blood flow, the tracking methods described herein are angle independent. Angle independent tracking provides the ability to better detect locations in the vasculature independent of what the relative tip position is with respect to the vessel wall. Angle independent tracking also provides a technique to separate lower velocities from desired targets (i.e., blood) from lower velocities from undesired ones (i.e., vessel wall motion artifacts). Conventional Doppler techniques do not allow such a separations or distinctions in low velocity tracking. The angle independent tracking techniques of the inventive method rely on volumetric indications, not punctual indications as used in Doppler processing. With other words, the angle independent tracking techniques of the inventive method obtain and provide information from a larger sample volume of blood flow free of the sample volume size limits imposed by the Doppler processing methods.

Returning to FIG. 27, the pressure estimator 2750 estimates the blood pressure gradient as the device with sensor advances through the vasculature. The pressure is estimated from the blood velocity gradient as determined by either Doppler or target tracking methods and from an estimation of the blood vessel inner diameter. In one embodiment the blood vessel inner diameter is either retrieved from a database based on the relative location of the sensor in the vasculature. In another embodiment, one of the sensors perpendicular to the direction of device advancement is used in A-mode to estimate vessel wall proximity and vessel inner diameter. Pressure may also be calculated using any of a number of conventional techniques where pressure is calculated using velocity information. One such technique is described in U.S. Pat. No. 5,749,364 to Sliwa Jr. et al. for Method and apparatus for mapping pressure and tissue properties. One advantage of using the sensors of the present invention to obtain/measure pressure is the avoidance of the conventional pressure estimation technique that relies on the injection of contrast medium.

Figure 30:
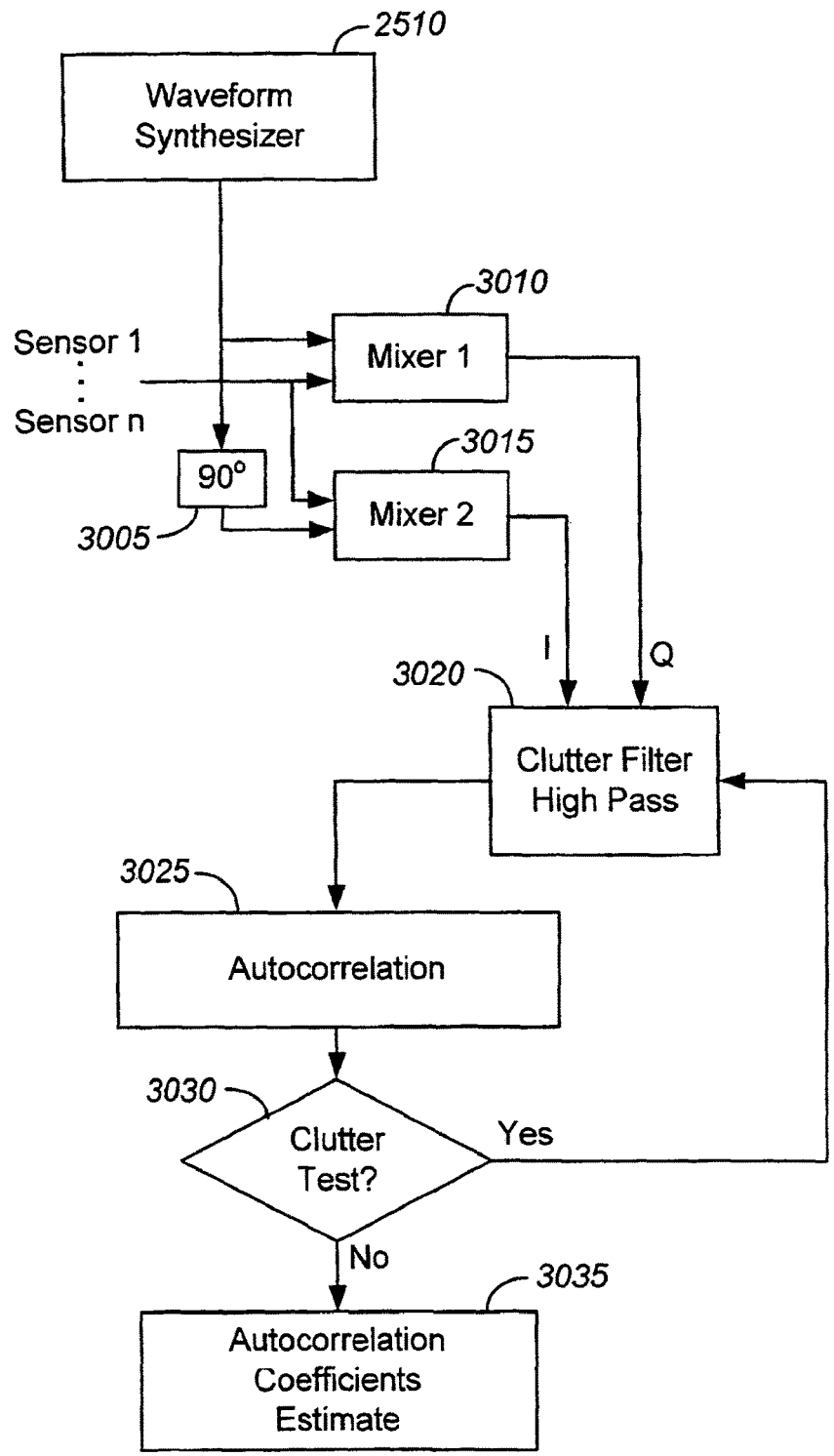
FIG. 30 illustrates an embodiment having a waveform synthesizer.

Continuing in FIG. 27, the Doppler shift estimator 2725 estimates the Doppler shift as described by FIG. 30. The velocity and direction estimator 2730 uses the Doppler shift to calculate velocity, and spectral power. The velocity and the spectral power are then used by the pressure estimator 2750 to estimate pressure gradients and by the flow pattern estimator 2765 to determine the flow pattern and its trends. A signal of ultrasound frequency is transmitted into the blood vessels. Let this frequency component be given by f0. In the preferred embodiment of this invention f0 is approximately 10 MHz. The back-scattered echo from the blood vessels contains frequency component shifted by an amount directly proportional to the blood velocity. If the shift in frequency is given by $\Delta f$, and the corresponding velocity of the blood flow by v, then $\Delta f = k*v$, where k is a constant. Thus the back-scattered signal contains frequency component ($f0 \pm \Delta f$). The sign of the shift is determined by the direction of blood flow. In a continuous wave ultrasonography signal, the shift in frequency is not due to only one blood velocity component. Instead it is a contribution of a number of velocity components. Thus instead of a single frequency shift, there is a band of frequencies in the shifted component. This signal is detected in the time domain and Fourier transform is computed to generate the frequency domain signal. The frequency shift indicative of the blood velocity can be analyzed in the time domain using the zero crossing counter technique. In the frequency domain, the frequency shift can be calculated using the Fourier analysis.

In the embodiment illustrated in FIG. 30, the waveform synthesizer 2510 provides the excitation pulses to one or more of the sensor described herein. And to the mixer 3015 through a 90 degrees phase shift block 3005. The ensemble mixer 3010, mixer 3015, and "90° shift" block 3005 provide a quadrature demodulation of the received signal. The quadrature demodulated signals correspond to the direct (away from a sensor) and reverse (toward a sensor) velocities. The phase detectors compute the phase shift in this two signals which is indicative of the blood velocity. The outputs of mixers 3010 and 3015 go to a high filter optimized for removing "clutter" from the signal. In this instance, clutter is defined as low velocity/high intensity movements, e.g., the movements of a vessel wall. Low velocity/high intensity movements interfere with accurate Doppler algorithm processing and are therefore removed. For adaptive removal of clutter, the auto-correlator (block 3025) may be used. During adaptive removal of clutter, the auto-correlator processes the acquired data using an autocorrelation function to determine if a clutter pattern is present or not. If processing the acquired data using an autocorrelation function determines that clutter is present (i.e., block 3030 is YES), then the clutter filter is turned on and the loop repeats until the clutter is reduced below a certain threshold. In this case, the signal and the autocorrelation coefficients are passed further to the velocity and detection estimator 2730 (FIG. 27). The velocity and detection estimator 2730 calculates the Doppler frequency and spectral power from the clutter free signal generated by the correlator and target tracking estimator 2735.

Clutter removal removes low velocity/high intensity information so as not to diminish the accuracy of Doppler measurements. However, low velocity/high intensity information often includes data useful in the detection of other targets of interest including blood vessel walls. The proximity of the vessel wall to a sensor or device being guided in the vasculature must be known. One of the techniques used in the inventive system is to use two sensors for data acquisition from the blood flow. In one embodiment of the present invention, sensors are mounted on a guided vascular access device to optimize the data to be acquired by that sensor. In the case where velocity data is optimized, one or more forward looking or angled sensors are driven in Doppler mode to provide velocity information. In the case where wall position/distance data is optimized, one or more laterally looking or angled sensors are driven in A-scan mode to provide information about the proximity of the vessel wall. In another preferred embodiment, one sensor is driven in a sequence of modes: a) in Doppler mode to provide velocity and direction information and b) in A-scan mode to provide information about wall proximity, i.e., if the sensor is close to the vessel wall. In one embodiment, the sensor in a tip mounted sensor (e.g., FIGS. 13A, 13B, 7, 8A, 23A and 24). In another embodiment, the sensor is a laterally mounted sensor (e.g., FIG. 13C, 11A, or 11B).

In addition to the pulsed wave mode described above (PW), the Doppler shift estimator and the velocity and direction estimators can be programmed to work in continuous wave Doppler mode (CW). As is conventional in CW mode processing, two sensors are utilized. One sensor is continuously driven to transmit ultrasound energy and the other one is continuously receiving the ultrasound echoes. The guided vascular access device embodiments illustrated in FIGS. 15, 9A, 13A, 13B, 24, 23A may be configured to operate in CW mode my designating sensor/sensor(s) to transmit and other sensor/sensor(s) to receive. It is to be appreciated that other single sensor embodiments illustrated herein may be modified to include additional dedicated transmit or receive sensors. Moreover, it is to be appreciated that in guided vascular access device embodiments where a single sensor is shown, it may be replaced by two sensors for CW mode operation.

Returning to FIG. 27, the A-scan or A-mode block 2740 receives and processes echoes amplitudes from the target of interest in a conventional manner. By analyzing the A-scan patterns, a target structure estimator (block 2745) provides information about the vessel wall, e.g., vessel wall proximity to a sensor. Such a case can be seen in FIG. 35 when the sensor 110 is in position 2 and the A-scan signal in the illustrative waveform increases. This A-scan processing is especially needed because the Doppler preprocessing (i.e., the clutter filter described in FIG. 30) removes strong echoes from slow moving targets like the vessel wall. Ultrasound processing techniques of the present invention advantageously use A-scan in sync and combination with Doppler to optimize the data acquisition and processing of the multi-single beam ultrasound system herein for the low blood flow velocities encountered in the venous system. As such, Doppler processing is optimized for low velocities through the clutter filter and the A-scan is optimized to detect the presence of slow moving, strong echo vessel wall.

Figure 49:
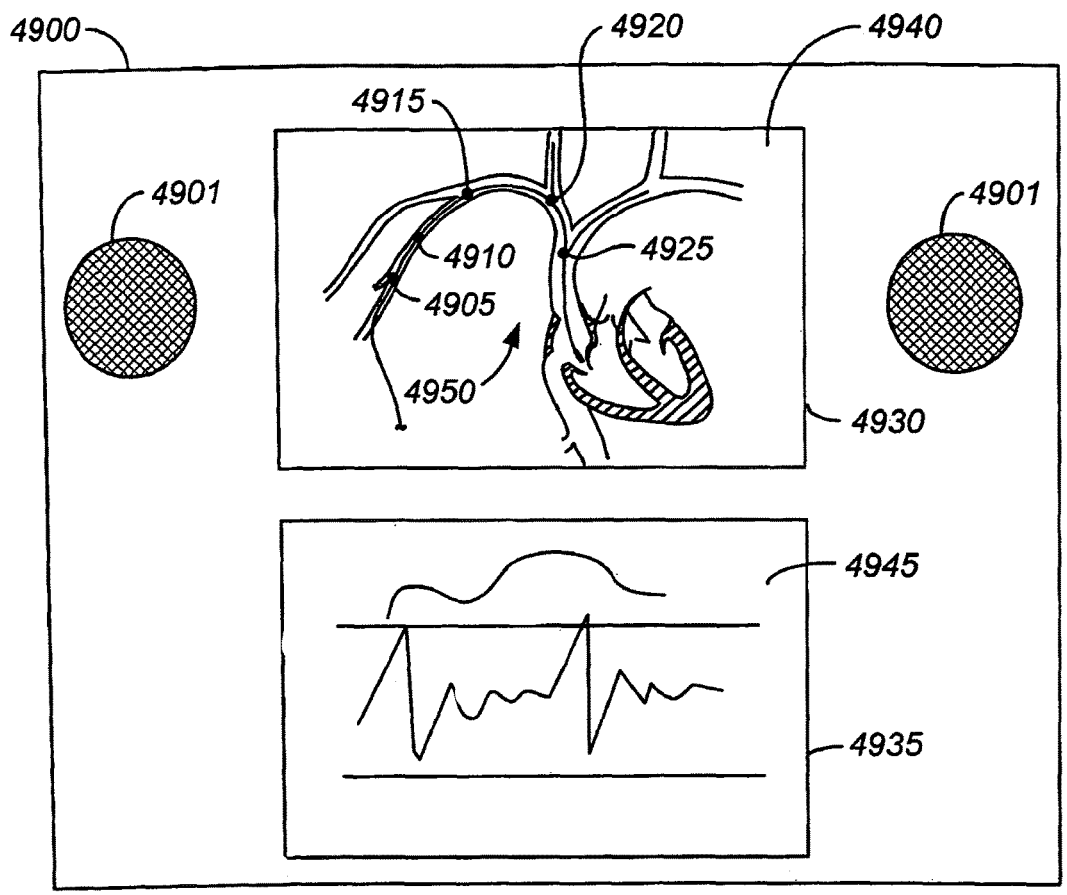
FIG. 49 illustrates a pathway specific user interface with LED indicators.

As illustrated in FIG. 27, the pattern analysis block 2650 processes the inputs from the velocity and direction estimator 2730, the correlator and target tracking estimator 2735, the pressure estimator 2750, and the target structure estimator 2745. The result of the pattern analysis operations is used to provide information about the location of a guided vascular access device (block 2770). The result of processing by the location estimator 2770 is used to control the device status indicator lights (green, red, blue, and yellow etc.) as needed for a specific user interface (e.g., FIGS. 4, 34-40, 49, 50A and 50B) or audio output (i.e., speakers 4901 in FIG. 49). The pattern analysis 2650 provides real-time correlation of multiple sources for data acquisition and multi-dimensional pattern recognition. The functions performed in pattern analysis 2650 may be modified to provide the location information and the signature patterns 4945, 4935 illustrated in graphical user interface 4900 (FIG. 49). Additionally, the functions performed in pattern analysis 2650 may be modified to remove signal artifacts such that target signal signatures can be reliably determined. Examples of signal artifacts that may be removed by the functions performed in pattern analysis 2650 include, by way of example and not limitation, respiratory motion artifact and the velocity artifacts produced by manually advancing a guided vascular access device in the blood stream.

The flow pattern estimator 2765 uses velocity and pressure estimations to determine blood flow patterns in real time: velocity profile, direction, power spectrum. It maintains a history buffer for theses values for at least 100 heart beats. It computes statistical averages of flow parameters over the history buffer and computes the Fourier Transform to provide power spectrum for velocity data. In one embodiment the Fourier Transform is computed a Fast Fourier Transform (FFT) algorithm. Results of flow pattern estimations are FIGS. 34-48. For example FIG. 34 graph "1" shows the blood flow velocity distribution as a function of time in the basilic vein calculated using Doppler signals or the target tracking method. The graph "1'" of FIG. 34 shows the same information for brachial artery. In another example in FIG. 36 the spectral power of velocities away from transducer (sensor) and towards the transducer (sensor) are illustrated. It is important to note though that FIGS. 34-48 show simplified graphs of velocity and power for purposes of illustration and not meant to represent actual processed data.

Figure 35:
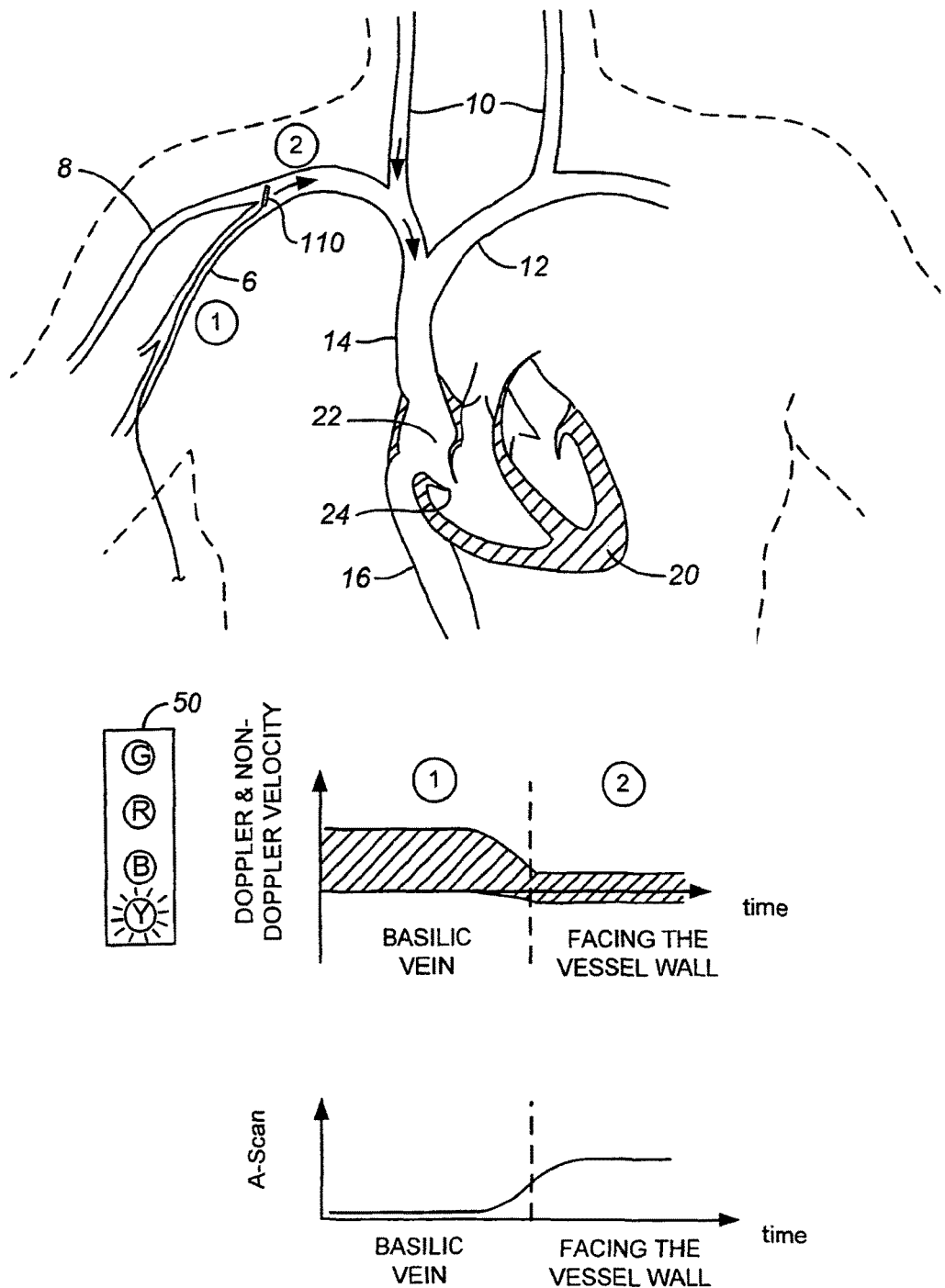

The target signature estimator 2775 combines flow patterns and target structure information to determine a multi-dimensional signature of an anatomical target. For example FIG. 35 shows a situation in which the elongate member with sensor faces the vessel wall. The velocity curve shows an unexpected drop from a predictable flow in the basilic vein "1" to the lack of clear velocity information "2". This transition could have several causes. By looking at the A-scan pattern one can recognize a transition between blood (low reflectance) "1" to a target with high reflectance "2" which is probably a vessel wall. In addition one could use the target tracking information to verify that the target estimated as vessel well moves slowly. As a further example of multi-dimensional target signature estimation, Grunwald describes methods to recognize physiological structures based on the statistical signatures using ultrasound in U.S. Pat. No. 6,120,445 to Grunwald for Method and apparatus for adaptive cross-sectional area computation of IVUS objects using their statistical signatures.

Figure 38:
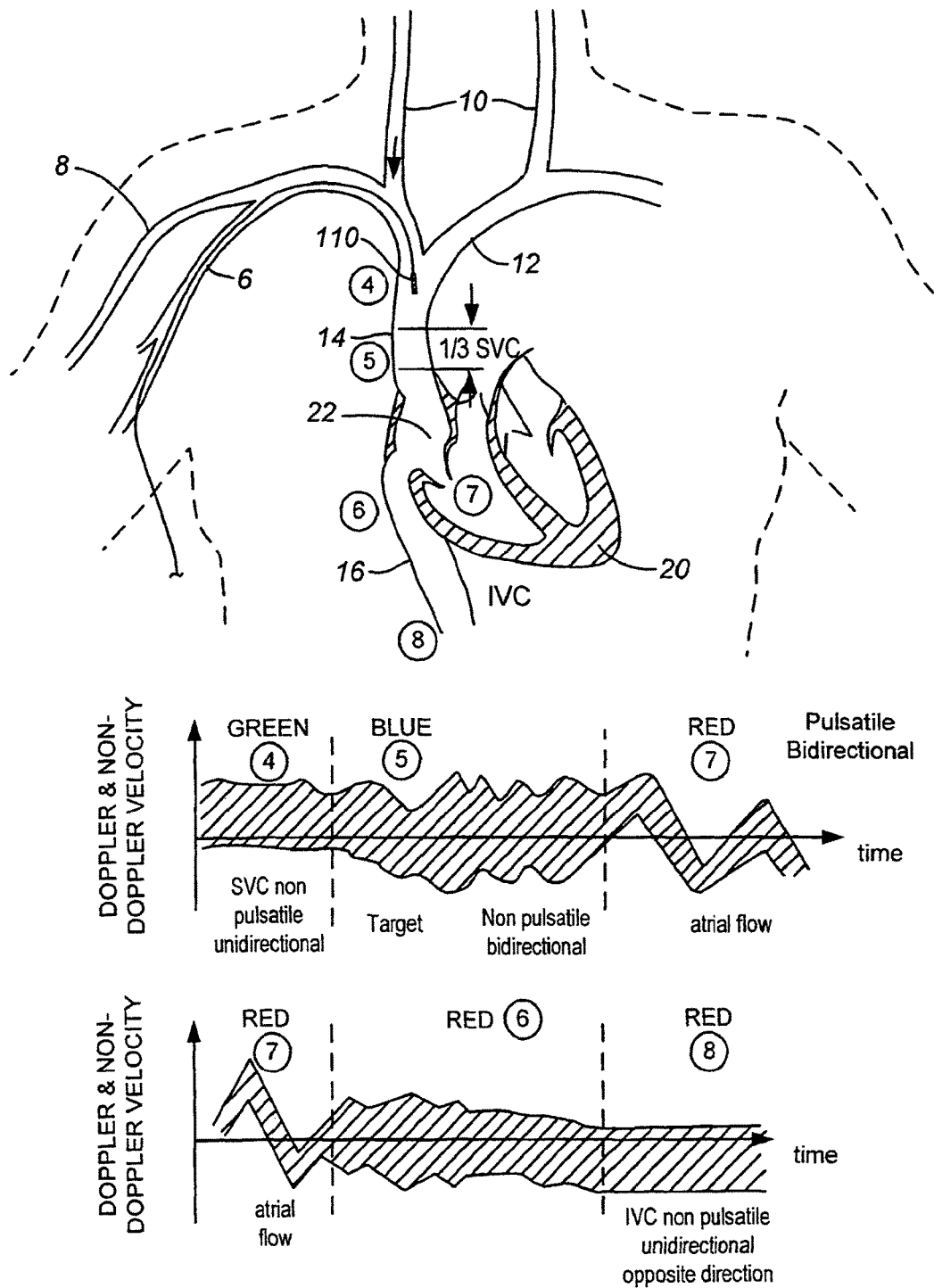

The location estimator 2770 compares the estimated target signature with a database of signatures or guidelines in order to estimate the location within the vessel. For example, the location estimator 2770 is used to determine if, when a guided vascular access device moves, the device moves in the same direction or in the opposite direction as the main blood stream flow in the vessel. Thereafter, the user is notified about the result of the location estimation. It is important to note that the user also has direct access to the flow patterns and A-scan information either on a dedicated display (i.e., FIG. 49) or by switching a monitor to display the flow patterns and A-scan information. As such, the user must make the final determination regarding the guidance actions to be taken based on the system provided information. In another example, the estimator 2770 detects target signature corresponding to the lower third of the vena cava (i.e., FIGS. 38 and 53). By providing this information to the user, the system helps positioning the sensor and the catheter at the desired location. FIG. 38 shows the flow patterns that can be used in one embodiment to estimate that the device has reached the lower third of the SVC and to turn the blue light on.

The Signature Database 2755 is used to compare the determined target signature estimator with signatures in a database in order to identify the target. In another embodiment the database stores anatomical decision criteria, thresholds, and statistical decision making to provide identification of the target. The database and the decision making can be used independently. When used in combination, the information provided is correlated for safer target identification.

The calibration block 2760 serves to dynamically adapt the system settings relative to each patient. This component is needed to provide information about the flow patterns relative to the patient under examination. In this context, calibration means the determination of blood flow velocities and patterns at the access point or immediately behind it, i.e., at a known point in the vasculature. Such patterns include but are not limited to: average velocity, spectrum of velocities, velocity profile during a heart cycle, direct and reverse flow velocities and ratio, etc. In addition to determining velocity parameters at the access point, the calibration algorithm can compare and adjust these parameters against a database of values and patterns. Information about the relationship between the patterns at the point of access and the patterns at the end point may be retrieved from the database.

The Auto-optimization block 2780 serves for automatic adjustment of system settings in order to optimize system operation. In one embodiment the following parameters are automatically optimized: 1) Dynamic range for A-scan; 2) Clutter filter cut-off frequencies; 3) Sample volume size for optimizing velocity information. Additional suitable auto-optimization methods are described in U.S. Pat. No. 6,733,454 to Bakircioglu et al. for Automatic optimization methods and systems for doppler ultrasound imaging and U.S. Pat. No. 6,542,626 to Brouwer et al. for Method and apparatus for adapting imaging system operation based on pixel intensity histogram.

FIGS. 34-48 provide numerous specific examples of how the multi-single beam ultrasound system and techniques for its use that are described herein may be used as an endovascular access and guidance system. As will be appreciated by those skilled in the art, waveforms are simplified merely exemplary of time-compressed composite waveforms for purposes of illustration. The endovascular access and guidance system includes an elongate flexible member adapted and configured to access the vasculature of a patient such as those described previously with regard to FIGS. 7-24.

In the FIGS. that follow, the methods described to access, navigate and locate structures within the vasculature will be described with reference to a guided endovascular access device 110. The guided endovascular access device 110 may be adapted to deliver a therapy to the patient and/or to provide endovenous access for another device. The device 110 may be a catheter, a guide wire or a stylet.

The guided endovascular access device 110 includes one or more sensors that may have an associated divergent lens disposed at a distal end thereof. The one or more sensors are configured to provide in vivo non-image based ultrasound information of the venous vasculature of the patient into which the guided endovascular access device 110 has been inserted. A divergent lens may be associated with the sensor or a plurality of lenses may be associated with the sensor. Additionally, there may also be provided a sensor attachment mechanism adapted to removably detach the sensor from the guided endovascular access device 110 while the guided endovascular access device 110 remains in the vasculature of the patient.

There is also a processor configured to receive and process in vivo non-image based ultrasound information of the venous vasculature of the patient provided by the sensor and to provide position information regarding the position of the distal end and/or sensor location on the guided endovascular access device 110 within the vasculature of the patient, the processor is further configured to process in vivo non-image based ultrasound information of the vasculature system of the patient to indicate in the output information movement of the endovascular access device 110 in a desired direction within the vasculature of the patient. Additionally, the processor is further configured to process in vivo non-image based ultrasound information of the vasculature system of the patient based on a parameter selected from a group consisting of: a venous blood flow direction, a venous blood flow velocity, a venous blood flow signature pattern, a pressure signature pattern, A-scan information and a preferential non-random direction of flow. In each figure, a device progress or position indicator 50 acts as an output device adapted to output the position information and other indicators from the processor. The device progress or position indicator 50 is illustrated with the appropriate light configuration or the color of appropriate light configuration is indicated in the figures.

More specifically, FIGS. 34-48 detail methods for positioning an instrument in the venous system of a body by accessing the venous system of the body to position an instrument in the venous system of the body. Next, the instrument transmits an ultrasound signal into the venous system of the body. In some embodiments, the instrument transmits an A mode ultrasound signal into the venous system of the body. In other embodiments, the instrument transmits a non-imaging cross-correlation ultrasound signal into the venous system of the body. Thereafter, the sensor or another sensor is used to receive a reflected ultrasound signal from the vasculature. In some embodiments, the reflected ultrasound signal from the vasculature indicates flow rates between 2 and 20 cm/s. The reflected ultrasound signal is processed to determine a flow pattern within the vasculature. The determined flow pattern may be in a direction towards or a direction away from the instrument. Next, the determined flow pattern within the vasculature can be used for advancing the instrument within the vasculature. Additionally or alternatively, the determined flow pattern within the vasculature can be evaluated for the presence of a signal indicating a specific blood flow pattern.

FIGS. 34 to 39 will be used to describe how the systems and techniques for vascular access may be applied to gain access to the central venous system. In this example, the intention is to enter the venous system in the basilic vein and advance the device 110 to a position at ⅓ of the superior vena cava as indicated in FIG. 38. This portion the venous system of a person includes the cephalic vein 8, the basilic vein 6, jugular veins 10, the brachiocephalic (innominate) 12, the superior vena cava 14 and inferior vena cava 16. Two features of the heart 20 are also illustrated in this view: the tricuspid valve 24 and the right atrium 22.

When the guided endovascular access device 110 in first introduced into the vasculature it may not be apparent whether the device has accessed a vein or an artery. The waveform associated with 1' indicates a pulsatile flow that includes flow both away from and toward the sensor on device 110. The device status indicator 50 illuminates a red light to indicate that the sensor is detecting a flow pattern of signature that is not in the desired direction. The system indicates a red light because the specified access method for this example intends to guide a device access along an antegrade venous flow path to provide central venous access. The waveform generated in 1' clearly indicates that the sensor is not correctly positioned within the venous system.

Next, the device 110 is withdrawn from the brachial artery and is successfully inserted into the basilic vein 6. The waveform associated with 1 indicates a non-pulsatile, low velocity flow away from the sensor. The device status indicator 50 illuminates a green light to indicate that the sensor is detecting a flow pattern an/or signature that is in the desired direction. The system indicated that the sensor is in the desired position because the sensor is detecting flow patterns that indicate a position within the venous system with flow going away from the sensor which also indicates the sensor is correctly placed for the desired antegrade movement towards the SVC.

After the device 110 has been properly inserted into the venous system of a person, the data acquisition, signal processing techniques and systems described above in FIGS. 26, 27, 29 and 30 will gather patient specific data for processing and recording as part of a patient specific database as well as for use in the signature database. Acquisition of patient sensor data provides real-time in vivo system calibration for patient dependent processing. Depending upon the specific circumstances of a particular patient, the system may, for example, evaluate entry blood pressure, velocity, peak velocity and other factors. Additionally, the patient sensor data will be processed via the processor to store data related to the processing of in vivo non-image based ultrasound information of the vasculature system of the patient based on a parameter selected from a group consisting of: a venous blood flow direction, a venous blood flow velocity, a venous blood flow signature pattern, a pressure signature pattern, A-scan information and a preferential non-random direction of flow. As discussed above with regard to FIGS. 26, 27, 29 and 30, these patient specific factors relate all system parameters and subsequent data to all values and data to this patient.

Turning now to FIG. 35, the user will advance the device 110 through the vasculature, the basilic vein in this example, while monitoring the device status indicator 50. As long as the device status indicator 50 shows a "green light" the device 110 is being advancing in the desired direction. This means that the signals received and processed by the system detect flow patterns and signatures received that indicate proper device movement/position. A green light indication will remain on while the device advances from 1 to just before contacting the vessel wall at 2.

FIG. 35 also illustrates the A-scan and Doppler and Non-Doppler velocity waveforms for positions 1 and 2. The waveforms for position 1 indicate movement within the vessel in the desired direction: a constant velocity flow away from the sensor and a low A-scan waveform. In contrast, The waveforms for position 2 indicate device position against the wall (i.e., high A-scan waveform) and low velocity flow away from the sensor and indications of flow towards the sensor (i.e., the slightly negative waveform). As such FIG. 35 indicates the sensor 110 in a condition that will generate a yellow system output in device status indicator 50. A yellow system output occurs when the data acquired from the sensor contains no recognizable pattern or that the data acquired from the sensor does not provide any meaningful information upon which any useful device position information may be derived.

Figure 36:
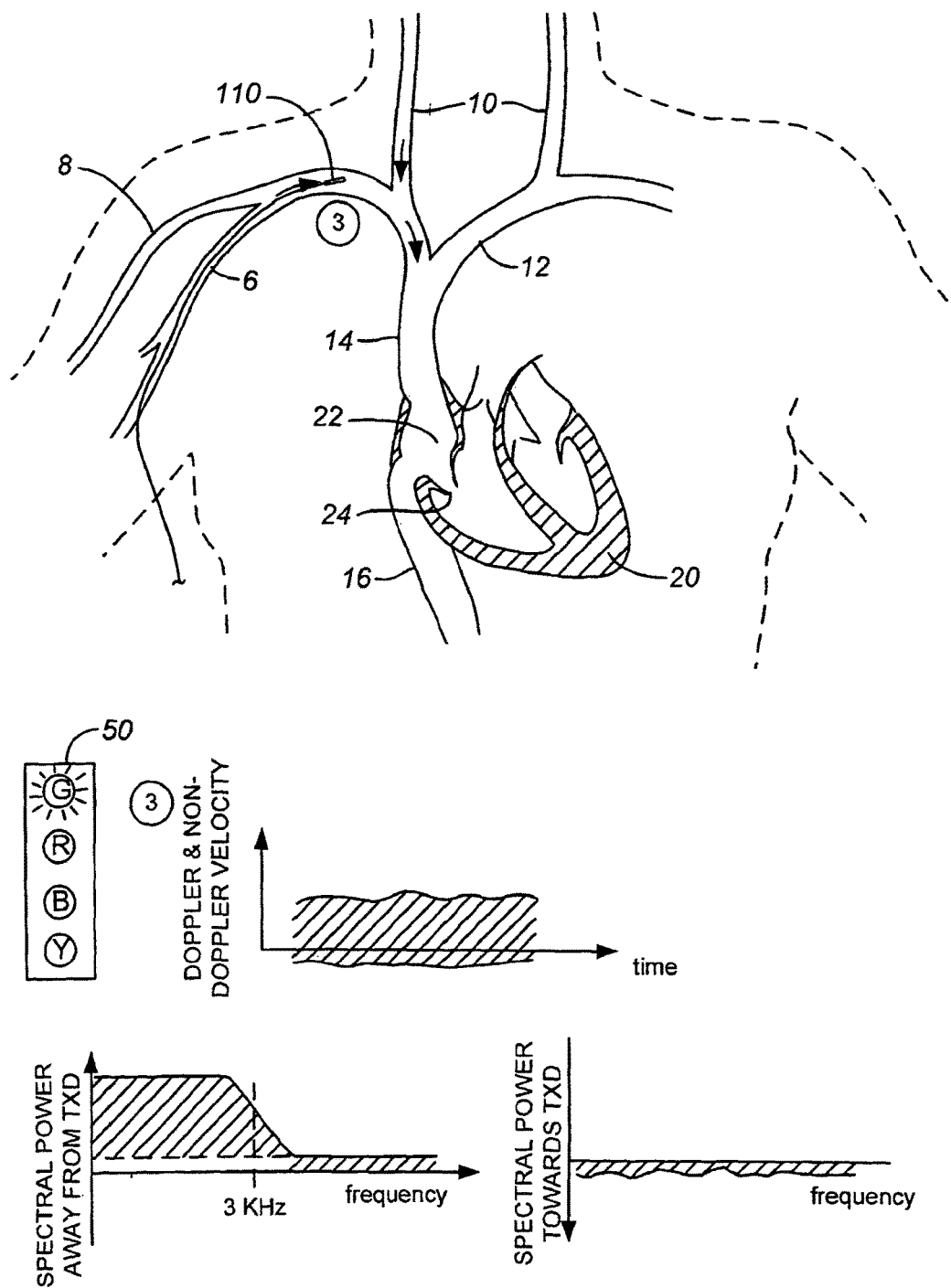

As illustrated in FIG. 36, the user has maneuvered the device 110 to clear the yellow indication by moving the device to the indicated position 3. The action taken by the user restores proper device movement within the vasculature. The green device status indicator 50 and waveforms in FIG. 36 all indicate that the device 110 is advancing the desired direction at position 3.

FIG. 37 and the associated waveforms indicate the result of advancing the device into the jugular 10. Since the flow of blood in the internal jugular is towards the heart the current placement of the device produces waveforms from the sensors that clearly indicate the device is not in the desired location within the vasculature. Appropriately, the device status indicator 50 indicates a red light. As illustrated, when the device is within the jugular, the device 110 is now placed into a flow towards the heart (here, towards the sensor as well). As such, the waveforms indicate a larger power return directed towards the sensor as well as higher velocities toward the sensor than away from the sensor.

FIG. 38 and the associated waveforms correspond to the numbered position locators indicated in the illustration of the vasculature of the patient. The color of the device status indicator 50 is indicated along the waveform corresponding to the signals received when the device 110 is placed at that position locator. The waveforms and indication from the device status indicator 50 illustrate how the system may differentiate the various different flow situations encountered within the vasculature.

A position indicator 4 the device 110 is advancing through the superior vena cava 14 in the desired direction such that the device status indicator 50 indicates green. The illustrative waveform shows the recognizable non-pulsatile, unidirectional flow indicative of the venous system.

As the device 110 transitions along the SVC, the sensors begin to detect the presence of the venous flow coming towards the sensors from the inferior vena cava 16. As the device advances further, the signal from the IVC will grow and the sensors will also begin to detect the target signature or unique flow non-pulsatile bi-directional flow generated by the confluence of the venous flows within the vena cava. As a result of placing sensors in this location, processing the reflected ultrasound signal from those sensors may be used to determine the position of the sensors or an instrument coupled to the sensors relative to the caval-atrial junction. In addition, in this example, the device pathway is to have the sensors remain within antegrade flow. In this example, antegrade flow means that when the device follows a path such that the sensors predominately detect flow away from the sensors and towards the heart (i.e., a "green" indication for this configuration). Once the device advances past the right atrium 22 and into the inferior vena cava 16, the predominate flow is now towards the sensor causing the system to produce a device status indicator 50 that indicates red (i.e., positions 6 and 8).

It is to be appreciated that the method of detecting a sequence of flows may also be used to determine the position of the device within the vasculature. For example, a pattern indicating a strong non-pulsatile unidirectional green flow pattern (i.e., position 4), then non-pulsatile, bi-directional blue flow pattern (i.e., position 5) and then, with forward—not rearward device movement, a strong non-pulsatile unidirectional red flow pattern (i.e., position 8) could be used to indicate the proper pathway for a user desiring superior access the inferior vena cava 16. The pulsatile bidirectional flow of the atrium and the right ventricle may also be detected by the system. The unique pulsatile, bidirectional flow pattern present when the sensors are placed in position 7 may also be detected by the system and used to provide access to the vasculature.

FIG. 39 illustrates the unique waveforms generated based on sensor inputs when the device is placed in the indication positions. When the device is placed at position 5 in the target region of the lower ⅓ of the superior vena cava 14, the status indicator 50 is blue and the waveforms indicate non-pulsatile bidirectional power. In contrast, when the device 110 is placed within the right ventricle, the waveforms generated from sensor data indicate a clear and strong pulsatile, bidirectional flow pattern.

FIG. 40 illustrates the waveforms and direction indicator for a sensor intended to advance to the superior vena cava 14 that instead reaches the inferior vena cava 16. Note that the waveforms show that when the sensor is in position 8 the power away from the sensor is low while the power towards the sensor is much higher. These waveforms clearly indicate the system has detected the opposite flow direction from the desired flow direction. As a result, the status indicator is red when the device is in position 8.

Figure 43A:
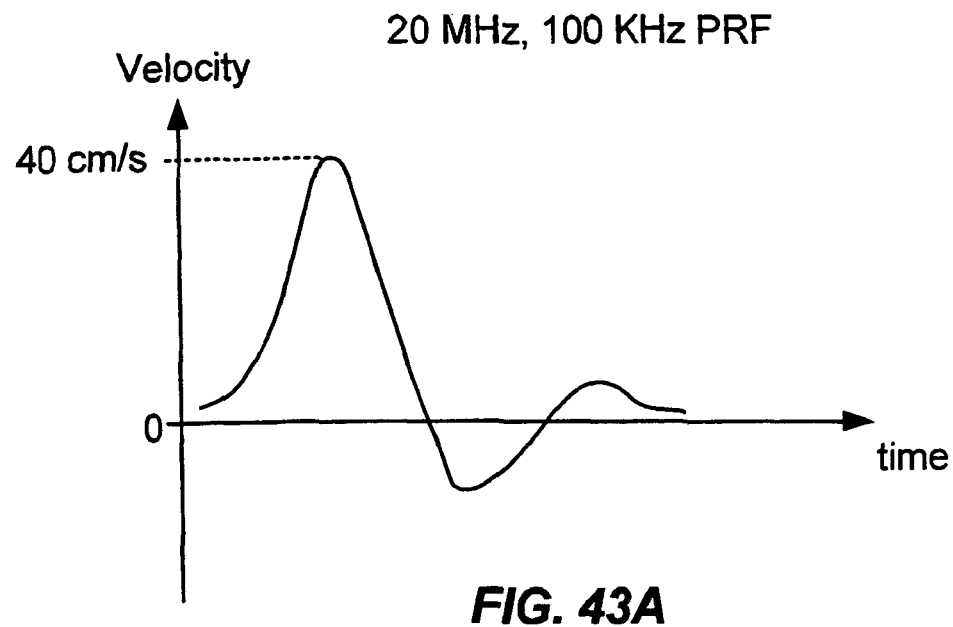
FIGS. 43A-B illustrate a parameter of the multi-single beam ultrasound system of the present invention.
Figure 43B:
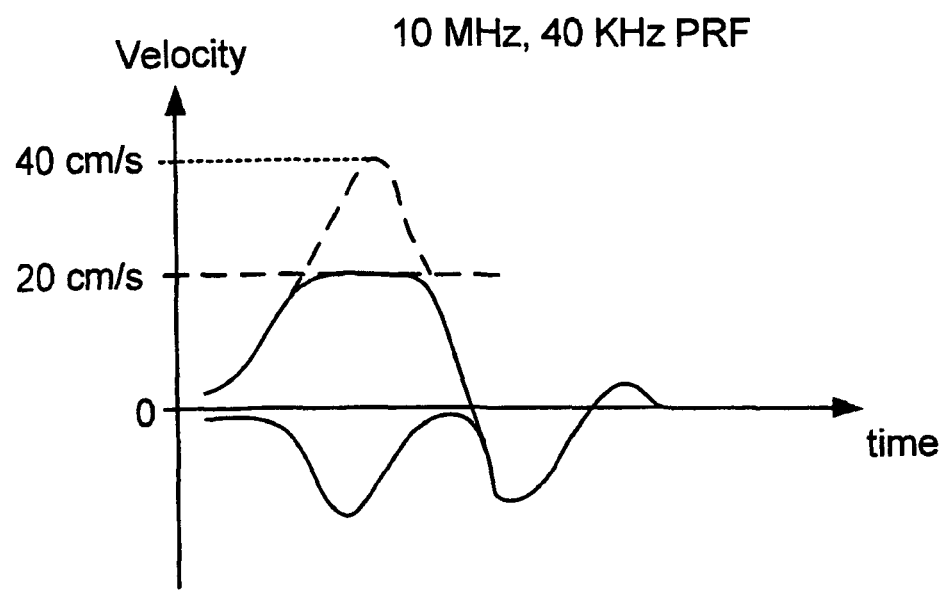

FIGS. 43A and B will be used to describe a parameter unique to the multi-single beam ultrasound systems of the present invention. FIG. 43A illustrates the typical velocity waveform for an ultrasound system having an operating frequency of 20 MHz and a 100 kHz pulse repetition frequency. An arterial peak velocity of 40 cm/sec is indicated using a pulsatile flow pattern. FIG. 43B illustrates that same high velocity signal when received by our system that operates with an operating frequency that is half that of arterial ultrasound systems (i.e., 10 MHz) and a pulse repetition frequency that is only 40% of the pulse repetition frequency (i.e., only 40 kHz). Recall that in a multi-single beam ultrasound system configured to operate in the low speed, large sample volume environment of the venous system where the flow velocity ranges from 2 to 15 cm/sec., a flow velocity of 40 cm/sec cannot be fully characterized by the system as in FIG. 43A. As such, the slower system characteristics of our system cut off the high end of the velocity curve, as indicated at A, i.e., at approximately 20 cm/sec. When that cut-off velocity is finally registered by our system, it manifests as a negative (i.e., below 0 velocity reading). Or with other words as a flow of 20 cm/sec in the opposite direction. This phenomenon is referred to as aliasing of arterial flow. By inducing the aliasing of high velocities, our system converts the high velocities into low velocities of opposite direction, i.e., translates the velocity information in flow direction information. This ability of the system is used to identify arterial or heart chamber flow although all parameters are optimized to detect venous flow. Thus the system can reliably identify transitions between venous and arterial or heart flows by using the velocity information characterizing the main blood stream.

Figure 44:
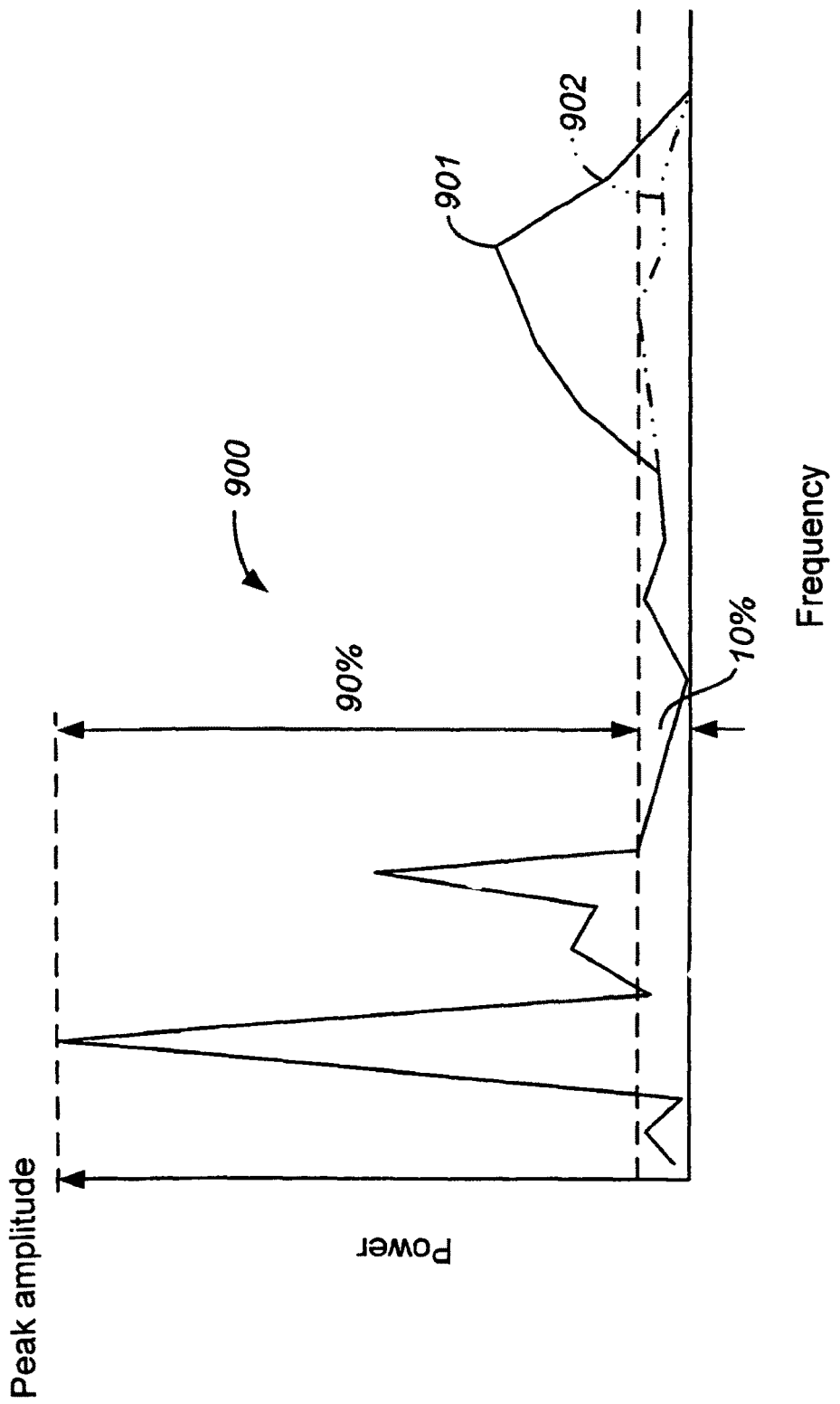
FIG. 44 illustrates a power vs. frequency curve.

FIG. 44 illustrates a power v. frequency curve 900. The curve 900 indicates the power curve for pulsatile flow measured within arteries or the heart. According to this invention the range of power spectrum values is divided in two regions. The lower 10-20% of the power represents non-preferential velocities in the blood stream. In contrast the upper 80-90% of the power represent preferential velocities, i.e., non-random movements in the blood stream. In order to provide for a more reliable characterization of blood flow, in this invention only preferential non-random velocities are analyzed. A threshold is defined for the power spectrum situated at 10-20% of the peak amplitude. Velocities with a spectral power below the threshold are not considered for the analysis. Only velocities with a spectral power above the threshold contribute to signature patterns. For example velocities illustrated by curve 902 representing random turbulence in a typical arterial flow are excluded from analysis as being non-preferential and therefore irrelevant.

As a result of aliasing of arterial flow alone or in combination with the removal of random, turbulent flow, the multi-single beam ultrasound systems of the present invention may be used to detect changes in structures and flow patterns within the heart and in the surrounding vessels. Compared to prior art methods that use turbulence indicators of random flow, as in U.S. Pat. No. 6,704,590 to Haldeman for Doppler guiding catheter using sensed blood turbulence levels the method presented in this invention provides a more reliable and more accurate, low velocity, low frequency identification method of transitions between flow in arteries or heart chambers and blood flow in veins. The waveform illustrated in FIG. 45 illustrates how the system may detect the transition from venous flow into an aliasing of atrial flow as the device 110 moves from the superior vena cava (i.e., venous flow) into the right atrium 22 where aliasing begins. In addition, the waveforms in FIG. 46 illustrate representative signals detected by the system as the device 110 is positioned in the right atrium. Because the system of the invention may be optimized to detect slow moving objects that are typically filtered out of arterial and imaging ultrasound systems, the operation of the tricuspid valve is readily detected by the system as indicated by the waveforms. As shown, our system converts detected high velocities into a detection of flow direction by using induced signal aliasing. Similarly, this allows our system to convert high velocity signals into directional information.

Figure 47:
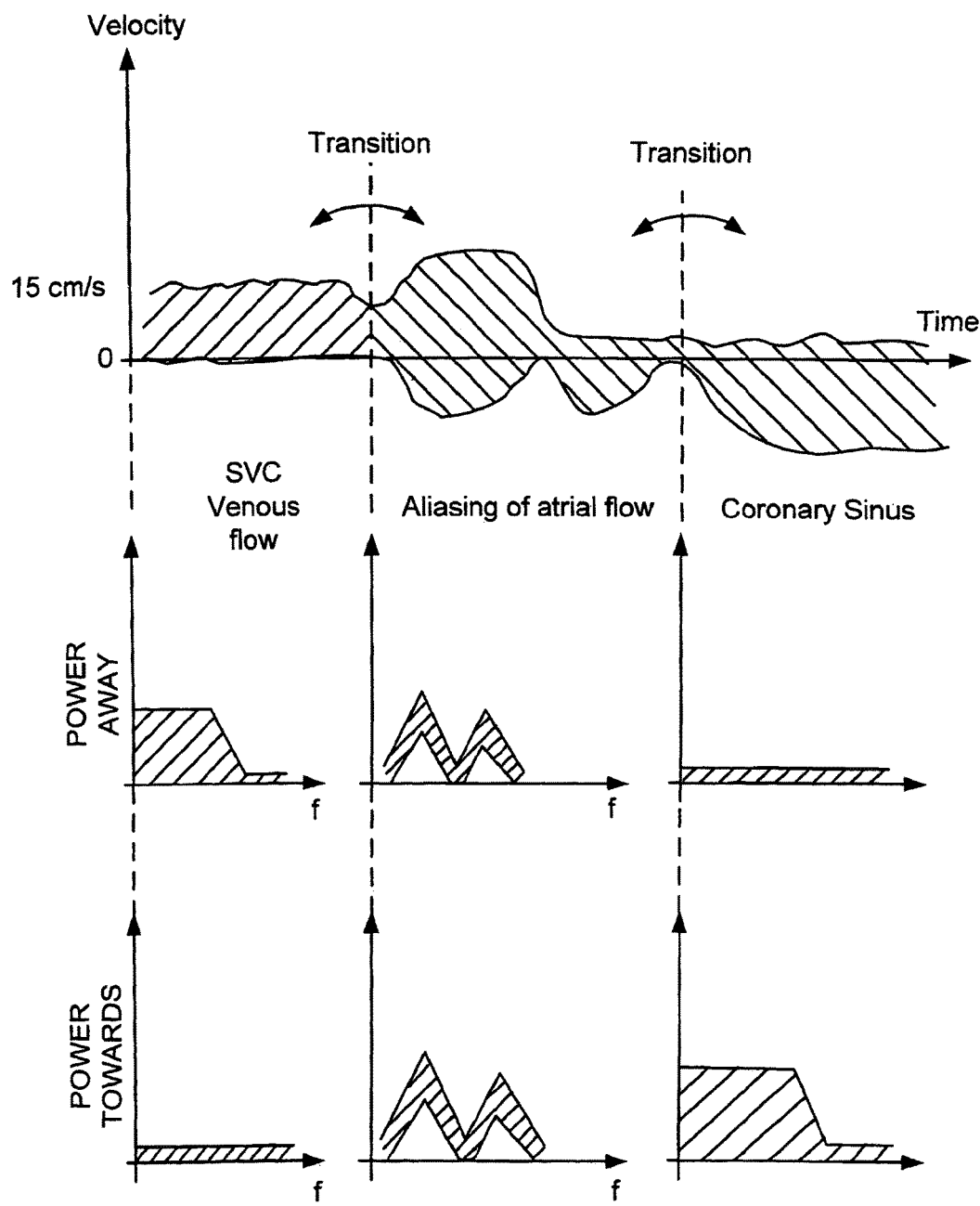
FIG. 47 illustrates a signature pattern sequence that may be used to reliably and accurately identify a path from the superior vena cava to the coronary sinus.

FIG. 47 illustrates a signature pattern sequence that may be used to reliably and accurately identify a path from the superior vena cava to the coronary sinus. Similar to the sequence described about where the system detects the transition from one distinct flow regime (unidirectional venous flow) into another (bidirectional caval-atrial junction flow), embodiments of the present invention may be used to detect the transition back to venous flow after passing through an indication of atrial flow, e.g., through a heart chamber. The ability of the system to detect these pattern changes will enable devices and sensors of the present invention to identify, locate and access venous flows entering the left atrium. In the example of FIG. 47, the pattern transitions from venous to aliased flows and back to venous may be used to detect the venous flow from the coronary sinus. In similar fashion, this technique may be used to identify one or more of the pulmonary veins or other venous flow into the left atrium. As discussed above, the sensors and guides access devices described above with regard to FIGS. 7-24 may be configured to mimic the expected anatomical and flow patterns or signatures to be generated by a sensor in the right atrium and positioned accordingly.

Treatment of Venous Disease

In the case of varicose vein treatment, a therapy catheter (i.e., a catheter adapted to delivery laser, the RF, or any other type of energy for the treatment of the veins) is positioned precisely at the sapheno-femoral junction (SFJ). The position of the catheter within the vein can be determined according to the present invention by using the Doppler effect and the difference in blood flow patterns between the great saphaneous vein (GSV) and the common femoral vein (CFV). For example, in the common femoral vein, the blood flow changes more dramatically with respiration than in the great saphaneous vein.

Figure 48:
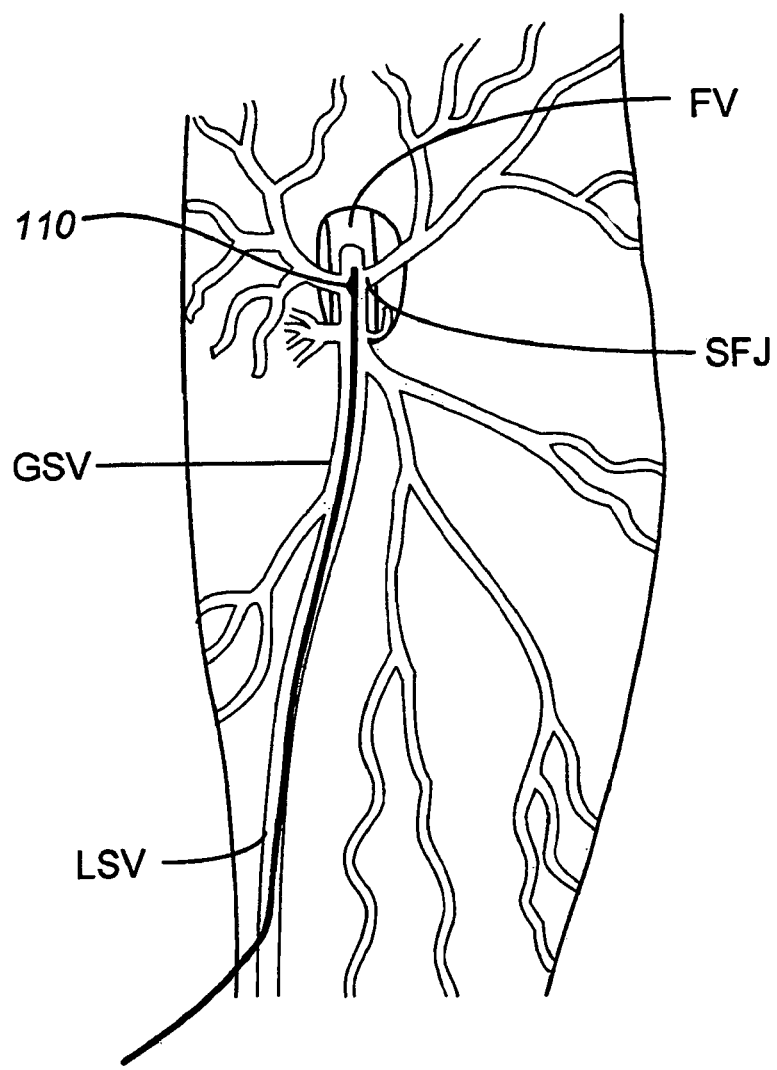
FIG. 48 illustrates a guided vascular access device of the invention in the sapheno-femoral junction.

FIG. 48 illustrates a guided vascular access device positioned at the sapheno-femoral junction (SFJ). Also illustrated are some of the other anatomical landmarks that may be used for intravascular positioning of a venous catheter at the SFJ where many of the superficial veins come together before joining the common femoral vein (CFV). The flow of blood at this junction is controlled by a one-way valve which is designed to direct blood inwards and upwards, helping it to return towards the heart. If this valve fails to function properly, some blood is able to flow back down into the leg, increasing the pressure in the superficial veins and their branches. The great saphenous vein (GSV) is one of the main superficial veins in the thigh. If extra blood is forced into it by a leaking valve at the SFJ, the vein stretches and further valves within it become distorted and begin to leak. Blood is then able to flow further down the leg in the wrong direction, eventually filling and distending more and more branches, causing the appearance of varicose veins in the thigh and calf.

In the case of varicose vein treatment, a therapeutic catheter (i.e., a catheter adapted to delivery laser, the RF, or any other type of energy for the treatment of the veins) must be positioned precisely at the SFJ. The position of the catheter within the vein can be determined according to the present invention.

In the case of detecting the SFJ, the position detection algorithm identifies the differences between the flow patterns in the GSV and in the common femoral vein. The blood flow in the GSV is usually antegrade towards the heart in patients with GSV reflux when they are lying supine, which would be the case during a venous ablation procedure. It is when the calf is squeezed and then released that the blood flow will reverse for a brief instant—usually 1 to 4 seconds—as the blood rushes distally in the GSV to fill the empty veins below. This maneuver can be done during catheter placement with the patient in the reverse Trendelenberg position to help define the position of the SFJ.

In the CFV the flow pattern also changes more dramatically with respiration. CFV algorithm has a component that is able to detect the changes in the Doppler signal due to the blood vessel motion resulting from respiration. In addition, if the valve fails to function properly, some blood is able to flow back down into the leg, increasing the pressure in the superficial veins and their branches. The blood flow in a diseased patient shows more components of reverse flow in the GSV when compared to the CFV. In the Duplex scan of the SFJ the red color demonstrates forward flow in the CFV, and the blue color represents reversed flow in the incompetent long saphaneous vein. (Caution here is important as mild reflux is often normally seen in the distal external iliac and common femoral veins.) The intervention catheter is positioned in the GSV before the SFJ. The tip of the catheter is located in the main blood stream of the CFV. The present invention discriminates between the two positions by using Doppler signal analysis and discrimination of flow patterns.

Once an appropriate sensor is placed in a position to properly detect venous flow in the diseased vein, then the procedure detailed above may be performed while the system monitors flow performance characteristics of the vein and the diseased vein. When the blood flows away from the transducer in more turbulent patterns. In the femoral vein the blood flows towards the catheter in a more stable flow pattern and with additional components due to respiratory movements. As such, embodiments of the system of the invention may be used to detect differences in flow patterns or flow signatures or other properties between a healthy vein and a diseased vein. As mentioned previously, the method also applies to the junction of the lesser saphenous vein and popliteal vein behind the knee and may also apply to identifying the junction of a perforator vein in the calf and a superficial vein or a perforator vein and a deep tibial vein.

The detection of the transition region flow patterns are based on recognizing characteristic flow signatures of the regions, e.g., average velocity, velocity spectrum, and ratios between direct and reverse flow, as well as the changes thereof in time. The inventive concept described herein of using physiological signatures or identifiers to detect specific locations in the vasculature from within the blood vessel can be also applied to other functional measurements other than Doppler velocity, e.g. to pressure and temperature profiles. In these cases, appropriate pressure and temperature sensors would be used. As described herein, the processing techniques and operation of the multi-single beam ultrasound system may be used to identify and discriminate the relative variation of pressure profiles at various locations in the vasculature. However, it has not been attempted though thus far to use these variations in order to identify the location in the vasculature as envisioned by embodiments of the present invention.

In additional alternative embodiments, there is provided a method for positioning an instrument in the vasculature of a body by processing a reflected ultrasound signal to determine the presence of a signal indicating a position where two or more vessels join. This method may be practiced in any of a wide variety of vascular junctions in both the venous and arterial vasculature. One exemplary position where two or more vessels join occurs where the two or more vessels include a superior vena cava and an inferior vena cava. A second exemplary position where two or more vessels join occurs where the two or more vessels include an inferior vena cava and a renal vein. A third exemplary position where two or more vessels join occurs where the two or more vessels include a right common iliac vein and a left common iliac vein. A fourth exemplary position where two or more vessels join occurs where the two or more vessels include an external iliac vein and an internal iliac vein. A fifth exemplary position where two or more vessels join occurs where the two or more vessels include a right brachiocephalic vein and a left brachiocephalic vein. A sixth exemplary position where two or more vessels join occurs where the two or more vessels include a superior vena cava and an azygous vein. A seventh exemplary position where two or more vessels join occurs where the two or more vessels include a common femoral vein and a great saphenous vein. An eighth exemplary position where two or more vessels join occurs where the two or more vessels include a superficial femoral vein and a deep femoral vein. An ninth exemplary position where two or more vessels join occurs where the two or more vessels include a popliteal vein and a lesser saphenous vein. An tenth exemplary position where two or more vessels join occurs where the two or more vessels include a perforator vein and a superficial vein. An eleventh exemplary position where two or more vessels join occurs where the two or more vessels include a perforator vein and a deep tibial vein. An twelfth exemplary position where two or more vessels join occurs where the two or more vessels include a great saphenous vein and a varicose vein. An thirteenth exemplary position where two or more vessels join occurs where the two or more vessels include a jugular vein and a subclavian vein. An fourteenth exemplary position where two or more vessels join occurs where the two or more vessels include a cephalic vein and an axillary vein.

In one aspect, the multi-single beam ultrasound system described herein is an endovenous access and guidance system having an elongate flexible member that is adapted and configured to access the venous vasculature of a patient. One or more sensors are disposed about the elongate flexible member in various locations such as the distal end, along the sides or in recesses formed in the sidewall and in other configurations as described herein. These sensors are configured to provide in vivo non-image based ultrasound information of the venous vasculature of the patient. In addition, a processor configured to receive and process in vivo non-image based ultrasound information of the venous vasculature of the patient provided by the one or more sensors and to provide position information regarding the position of the distal end of the elongate flexible member within the venous vasculature of the patient. Advantageously, the sensor, sensors and/or two or more additional sensors are attached to the elongate flexible member in an arrangement that mimics an endovascular junction. There is also an output device adapted to output the position information from the processor and to relate it, if desired, to the mimicked endovascular junction. The sensors may also be arranged to mimic other measurable or detectable features or parameters within the vasculature. In specific embodiments, the sensors are arranged on the elongate body to mimic one or more of the fourteen exemplary positions where two or more vessels join.

The ability of the system of the present invention to recognize and differentiate various flow patterns within the vasculature may be used in a wide variety of situations. Embodiments of the present invention may be used to locate and identify unique or signature portions of the venous system where the detectable flow pattern provides accurate information about the position of the sensor or device within the venous system. As has already been discussed, the present inventive multi-single beam ultrasound system may identify a central venous access pathway via the superior vena cava. In the illustrative examples of FIGS. 41 and 42, the system may also be used to identify other venous landmarks as well.

Embodiments of the present invention may be used to detect, locate and guide devices within the portions of the venous system illustrated in FIGS. 41 and 42. Taken together, these figures illustrate the systems ability to detect and identify at least three other unique or signature patterns within the vasculature. First, as indicated in position 1, a device 110 placed at position 1 may be used to detect the convergence of the flows from the iliac veins 26 into the single flow of the inferior vena cava 28. This flow pattern may be detected by the methods described herein to indicate this junction at position 1. Similarly, the converging bilateral flows from the renal veins 18 into the inferior vena cava 16 (position 2) may also be detected by the system. As indicated by the waveforms for position 3, the system may also detect the transition from unidirectional flow within the inferior vena cava to signature bidirectional flow associated with the right atrium and the confluence of the superior and inferior vena cavae. As such, the system is capable of identifying specific unique flow patterns and then relating the location of those flow patterns to specific anatomical landmarks such as junctions between specific veins.

It is to be appreciated that the configurations of the guided vascular access devices 110 described above in FIGS. 7-24 may have one or more sensors positioned on the device to detect an expected signature flow. For example, if the intended use of the system was to provide access and guidance to a healthcare provider attempted to place a filter within the inferior vena cava 16 in a position superior to the renal veins 18, then a device 110 having a pair of laterally directed sensors (i.e., in the 3 o'clock and 9 o'clock positions) will be able to detect the unique or signature flow patterns when the sensors are properly positioned to detect those flow patterns. As such, when the system detects those signature pattern, the user could be notified and then the device advanced as needed to reach the desired position superior to the renal veins (i.e., 1.5 cm superior to the renal veins). Of course, the position of the renal veins 18 could also be used to provide therapy or access to the renal veins 18. It is to be appreciated that this general example applies to other regions of the vasculature as well where sensor placement on the device is selected to increase the likelihood of the sensor detecting a desired signature flow, or other sought after vascular parameter. In another illustrative example, a vascular access device configured to detect the junction between the femoral veins and the iliac veins could have a combination of forward and angled rearward sensors to optimize detection of that junction. The rearward sensors mimicking the expected angle between the iliac veins 26 and the inferior vena cava 28. Rearward and forward in this example are of course relative to the desired placement of the device within the venous flow. Here, the terms reflect devices and sensors traveling as indicated in FIGS. 41 and 42.

The description above relates to the use of sensors to mimic junctions or other system detectable parameters of the venous vasculature. It is to be appreciated that the invention is not so limited and that the concept of sensor placement to mimic the vasculature may also be applied to the arterial vasculature as well.

FIG. 49 illustrates a procedure specific user interface 4900. The procedure specific user interface 4900 is a hand held electronic interface, PDA or other suitable display may graphically represent progress of a guided vascular access device along a desired path. The procedure specific user interface 4900 includes displays 4930, 4935. Optionally, the procedure specific user interface 4900 includes speakers 4901 and 4902. Display 4930 is configured to illustrate the progress of a guided vascular access device from an insertion point to a targeted delivery point. A plurality of path progress indicators 4905-4925 are arrayed along the desired path. As shown in display 4930, a display may also include an image 4940 that is specifically designed to show the expected vessel travel path to be encountered by a particular device during a specific use. As shown in display 4935, a display may also be designed to show real time system output based on data acquired from sensors as shown in the waveforms in image 4945. Display 4930 and the associated plurality of path progress indicators 4905-4925 may be configured to illustrate the progress of a guided vascular access device from an insertion point to a targeted delivery point. In one embodiment, the targeted delivery point includes those specific portions of the vasculature or venous system described above. Alternatively or in addition, one or more of the associated plurality of path progress indicators 4905-4925 may be utilized to also include the data received and analyzed from a sensor or sensors intended to mimic a portion of the vasculature as described herein. In specific embodiments, the display 4930 and the associated plurality of path progress indicators 4905-4925 may be configured to illustrate the progress of a guided vascular access device from an insertion point to one or more of the fourteen exemplary positions where two or more vessels join. Additionally or alternatively, the sensors positioned on the guided vascular access device that are represented by the path progress indicators 4905-4925 are positioned on the guided vascular access device to mimic one or more of the fourteen exemplary positions where two or more vessels join.

Speakers 4901 may be configured to provide an audible indication to the user that the device under user guidance is following the desired path. Sounds played may correspond to the indicator lights described elsewhere in this application. The audible indication may also be as simple as a monotone sound when the device is advancing properly and a stereo or other tone used to indicate when the device is no longer following the indicated path. The right audio channel may provide an audible indication of the Doppler frequencies and blood velocities away from the sensor and the left audio channel may provide an indication of the Doppler frequencies and blood velocities towards the sensor. Thus the right audio channel and the green LED provide indication that the device is following the desired path while the left audio channel and the red LED provide an indication that the device is on the wrong path.

Based on the signal processing results, the procedure specific user interface 4900 indicates to the user the location of the catheter or catheter tip in the vascular tree. In a simple embodiment colored lights may be used to indicate the position of the catheter tip, e.g., a green light may indicate blood flow away from the catheter meaning that the catheter is pushed the right way towards the heart. A red light may indicate blood flow towards the catheter meaning that the catheter is pushed the wrong way away from the heart. A blue light may indicate that a blood flow pattern has been detected that is indicative of the proximity of the junction between the vena cava and the right atrium.

For example, when a guided vascular access device is intended to be guided to the lower one-third of the SVC, then a specific display may be provided that can be used to indicated the likely guidance path from an entry in the basilic vein to the SVC as illustrated in FIG. 4 (see image 4940). In one embodiment, the position indicators 4905-4925 are LEDs and the display 4930 is a flat mount to hold a static figure that appears like image 4940 to which the LEDs are attached and visible to a user. It is to be appreciated that other vasculature specific pathways may also be indicated a display as part of a specific user interface 4900. Specific pathway applications are as varied as the procedures performed on or in the vasculature. The LED indicators to also be used to provide other processed signal outputs from the system as well including identification of a feature or portion of a vessel wall (i.e., identifying a stenosed portion of a vessel) or a specific, identifiable anatomical landmark such as a heart valve. It is to be appreciated that the specific user interface 4900 could be configured to provide a display or image indicating a suitable pathway from an access point to a treatment site. Additionally, the display or image indicating a suitable pathway may be outfitted to provide any form of user perceptible indication of movement of the guided vascular access device in accordance with the suitable pathway.

Figure 50A:
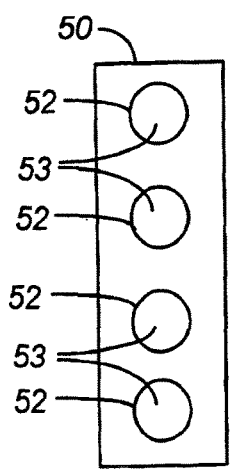
FIGS. 50A and 50B illustrate a basic user interface with control lights.
Figure 50B:
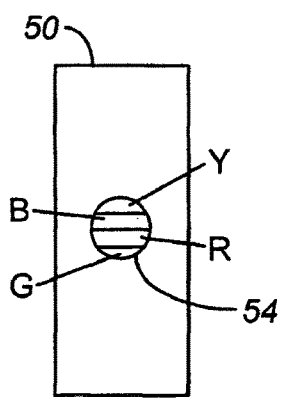

FIGS. 50A and 50B illustrate variations on the device progress indicator 50. The configuration of the device progress indicator 50 in FIG. 50A has 4 lights 52 each with an individual colored lens 53. The color indicators are associated to the device status indicators described herein. The configuration of the device indicator 50 illustrated in FIG. 50B includes a single light 54 and a multi-colored lens 54 to provide the device status indication. The lights 52, 54 may also be fiber optics, LEDs or any suitable source of light for a visual indication of device progress.

Figure 51:
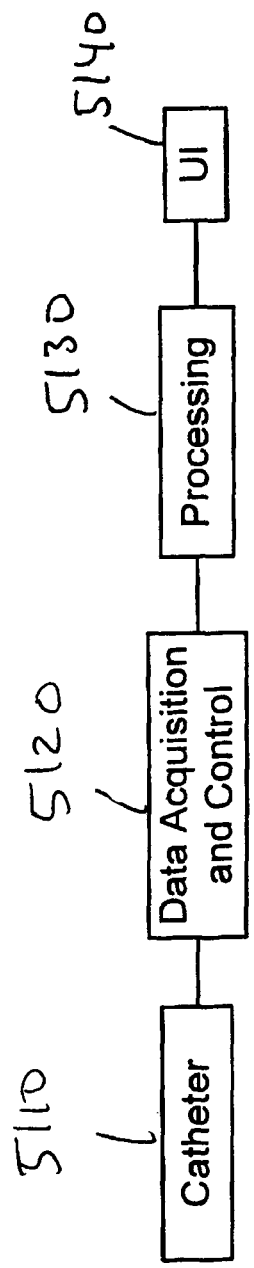
FIGS. 51 and 52 illustrate components of a system according to the invention.
Figure 52:
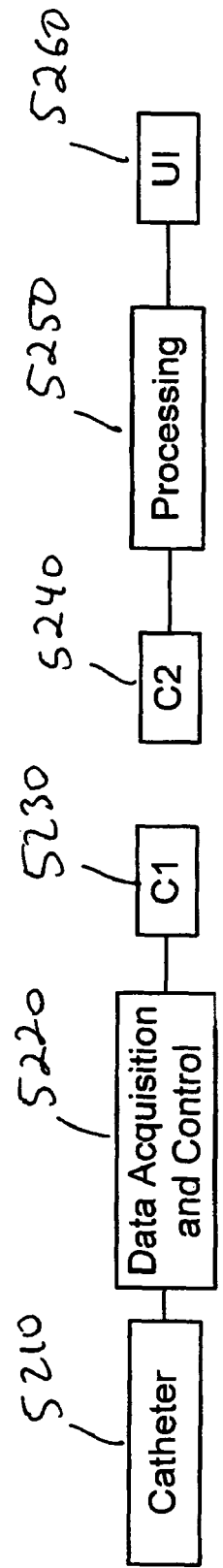

As illustrated in FIGS. 51 and 52, the components of the system described above and also illustrated in FIG. 2 may be in communication via conventional wire connections (FIG. 51) or by utilizing a wireless connection (FIG. 52). In one embodiment, the entire system is contained in a sterile package for single use.

In another alternative configuration, the components of the multi-single beam ultrasound system described herein are divided into two parts. One part is a reusable user interface having the processing system and the user interface functionality. The other part is a sterile single use guided vascular access device. The reusable user interface is maintained by a particular healthcare provider or as part of the equipment provided and maintained in an operating room or treatment area. Communication between the reusable user interface and the single use guided vascular access device may be provided using conventional wired or wireless techniques.

Wireless technology, such as the so called Bluetooth technology, may also be used to communicate information between components of the inventive multi-single beam ultrasound system described herein. In one embodiment, a wireless communication link is provided to allow communication between a grouping of disposable components on one side and the reusable components on the other side. The disposable side may, for example, include a guided vascular access device described herein (including one or more sensors), a data acquisition and control unit 5220 to control the high voltage and high frequency signal required to drive the ultrasound sensor and the connector C1 5230 used to communicate low throughput information via a Bluetooth wireless channel to the reusable side. The reusable side consist of the Bluetooth connector 5240 which communicate with its counterpart 5230, the processing and pattern analysis unit 5250 and the user interface 5260.

Bluetooth is a low-cost, flexible wireless platform for short-distance communication (<~10 meters). The cost of a Bluetooth radio chip has dropped from $20 and is now approximately $5. Bluetooth uses Gaussian frequency shift keying (GFSK) to modulate the data to frequencies around 2.4 GHz. Data is transmitted at 1 Mbps. For security benefits and noise reduction, a Bluetooth transmitter employs frequency hopping, switching channels up to 1600 times a second. Bluetooth is capable of point-to-point or point-to-multipoint communication. This flexibility allows Bluetooth to be used in a wide variety of applications. Because power consumption is always a concern for mobile devices, Bluetooth has three power classes that can be used depending on how far apart the communicating devices are from one another. Over the next few years, Bluetooth's use is expected to significantly grow. The Bluetooth consortium is currently writing the specifications for Bluetooth 2.0. Bluetooth 2.0 has been designed to complement existing Bluetooth devices and will offer data transmission rates up to 12 Mbps.

In one embodiment, the database used to store blood flow and other types of signature patterns is contained in the processing block. In this case the patterns are stored for the duration of a single procedure. In particular the calibration patterns stored in the beginning of the procedure are important in auto-scaling the signals through the procedure. In another embodiment the signature database is stored in the UI in flash memory. In yet another embodiment, the UI can communicate via conventional communication methods like Internet or LAN with any relevant database.

FIG. 51 shows a disposable guiding system with all components connected to the elongate member with sensor and packaged in the same sterile package as the elongate member 5110. In this embodiment the system is battery operated, the data acquisition and control unit 5120 is integrated into an ASIC (application specific integrated circuit) together with the processing algorithms 5130. In another embodiment, the processing algorithms are programmed into an FPGA (field programmable gate array). A DSP (digital signal processor) core is integrated into an FPGA to provide a flexible processing environment. The user interface 5140 consists of a light enclosure of approximately 200 g and of small size of approximately 3×3×1 cm with one LED of multiple colors. The enclosure also contains the data acquisition and control unit 5120 and the processing unit 5130. The power requirements of the multi single beam system presented in this invention are modest because it uses one or a few ultrasound beams for a small depth of penetration of maximum 15 mm. The ultrasound sensor size is small, the operating frequency low, the duty cycle low and the electronics including the wireless device are integrated and have low energy needs. For all these reasons the disposable system can be battery operated. At the quantities of this kind of product described herein projected to be sold on the market of several hundred thousands a year, the cost of goods becomes reasonable low for a disposable device.

Figure 53:
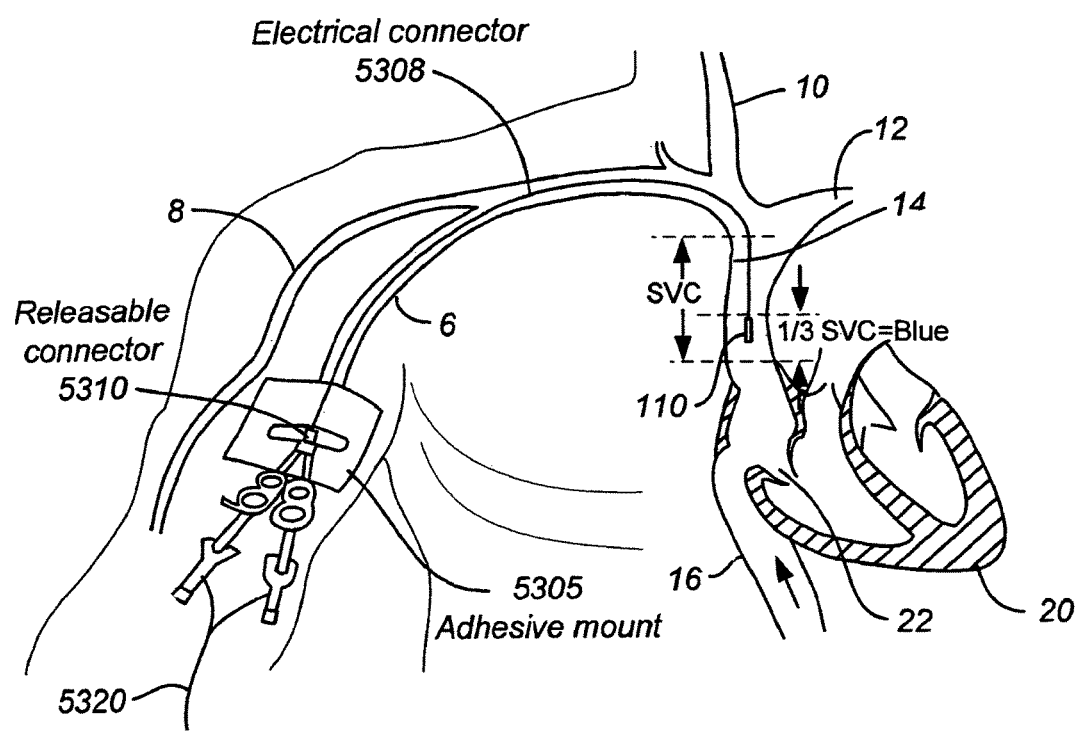
FIG. 53 illustrates local detection capabilities of the present invention.

FIG. 53 will be used to illustrate the location detection capabilities of the present invention may be used to determine whether a device has changed position from the position in which was originally installed. The ability to determine if catheter tip migration has occurred is an important clinical benefit of the present invention. For simplicity of illustration, the catheter tip is represented by the device 110. The device 110 is in communication with the processing system described herein an appropriate connector is inserted into connector 5310 to control the sensors in device 110. First, use the instrument to determine a location to secure a device 110 within the vasculature of a body. This determined position becomes the baseline or the compare to value to evaluate whether tip migration has occurred. As shown, the device 110 is in the SVC and is secured to the body using the adhesive mount 5305. The adhesive mount 5305 secures the device 110 to the body to maintain the device in the location determined by the instrument during placement of the catheter. Whenever the position of the catheter tip (here sensor 110) is to be checked, the sensor is reconnected to the system via connector 5310. Once the sensors in device 110 are in communication with the processing system, then the system will operate the sensors to acquire and process data to then calculate the position of the device. Then, the system may determine if the device is in the location determined by the instrument by comparing the calculated position of the device to the location determined by the instrument.

According to one embodiment of the present invention, there is provided a method for positioning an instrument in the vasculature of a body using the instrument determine a location to secure a device within the vasculature of a body; and securing the device to the body to maintain the device in the location determined by the instrument. After the passage of some period of time (as is common with patients who wear catheters for an extended period of time, the instrument may be used to calculate the current position of the device. Next, using the known original position and the now determined current position, the system can determine if the device has moved from the original position.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An endovascular navigation system, comprising:
   an elongate flexible member configured to access the venous vasculature of a patient;
   a sensor disposed at a distal end of the elongate flexible member and configured to sense a physiological signal of the venous vasculature of the patient;
   a processor configured to:
      receive the physiological signal of the venous vasculature of the patient provided by the sensor;
      process the physiological signal to determine one or more physiological characteristics of the venous vasculature of the patient;
      track a position of the distal end of the elongate flexible member within the venous vasculature of the patient over time; and
      determine, based on the one or more physiological characteristics of the venous vasculature of the patient, that the position of the distal end of the elongate flexible member is within a predetermined structure within the venous vasculature of the patient;
   a display output device configured to simultaneously display:
      a graphical representation of a path between tracked positions of the distal end of the elongate flexible member within the venous vasculature of the patient over time;
      a first visual indication of the position of the distal end of the elongate flexible member in real time;
      at least part of the physiological signal provided by the sensor over time; and
      a second visual indication that the distal end of the elongate flexible member is within the predetermined structure within the venous vasculature of the patient only when it is determined that the position of the distal end of the elongate flexible member is within the predetermined structure within the venous vasculature of the patient, wherein the second visual indication is different from the physiological characteristic of the venous vasculature of the patient, and the graphical representation is different from the at least part of the physiological signal and the second visual indication; and
   an audible output device configured to output an audible indication of the position of the distal end of the elongate flexible member.

2. The system of claim 1, wherein the predetermined structure within the venous vasculature of the patient is the superior vena cava of the patient.

3. The system of claim 2, wherein the predetermined structure within the venous vasculature of the patient is the lower one-third of the superior vena cava of the patient.

4. The system of claim 1, wherein the processor is configured to determine that the position of the distal end of the elongate flexible member is within the predetermined structure within the venous vasculature of the patient by determining that the physiological characteristic of the venous vasculature of the patient satisfies a threshold associated with the predetermined structure within the venous vasculature of the patient.

5. The system of claim 1, wherein the processor is configured to determine that the position of the distal end of the elongate flexible member is within the predetermined structure within the venous vasculature of the patient by comparing the physiological characteristic of the venous vasculature of the patient with a pattern associated with the predetermined structure within the venous vasculature of the patient.

6. The system of claim 5, wherein the processor is further configured to receive one or more patterns associated with the predetermined structure within the venous vasculature of the patient.

7. The system of claim 5, wherein the pattern associated with the predetermined structure within the venous vasculature of the patient is a blood flow pattern associated with the predetermined structure within the venous vasculature of the patient.

8. The system of claim 1, wherein the second visual indication that the distal end of the elongate flexible member is within the predetermined structure within the venous vasculature of the patient is a blue indicator.

9. The system of claim 1, wherein the display output device is configured to display at least part of the physiological signal provided by the sensor in real-time.

10. The system of claim 1, wherein the processor is further configured to dynamically calibrate settings of the endovascular navigation system for the patient based on the processing of the physiological signal of the venous vasculature of the patient.

11. The system of claim 1, wherein:
   the processor is further configured to determine, based on the one or more physiological characteristics of the venous vasculature of the patient, that the distal end of the elongate flexible member is against a wall of the venous vasculature of the patient; and
   the display output device is further configured to display, in response to the determination that the distal end of the elongate flexible member is against the wall of the venous vasculature of the patient, another visual indication that the distal end of the elongate flexible member is against the wall of the venous vasculature of the patient and to stop display of the second visual indication that the distal end of the elongate flexible member is within the predetermined structure within the venous vasculature of the patient.

12. The system of claim 1, wherein:
the processor is further configured to determine, based on the one or more physiological characteristics of the venous vasculature of the patient, that the distal end of the elongate flexible member is moving towards the predetermined structure within the venous vasculature of the patient; and
the display output device is further configured to display, in response to the determination that the distal end of the elongate flexible member is moving towards the predetermined structure within the venous vasculature of the patient, another visual indication that the distal end of the elongate flexible member is moving towards the predetermined structure within the venous vasculature of the patient and to stop display of the second visual indication that the distal end of the elongate flexible member is within the predetermined structure within the venous vasculature of the patient.

13. The system of claim 1, wherein:
the processor is further configured to determine, based on the one or more physiological characteristics of the venous vasculature of the patient, that the distal end of the elongate flexible member is moving away from the predetermined structure within the venous vasculature of the patient; and
the display output device is further configured to display, in response to the determination that the distal end of the elongate flexible member is moving away from the predetermined structure within the venous vasculature of the patient, another visual indication that the distal end of the elongate flexible member is moving away from the predetermined structure within the venous vasculature of the patient and to stop display of the second visual indication that the distal end of the elongate flexible member is within the predetermined structure within the venous vasculature of the patient.

14. The system of claim 1, wherein the sensor is configured to detach from the elongate flexible member while the elongate flexible member remains in the venous vasculature of a patient.

15. The system of claim 1, wherein the physiological signal of the venous vasculature of the patient comprises an in vivo non-image based ultrasound signal of the venous vasculature of the patient.

16. The system of claim 15, wherein the one or more physiological characteristics of the venous vasculature of the patient are selected from a group consisting of a blood flow direction, a blood flow velocity, a blood flow signature pattern, a pressure signature pattern, A-mode information, and a preferential non-random direction of flow.

17. The system of claim 1, wherein the processor is configured to receive the physiological signal of the venous vasculature of the patient from the sensor via a wireless connection.

18. The system of claim 1, wherein the elongate flexible member is a catheter, a guide wire, or a stylet.

19. An endovascular navigation method, comprising:
receiving a physiological signal of a venous vasculature of a patient provided from a sensor on a distal end of an elongate flexible member within the venous vasculature of the patient;
processing the physiological signal to determine one or more physiological characteristics of the venous vasculature of the patient;
tracking a position of the distal end of the elongate flexible member within the venous vasculature of the patient over time;
determining, based on the one or more physiological characteristics of the venous vasculature of the patient, that the position of the distal end of the elongate flexible member is within a predetermined structure within the venous vasculature of the patient;
simultaneously displaying:
a graphical representation of a path between tracked positions of the distal end of the elongate flexible member within the venous vasculature of the patient over time;
a first visual indication of the position of the distal end of the elongate flexible member in real time;
at least part of the physiological signal provided by the sensor over time; and
only when it is determined that the position of the distal end of the elongate flexible member is within the predetermined structure within the venous vasculature of the patient, a second visual indication that the distal end of the elongate flexible member is within the predetermined structure within the venous vasculature of the patient,
wherein the second visual indication is different from the physiological characteristic of the venous vasculature of the patient, and the graphical representation is different from the at least part of the physiological signal and the second visual indication; and
outputting an audible indication of the position of the distal end of the elongate flexible member.

20. The system of claim 1, wherein the processor is further configured to process the physiological signal to remove noise from and rescale the physiological signal before display of the physiological signal by the display output device.

21. The system of claim 1, wherein:
the processor is further configured to determine, based on the one or more physiological characteristics of the venous vasculature of the patient, that the distal end of the elongate flexible member is outside of the predetermined structure within the venous vasculature of the patient; and
the display output device is further configured to stop display of the second visual indication that the distal end of the elongate flexible member is within the predetermined structure within the venous vasculature of the patient while displaying the at least part of the physiological signal provided by the sensor over time.

22. The system of claim 1, wherein the display output device is configured to display the graphical representation of the path between positions of the distal end of the elongate flexible member within the venous vasculature of the patient over time by displaying an entirety of the path of the distal end of the elongate flexible member from an insertion point to the predetermined structure.

23. The system of claim 1, wherein the display output device is configured to display the graphical representation of the path between positions of the distal end of the elongate flexible member within the venous vasculature of the patient over time by simultaneously displaying an image showing the expected vessel travel path of the distal end of the elongate flexible member from an insertion point to the predetermined structure.

24. The system of claim 23, wherein the display output device is configured to display the graphical representation of the path between positions of the distal end of the elongate flexible member within the venous vasculature of the patient over time by simultaneously displaying an image showing the vascular tree of the patient.

* * * * *